(12) United States Patent
Kana et al.

(10) Patent No.: US 11,713,491 B2
(45) Date of Patent: Aug. 1, 2023

(54) DIAGNOSTIC CONTROL COMPOSITIONS

(71) Applicant: University of the Witwatersrand, Johannesburg, Johannesburg (ZA)

(72) Inventors: Bavesh Davandara Kana, Johannesburg (ZA); Edith Erika Machowski, Johannesburg (ZA)

(73) Assignee: UNIVERSITY OF THE WITWATERSRAND, JOHANNESBURG, Johannesburg (ZA)

( * ) Notice: Subject to any disclaimer, the term of this patent is extended or adjusted under 35 U.S.C. 154(b) by 0 days.

(21) Appl. No.: 17/996,919

(22) PCT Filed: Apr. 23, 2021

(86) PCT No.: PCT/IB2021/053369
§ 371 (c)(1),
(2) Date: Oct. 21, 2022

(87) PCT Pub. No.: WO2021/214724
PCT Pub. Date: Oct. 28, 2021

(65) Prior Publication Data
US 2023/0127238 A1   Apr. 27, 2023

(30) Foreign Application Priority Data
Apr. 23, 2020   (GB) ..................... 2005985

(51) Int. Cl.
| | |
|---|---|
| *C12N 15/09* | (2006.01) |
| *C12Q 1/68* | (2018.01) |
| *C12Q 1/70* | (2006.01) |
| *C12Q 1/00* | (2006.01) |
| *C12Q 1/6806* | (2018.01) |

(52) U.S. Cl.
CPC ............ *C12Q 1/70* (2013.01); *C12Q 1/6806* (2013.01); *C12Q 2522/101* (2013.01); *C12Q 2525/143* (2013.01); *C12Q 2545/113* (2013.01)

(58) Field of Classification Search
CPC ........ C12N 15/09; C12Q 1/6806; C12Q 1/70; C12Q 2525/143; C12Q 2522/101
See application file for complete search history.

(56) References Cited

FOREIGN PATENT DOCUMENTS

| WO | 03078575 A2 | 9/2003 |
|---|---|---|
| WO | 2009002193 A1 | 12/2008 |
| WO | 2012122732 A1 | 9/2012 |
| WO | 2017060662 A1 | 4/2017 |

OTHER PUBLICATIONS

Goncharova et al. (Mar. 2021) "One-step quantitative RT-PCR assay with armored RNA controls for detection of SARS-CoV-2", J Med Virol., 93(3):1694-1701.
Pasloske et al. (Dec. 1998) "Armored RNA technology for production of ribonuclease-resistant viral RNA controls and standards", J Clin Microbiol., 36(12):3590-3594.
Wu et al. (Mar. 12, 2020) "A New Coronavirus Associated with Human Respiratory Disease in China", Nature, 579(7798):265-269.

*Primary Examiner* — Barry A Chestnut
(74) *Attorney, Agent, or Firm* — Mintz, Levin, Cohn, Ferris, Glovsky & Popeo, P.C.

(57) ABSTRACT

Provided herein is a nucleotide cassette comprising an inducible promoter, a nucleotide sequence that corresponds to at least one single stranded RNA diagnostic target, a nucleotide sequence that encodes artemin, a molecular switch and a nucleotide sequence that encodes a DNAse enzyme and is under control of the molecular switch, wherein the single stranded RNA diagnostic target is a sequence detected by a molecular diagnostic assay. In some embodiments the nucleotide cassette can be used to obtain an RNA expression product. Also provided are vectors and cells comprising the nucleotide cassette or the RNA expression product thereof. The nucleotide cassette can further be used to obtain a diagnostic control composition comprising a non-pathogenic recombinant bacterium having a modified genetic content comprising the nucleotide cassette and to methods of producing such recombinant bacteria.

26 Claims, 6 Drawing Sheets

Specification includes a Sequence Listing.

```
GTTAACACTAGTTGATTAGCTAAGCAGAAGGCCATCCTGACGGATGGCCTTTTTGCGTTTAATACTGTTTAA
ACCTCTAGAGGTGTGGTAGCCGATGCCGGTGTTGGCGCCGGTGACCACAACGACGCGCCCGCTTTGATCGG
GGACGTCTGCGGCCGACCATTTACGGGTCTTGTTGTCGTTGGCGGTCATGGGCCGAACATACTCACCCGGAT
CGGAGGGCCGAGGACAAGGTCGAACGAGGGGCATGACCCGGTGCGGGCTTCTTGCACTCGGCATAGGC
GAGTGCTAAGAATAACGTTGGCACTCGCGACCGGTGAGTGCTAGGTCGGGACGGTGAGGCCAGGCCCGTC
GTCGCAGCGAGTGGCAGCGAGGACAACTTGAGCCGTCCGTCGCGGGCACTGCGCCCGGCCAGCGTAAGTA
GCGGGGTTGCCGTCACCCGGTGACCCCCGTTTCATCCCCGATCCGCATGCGGATCCCTGCAGAGTACTCTCT
TATTGTAACAGCTTTAAGGGCCAATTCTGCTGTCAAATTACAGAATAATGAGCTTAGTCCTGTTGCACTACGA
CAGATGTCTTGTGCTGCCGGTACTACACAAACTGCTTGCACTGATGACAATGCGTTAGCTTACTACAACACA
ACAAAGGGAGGTAGGTTTGTACTTGCACTGTTATCCGATTTACAGGATTTGAAATGGGCTAGTACTCAGCTG
GAAATGCTGGTATTGTTGGTGTACTGACATTAGATAATCAAGATCTCAATGGTAACTGGTATGATTTCGGTG
ATTTCATACAAACCACGCCAGGTAGTGGAGTTCCTGTTGTAGATTCTTATTATTCATTGTTAATGCCTATATTA
ACCTTGACCAGGGCTTTAACTGCAGAGTCACATGTTGACACTGACTTAACAAAGCCTTACACAGCTGGATAT
CTTTAGATTTCATCTAAACGAACAAACTAAAATGTCTGATAATGGACCCCAAAATCAGCGAAATGCACCCCG
CATTACGTTTGGTGGACCCTCAGATTCAACTGGCAGTAACCAGAATGGAGAACGCAGTGGGGCGCGATCAA
AACAACGTCGGCCCCAAGGTTTACCCAATAATACTGCGTCTTGGTTCACCGCTCTCACTCAACATGGCAAGG
AAGACCTTAAATTCCCTCGAGGACAAGGCGTTCCAATTAACACCAATAGCAGTCCAGATGACCAAATTGGCT
ACTACCGAAGAGCTACCAGACGAATTCGTGGTGGTGACGGTAAAATGAAAGATCTCAGTCCAAGATGGTAT
TTCTACTACCTAGGAACTGGGCCAGAAGCTGGACTTCCCTATGGTGCTAACAAAGACGGCATCATATGGGTT
GCAACTGAGGGAGCCTTGAATACACCAAAAGATCACATTGGCACCCGCAATCCTGCTAACAATGCTGCAATC
GTGCTACAACTTCCTCAAGGAACAACATTGCCAAAAGGCTTCTACGCAGAAGGGAGCAGAGGCGGCAGTCA
AGCCTCTTCTCGTTCCTCATCACGTAGTCGCAACAGTTCAAGAAATTCAACTCCAGGCAGCAGTAGGGGAAC
TTCTCCTGCTAGAATGGCTGGCAATGGCGGTGATGCTGCTCTTGCTTTGCTGCTGCTTGACAGATTGAACCA
GCTTGAGAGCAAAATGTCTGGTAAAGGCCAACAACAACAAGGCCAAACTGTCACTAAGAAATCTGCTGCTG
AGGCTTCTAAGAAGCCTCGGCAAAAACGTACTGCCACTAAAGCATACAATGTAACACAAGCTTTCGGCAGAC
GTGGTCCAGAACAAACCCAAGGAAATTTTGGGGACCAGGAACTAATCAGACAAGGAACTGATTACAAACAT
TGGCCGCAAATTGCACAATTTGCCCCCAGCGCTTCAGCGTTCTTCGGAATGTCGCGCATTGGCATGGAAGTC
ACACCTTCGGGAACGTGGTTGACCTACACAGGTGCCATCAAATTGGATGACAAAGATCCAAATTTCAAAGAT
CAAGTCATTTTGCTGAATAAGCATATGATATCTACGTACTCATTCGTTTCGGAAGAGACAGGTACGTTAATA
GTTAATAGCGTACTTCTTTTTCTTGCTTTCGTGGTATTCTTGCTAGTTACACTAGCCATCCTTACTGCGCTTCGA
TTGTGTGCGTACTGCTGCAATATTGTTAACGTGAGTCTTGTAAAACCTTCTTTTTACGTTTACTCTCGTGTTAA
AAATCTGAATTCTTCTAGAGTTCCTGATCTTCTGGTCTAATACGTAAAGCTTAGGAAGGAATGTACATATGGC
GACCGAGGGCGCGCGCAACATCGGCCAGTCGGCCCCGGAGGGCAAGGTGCAGATGGACTGCCCGTCGCGC
CACAACTTCGACCCGGAGTGCGAGAAGGCGTTTGTGGAGCACATCCACCTTGAGCTGGCCTCGTCGTACCA
CGCATGGTCGATGTGGGCCTTCTACGCCCGCGACTGCAAGGCCGCCGTGGGCATGACCCGCCTGTGCGAGT
GGGCCTCGCACGTCTCGGCCCAGCGCGCCCGCCGCATGGCCGCCTACGTGCTGACCCGCGGCGGCCACGTG
GACTACAAGGAGATCCCGGCCCCGAAGAAGCAGGGCTGGGACAACTTCGAGGACGCCTTCTCGCACTGCGT
GGCGAACAAGAAGCGCATCCTGACCTCGCTCCAGTCGCTGTACCAGTGCTGCCAGTCGAAGGACGCCCACT
GCTCGAACTTCATCCAGACCGACATGATGGACGAGGTGATCGCGTGGAACAAGTTTCTGTCGGACTGCCTG
TCGAACCTGCACTGCATCGGCTCGCAGGGCATGGGACCGTGGGTGTTCGACCGCTGGCTGGCCCGCATCGT
GATGTCGAAGTTCAAGCACCCGAAGATCCCGTCGCTCTCGACCTCGGACCTAGAGTCGAACATCCCGAACG
AGCTGTTCGACGCCGAGGGCGACATGGTGCGCGCCATCAAGAAGCTGGACTACAAGGACCATGACGGTGA
CTATAAAGATCACGATATAGATTACAAGGATGACGATGACAAGTGACTTAAGGGTACCGGTGATACCAGCA
TCGTCTTGATGCCCTGGCAGCACCCTGCTAAGGAGGCAACAAGATGCATACCATCTACCGCATCGAGAAGA
AGGAGAACTACGTGGTGCTGGACAAGGGCTTCCTGCACGACCGCGAGCTGTCGTGGCAGGCTAAGGGCCT
```

Figure 4

```
GTTAACACTAGTTGATTAGCTAAGCAGAAGGCCATCCTGACGGATGGCCTTTTTGCGTTTAATACTGTTTAA
ACCTCTAGAGGTGTGGTAGCCGATGCCGGTGTTGGCGCCGGTGACCACAACGACGCGCCCGCTTTGATCGG
GGACGTCTGCGGCCGACCATTTACGGGTCTTGTTGTCGTTGGCGGTCATGGGCCGAACATACTCACCCGGAT
CGGAGGGCCGAGGACAAGGTCGAACGAGGGGCATGACCCGGTGCGGGGCTTCTTGCACTCGGCATAGGC
GAGTGCTAAGAATAACGTTGGCACTCGCGACCGGTGAGTGCTAGGTCGGGACGGTGAGGCCAGGCCCGTC
GTCGCAGCGAGTGGCAGCGAGGACAACTTGAGCCGTCCGTCGCGGGCACTGCGCCCGGCCAGCGTAAGTA
GCGGGGTTGCCGTCACCCGGTGACCCCCGTTTCATCCCCGATCCGCATGCGGATCTCGACACTTGAACAGCC
CTATGTGTTCATCAAACGTTCGGATGCTCGAACTGCACCTCATGGTCATGTTATGGTTGAGCTGGTAGCAGA
ACTCGAAGGCATTCAGTACGGTCGTAGTGGTGAGACACTTGGTGTCCTTGTCCCTCATGTGGGCGAAATACC
AGTGGCTTACCGCAAGGTTCTTCTTCGTAAGAACGGTAATAAAGGAGCTGGTGGCCATAGTTACGGCGCCG
ATCTAAAGTCATTTGACTTAGGCGACGAGCTTGGCACTGATCCTTATGAAGATTTTCAAGAAAACTGGAACA
CTAAACATAGCAGTGGTGTTACCCGTGAACTCATGCGTGAGCTTAACGGAGGGGCATACACTCGCTATGTC
GATAACAACTTCTGTGGCCCTGATGGCTACAAGCTTAAATTGATTGCCAACCAATTTAATAGTGCTATTGGCA
AAATTCAAGACTCACTTCTTCCACAGCAAGTGCACTTGGAAAACTTCAAGATGTGGTCAACCAAAATGCAC
AAGCTTTAAACACGCTTGTTAAACAACTTAGCTCCAATTTTGGTGCAATTTCAAGTGTTTTAAATGATATCCTT
TCACGTCTTGACAAAGTTGAGGCTGAAGTGCAAATTGATAGGTTGATCACAGGCAGACTTCAAAGTTTGCA
GACATATGTGACTCAACAATTAATTAGAGCTGCAGAAATCAGAGCTTCTGCTAATCTTGCTGCTACTAAAAT
GTAGATCGATCCCTGCAGAGTACTCTCTTATTGTAACAGCTTTAAGGGCCAATTCTGCTGTCAAATTACAGAA
TAATGAGCTTAGTCCTGTTGCACTACGACAGATGTCTTGTGCTGCCGGTACTACACAAACTGCTTGCACTGAT
GACAATGCGTTAGCTTACTACAACACAACAAAGGGAGGTAGGTTTGTACTTGCACTGTTATCCGATTTACAG
GATTTGAAATGGGCTAGTACTCAGCTGGAAATGCTGGTATTGTTGGTGTACTGACATTAGATAATCAAGATC
TCAATGGTAACTGGTATGATTTCGGTGATTTCATACAAACCACGCCAGGTAGTGGAGTTCCTGTTGTAGATT
CTTATTATTCATTGTTAATGCCTATATTAACCTTGACCAGGGCTTTAACTGCAGAGTCACATGTTGACACTGAC
TTAACAAAGCCTTACACAGCTGGATATCTTTAGATTTCATCTAAACGAACAAACTAAAATGTCTGATAATGGA
CCCCAAAATCAGCGAAATGCACCCCGCATTACGTTTGGTGGACCCTCAGATTCAACTGGCAGTAACCAGAAT
GGAGAACGCAGTGGGGCGCGATCAAAACAACGTCGGCCCCAAGGTTTACCCAATAATACTGCGTCTTGGTT
CACCGCTCTCACTCAACATGGCAAGGAAGACCTTAAATTCCCTCGAGGACAAGGCGTTCCAATTAACACCAA
TAGCAGTCCAGATGACCAAATTGGCTACTACCGAAGAGCTACCAGACGAATTCGTGGTGGTGACGGTAAAA
TGAAAGATCTCAGTCCAAGATGGTATTTCTACTACCTAGGAACTGGGCCAGAAGCTGGACTTCCCTATGGTG
CTAACAAAGACGGCATCATATGGGTTGCAACTGAGGGAGCCTTGAATACACCAAAAGATCACATTGGCACC
CGCAATCCTGCTAACAATGCTGCAATCGTGCTACAACTTCTCAAGGAACAACATTGCCAAAAGGCTTCTAC
GCAGAAGGGAGCAGAGGCGGCAGTCAAGCCTCTTCTCGTTCCTCATCACGTAGTCGCAACAGTTCAAGAAA
TTCAACTCCAGGCAGCAGTAGGGGAACTTCTCCTGCTAGAATGGCTGGCAATGGCGGTGATGCTGCTCTTGC
TTTGCTGCTGCTTGACAGATTGAACCAGCTTGAGAGCAAAATGTCTGGTAAAGGCCAACAACAACAAGGCC
AAACTGTCACTAAGAAATCTGCTGCTGAGGCTTCTAAGAAGCCTCGGCAAAAACGTACTGCCACTAAAGCAT
ACAATGTAACACAAGCTTTCGGCAGACGTGGTCCAGAACAAACCCAAGGAAATTTTGGGGACCAGGAACTA
ATCAGACAAGGAACTGATTACAAACATTGGCCGCAAATTGCACAATTTGCCCCCAGCGCTTCAGCGTTCTTC
GGAATGTCGCGCATTGGCATGGAAGTCACACCTTCGGGAACGTGGTTGACCTACACAGGTGCCATCAAATT
GGATGACAAAGATCCAAATTTCAAAGATCAAGTCATTTTGCTGAATAAGCATATGATATCTACGTACTCATTC
GTTTCGGAAGAGACAGGTACGTTAATAGTTAATAGCGTACTTCTTTTTCTTGCTTTCGTGGTATTCTTGCTAG
TTACACTAGCCATCCTTACTGCGCTTCGATTGTGTGCGTACTGCTGCAATATTGTTAACGTGAGTCTTGTAAA
ACCTTCTTTTTACGTTTACTCTCGTGTTAAAAATCTGAATTCTTCTAGAGTTCCTGATCTTCTGGTCTAATACGT
AAAGCTTAGGAAGGAATGTACATATGGCGACCGAGGGCGCGCGCAACATCGGCCAGTCGGCCCCGGAGGG
CAAGGTGCAGATGGACTGCCCGTCGCGCCACAACTTCGACCCGGAGTGCGAGAAGGCGTTTGTGGAGCAC
ATCCACCTTGAGCTGGCCTCGTCGTACCACGCATGGTCGATGTGGGCCTTCTACGCCCGCGACTGCAAGGCC
```

Figure 5

GCAUGCGGAUCCCUGCAGAGUACUCUCUUAUUGUAACAGCUUUAAGGGCCAAUUCUGCUGUCAAAUU
ACAGAAUAAUGAGCUUAGUCCUGUUGCACUACGACAGAUGUCUUGUGCUGCCGGUACUACACAAACU
GCUUGCACUGAUGACAAUGCGUUAGCUUACUACAACACAACAAAGGGAGGUAGGUUUGUACUUGCAC
UGUUAUCCGAUUUACAGGAUUUGAAAUGGGCUAGUACUCAGCUGGAAAUGCUGGUAUUGUUGGUGU
ACUGACAUUAGAUAAUCAAGAUCUCAAUGGUAACUGGUAUGAUUCGGUGAUUUCAUACAAACCACG
CCAGGUAGUGGAGUUCCUGUUGUAGAUUCUUAUUAUUCAUUGUUAAUGCCUAUAUUAACCUUGACC
AGGGCUUUAACUGCAGAGUCACAUGUUGACACUGACUUAACAAAGCCUUACACAGCUGGAUAUCUUU
AGAUUUCAUCUAAACGAACAAACUAAAAUGUCUGAUAAUGGACCCCAAAAUCAGCGAAAUGCACCCCG
CAUUACGUUGGUGGACCCUCAGAUUCAACUGGCAGUAACCAGAAUGGAGAACGCAGUGGGGCGCGA
UCAAAACAACGUCGGCCCCAAGGUUUACCCAAUAAUACUGCGUCUUGGUUCACCGCUCUCACUCAACA
UGGCAAGGAAGACCUUAAAUUCCCUCGAGGACAAGGCGUUCCAAUUAACACCAAUAGCAGUCCAGAUG
ACCAAAUUGGCUACUACCGAAGAGCUACCAGACGAAUUCGUGGUGGUGACGGUAAAAUGAAAGAUCU
CAGUCCAAGAUGGUAUUUCUACUACCUAGGAACUGGGCCAGAAGCUGGACUUCCCUAUGGUGCUAAC
AAAGACGGCAUCAUAUGGGUUGCAACUGAGGGAGCCUUGAAUACACCAAAAGAUCACAUUGGCACCCG
CAAUCCUGCUAACAAUGCUGCAAUCGUGCUACAACUUCCUCAAGGAACAACAUUGCCAAAAGGCUUCU
ACGCAGAAGGGAGCAGAGGCGGCAGUCAAGCCUCUUCUCGUUCCUCAUCACGUAGUCGCAACAGUUCA
AGAAAUUCAACUCCAGGCAGCAGUAGGGGAACUUCUCCUGCUAGAAUGGCUGGCAAUGGCGGUGAUG
CUGCUCUUGCUUUGCUGCUGCUUGACAGAUUGAACCAGCUUGAGAGCAAAAUGUCUGGUAAAGGCCA
ACAACAACAAGGCCAAACUGUCACUAAGAAAUCUGCUGCUGAGGCUUCUAAGAAGCCUCGGCAAAAAC
GUACUGCCACUAAAGCAUACAAUGUAACACAAGCUUUCGGCAGACGUGGUCCAGAACAAACCCAAGGA
AAUUUUGGGGACCAGGAACUAAUCAGACAAGGAACUGAUUACAAACAUUGGCCGCAAAUUGCACAAU
UUGCCCCCAGCGCUUCAGCGUUCUUCGGAAUGUCGCGCAUUGGCAUGGAAGUCACACCUUCGGGAAC
GUGGUUGACCUACACAGGUGCCAUCAAAUUGGAUGACAAAGAUCCAAAUUUCAAAGAUCAAGUCAUU
UUGCUGAAUAAGCAUAUGAUAUCUACGUACUCAUUCGUUUCGGAAGAGACAGGUACGUUAAUAGUU
AAUAGCGUACUUCUUUUCUUGCUUUCGUGGUAUUCUUGCUAGUUACACUAGCCAUCCUUACUGCGC
UUCGAUUGUGUGCGUACUGCUGCAAUAUUGUUAACGUGAGUCUUGUAAAACCUUCUUUUUACGUUU
ACUCUCGUGUUAAAAAUCUGAAUUCUUCUAGAGUUCCUGAUCUUCUGGUCUAAUACGUAAAGCUUAG
GAAGGAAUGUACAUAUGGCGACCGAGGGCGCGCGCAACAUCGGCCAGUCGGCCCCGGAGGGCAAGGU
GCAGAUGGACUGCCCGUCGCGCCACAACUUCGACCCGGAGUGCGAGAAGGCGUUUGUGGAGCACAUCC
ACCUUGAGCUGGCCUCGUCGUACCACGCAUGGUCGAUGUGGGCCUUCUACGCCCGCGACUGCAAGGCC
GCCGUGGGCAUGACCCGCCUGUGCGAGUGGGCCUCGCACGUCUCGGCCCAGCGCGCCCGCCGCAUGGC
CGCCUACGUGCUGACCCGCGGCGGCCACGUGGACUACAAGGAGAUCCCGGCCCCGAAGAAGCAGGGCU
GGGACAACUUCGAGGACGCCUUCUCGCACUGCGUGGCGAACAAGAAGCGCAUCCUGACCUCGCUCCAG
UCGCUGUACCAGUGCUGCCAGUCGAAGGACGCCCACUGCUCGAACUUCAUCCAGACCGACAUGAUGGA
CGAGGUGAUCGCGUGGAACAAGUUUCUGUCGGACUGCCUGUCGAACCUGCACUGCAUCGGCUCGCAG
GGCAUGGGACCGUGGGUGUUCGACCGCUGGCUGGCCCGCAUCGUGAUGUCGAAGUUCAAGCACCCGA
AGAUCCCGUCGCUCUCGACCUCGGACCUAGAGUCGAACAUCCCGAACGAGCUGUUCGACGCCGAGGGC
GACAUGGUGCGCGCCAUCAAGAAGCUGGACUACAAGGACCAUGACGGUGACUAUAAAGAUCACGAUA
UAGAUUACAAGGAUGACGAUGACAAGUGACUUAAGGGUACCGGUGAUACCAGCAUCGUCUUGAUGCC
CUGGCAGCACCCUGCUAAGGAGGCAACAAGAUGCAUACCAUCUACCGCAUCGAGAAGAAGGAGAACUA
CGUGGUGCUGGACAAGGGCUUCCUGCACGACCGCGAGCUGUCGUGGCAGGCUAAGGGCCUGCUGGCC
UUCAUGCUGUCGAUGCCGAACGACUGGGUGUUCAACAUGAAGGACCUCCAGAACCGCUCGAAGAACGG
UCGCGACGCCACCUACCGCAUUAUGAAGGAGCUGAUCGAGGCCGGCUACGUGACCCGCGUGGAGAACC
GCGACGGCGGCAAGUUCGGCAAGGUGGAGUACGUGGUCCACGAGGUGAAGCAGUCGCCGCACACCGA
GUCGCCGGACACCGUGCCGCCCUGCACCGAGAACCCGUACCCCGGCAACCCGUACCCCGGCAACCCGUAC

Figure 7

SEQUENCE LISTING

```
<160> NUMBER OF SEQ ID NOS: 28

<210> SEQ ID NO 1
<211> LENGTH: 474
<212> TYPE: DNA
<213> ORGANISM: Mycobacterium bovis

<400> SEQUENCE: 1
gttaacacta gttgattagc taagcagaag gccatcctga cggatggcct ttttgcgttt      60
aatactgttt aaacctctag aggtgtggta gccgatgccg gtgttggcgc cggtgaccac     120
aacgacgcgc ccgctttgat cggggacgtc tgcggccgac catttacggg tcttgttgtc     180
gttggcggtc atgggccgaa catactcacc cggatcggag ggccgaggac aaggtcgaac     240 gagggggcatg acccggtgcg gggcttcttg cactcggcat aggcgagtgc taagaataac    300
gttggcactc gcgaccggtg agtgctaggt cgggacggtg aggccaggcc cgtcgtcgca     360
gcgagtggca gcgaggacaa cttgagccgt ccgtcgcggg cactgcgccc ggccagcgta     420
agtagcgggg ttgccgtcac ccggtgaccc ccgtttcatc cccgatccgc atgc            474

<210> SEQ ID NO 2
<211> LENGTH: 209
<212> TYPE: DNA
<213> ORGANISM: SARS-CoV-2

<400> SEQUENCE: 2
ctcttattgt aacagcttta agggccaatt ctgctgtcaa attacagaat aatgagctta      60
gtcctgttgc actacgacag atgtcttgtg ctgccggtac tacacaaact gcttgcactg     120
atgacaatgc gttagcttac tacaacacaa caaagggagg taggtttgta cttgcactgt    180
tatccgattt acaggatttg aaatgggct                                        209

<210> SEQ ID NO 3
<211> LENGTH: 207
<212> TYPE: DNA
<213> ORGANISM: SARS-CoV-2

<400> SEQUENCE: 3
gaaatgctgg tattgttggt gtactgacat tagataatca agatctcaat ggtaactggt      60
atgatttcgg tgatttcata caaaccacgc caggtagtgg agttcctgtt gtagattctt     120
attattcatt gttaatgcct atattaacct tgaccagggc tttaactgca gagtcacatg     180
ttgacactga cttaacaaag ccttaca                                          207

<210> SEQ ID NO 4
<211> LENGTH: 1100
```

```
<212> TYPE: DNA
<213> ORGANISM: SARS-CoV-2

<400> SEQUENCE: 4
tttagatttc atctaaacga acaaactaaa atgtctgata atggacccca aaatcagcga      60
aatgcacccc gcattacgtt tggtggaccc tcagattcaa ctggcagtaa ccagaatgga     120
gaacgcagtg gggcgcgatc aaaacaacgt cggccccaag gtttacccaa taatactgcg     180
tcttggttca ccgctctcac tcaacatggc aaggaagacc ttaaattccc tcgaggacaa     240
ggcgttccaa ttaacaccaa tagcagtcca gatgaccaaa ttggctacta ccgaagagct     300
accagacgaa ttcgtggtgg tgacggtaaa atgaaagatc tcagtccaag atggtatttc     360
tactacctag gaactgggcc agaagctgga cttccctatg gtgctaacaa agacggcatc     420
atatgggttg caactgaggg agccttgaat acaccaaaag atcacattgg cacccgcaat     480
cctgctaaca atgctgcaat cgtgctacaa cttcctcaag gaacaacatt gccaaaaggc     540
ttctacgcag aagggagcag aggcggcagt caagcctctt ctcgttcctc atcacgtagt     600
cgcaacagtt caagaaattc aactccaggc agcagtaggg gaacttctcc tgctagaatg     660
gctggcaatg gcggtgatgc tgctcttgct ttgctgctgc ttgacagatt gaaccagctt     720
gagagcaaaa tgtctggtaa aggccaacaa caacaaggcc aaactgtcac taagaaatct     780
gctgctgagg cttctaagaa gcctcggcaa aaacgtactg ccactaaagc atacaatgta     840
acacaagctt tcggcagacg tggtccagaa caaacccaag gaaattttgg ggaccaggaa     900
ctaatcagac aaggaactga ttacaaacat tggccgcaaa ttgcacaatt gccccccagc     960
gcttcagcgt tcttcggaat gtcgcgcatt ggcatggaag tcacaccttc gggaacgtgg    1020
ttgacctaca caggtgccat caaattggat gacaagatc caaatttcaa agatcaagtc    1080
attttgctga taagcatat                                                  1100

<210> SEQ ID NO 5
<211> LENGTH: 222
<212> TYPE: DNA
<213> ORGANISM: SARS-CoV-2

<400> SEQUENCE: 5
tcattcgttt cggaagagac aggtacgtta atagttaata gcgtacttct ttttcttgct      60
ttcgtggtat tcttgctagt tacactagcc atccttactg cgcttcgatt gtgtgcgtac     120
tgctgcaata ttgttaacgt gagtcttgta aaaccttctt tttacgttta ctctcgtgtt     180
aaaaatctga attcttctag agttcctgat cttctggtct aa                        222

<210> SEQ ID NO 6
<211> LENGTH: 328
<212> TYPE: DNA
<213> ORGANISM: SARS-CoV-2

<400> SEQUENCE: 6
aaattgattg ccaaccaatt taatagtgct attggcaaaa ttcaagactc actttcttcc      60
acagcaagtg cacttggaaa acttcaagat gtggtcaacc aaaatgcaca agctttaaac     120
acgcttgtta acaacttag ctccaatttt ggtgcaattt caagtgtttt aaatgatatc     180
ctttcacgtc ttgacaaagt tgaggctgaa gtgcaaattg ataggttgat cacaggcaga     240
cttcaaagtt tgcagacata tgtgactcaa caattaatta gagctgcaga aatcagagct     300
tctgctaatc ttgctgctac taaaatgt                                        328
```

<210> SEQ ID NO 7
<211> LENGTH: 400
<212> TYPE: DNA
<213> ORGANISM: SARS-CoV-2

<400> SEQUENCE: 7
acttgaacag ccctatgtgt tcatcaaacg ttcggatgct cgaactgcac ctcatggtca 60
tgttatggtt gagctggtag cagaactcga aggcattcag tacggtcgta gtggtgagac 120
acttggtgtc cttgtccctc atgtgggcga aataccagtg gcttaccgca aggttcttct 180
tcgtaagaac ggtaataaag gagctggtgg ccatagttac ggcgccgatc taaagtcatt 240
tgacttaggc gacgagcttg gcactgatcc ttatgaagat tttcaagaaa actggaacac 300
taaacatagc agtggtgtta cccgtgaact catgcgtgag cttaacggag ggcatacac 360 tcgctatgtc gataacaact tctgtggccc tgatggctac 400

<210> SEQ ID NO 8
<211> LENGTH: 775
<212> TYPE: DNA
<213> ORGANISM: Artemia salina

<400> SEQUENCE: 8
aggaaggaat gtacatatgg cgaccgaggg cgcgcgcaac atcggccagt cggccccgga 60
gggcaaggtg cagatggact gcccgtcgcg ccacaacttc gacccggagt gcgagaaggc 120
gtttgtggag cacatccacc ttgagctggc ctcgtcgtac cacgcatggt cgatgtgggc 180
cttctacgcc cgcgactgca aggccgccgt gggcatgacc cgcctgtgcg agtgggcctc 240
gcacgtctcg gcccagcgcg cccgccgcat ggccgcctac gtgctgaccc gcggcggcca 300
cgtggactac aaggagatcc cggccccgaa gaagcagggc tgggacaact tcgaggacgc 360
cttctcgcac tgcgtggcga acaagaagcg catcctgacc tcgctccagt cgctgtacca 420
gtgctgccag tcgaaggacg cccactgctc gaacttcatc cagaccgaca tgatggacga 480
ggtgatcgcg tggaacaagt ttctgtcgga ctgcctgtcg aacctgcact gcatcggctc 540
gcagggcatg ggaccgtggg tgttcgaccg ctggctggcc cgcatcgtga tgtcgaagtt 600
caagcacccg aagatcccgt cgctctcgac ctcggaccta gagtcgaaca tcccgaacga 660
gctgttcgac gccgagggcg acatggtgcg cgccatcaag aagctggact acaaggacca 720
tgacggtgac tataaagatc acgatataga ttacaaggat gacgatgaca agtga 775

<210> SEQ ID NO 9
<211> LENGTH: 888
<212> TYPE: DNA
<213> ORGANISM: Bacteriophage GBSV1

<400> SEQUENCE: 9
atgcatacca tctaccgcat cgagaagaag gagaactacg tggtgctgga caagggcttc 60
ctgcacgacc gcgagctgtc gtggcaggct aagggcctgc tggccttcat gctgtcgatg 120
ccgaacgact gggtgttcaa catgaaggac ctccagaacc gctcgaagaa cggtcgcgac 180
gccacctacc gcattatgaa ggagctgatc gaggccggct acgtgacccg cgtggagaac 240
cgcgacggcg gcaagttcgg caaggtggag tacgtggtcc acgaggtgaa gcagtcgccg 300
cacaccgagt cgccggacac cgtgccgccc tgcaccgaga acccgtaccc cggcaacccg 360
taccccggca acccgtaccc ggagaacccg ccgctgctga acaacaacaa caccaactac 420
aagaacacca acaacgacga cgacaacaag gaccgcccga agaccaactc gctgaacgcc 480

| | | |
|---|---|---|
| tttcgcttct acgaggagaa cttccagccg accctgtcgt cggtggacat cgagatcctg | 540 |
| aactactggc tggaccgctt cccggaggag atcgtgctgt gcgccatgcg gaaggcccta | 600 |
| gagcagaacg tgcgctcgat caagtacatc gaccgcatcc ttgccaactg ggagatgcag | 660 |
| aaggtgcaga cccttgagga cgtggcccgc ctcgaccgcc agtacgagct ggagaagcag | 720 |
| gcccgccaga gcgcggcgg cgtggtgaac ggctcggtcc accagcaccg cggctcggac | 780 |
| ggtcgctcga cgaaggagga cgagcgcatc tcgcactacg agcccggcaa gtgggacgac | 840 |
| gtggacatct cgctggacgg cctgctgcac catcaccacc atcactga | 888 |

<210> SEQ ID NO 10
<211> LENGTH: 1005
<212> TYPE: DNA
<213> ORGANISM: Escherichia coli

<400> SEQUENCE: 10

| | | |
|---|---|---|
| gatctgcatt aatgaatcgg ccaacgcgcg gggagaggcg gtttgcgtat tgggcgctct | 60 |
| tccgcttcct cgctcactga ctcgctgcgc tcggtcgttc ggctgcggcg agcggtatca | 120 |
| gctcactcaa aggcggtaat acggttatcc acagaatcag gggataacgc aggaaagaac | 180 |
| atgtgagcaa aaggccagca aaaggccagg aaccgtaaaa aggccgcgtt gctggcgttt | 240 |
| ttccataggc tccgcccccc tgacgagcat cacaaaaatc gacgctcaag tcagaggtgg | 300 |
| cgaaacccga caggactata aagataccag gcgtttcccc ctggaagctc cctcgtgcgc | 360 |
| tctcctgttc cgaccctgcc gcttaccgga tacctgtccg cctttctccc ttcgggaagc | 420 |
| gtggcgcttt ctcatagctc acgctgtagg tatctcagtt cggtgtaggt cgttcgctcc | 480 |
| aagctgggct gtgtgcacga accccccgtt cagcccgacc gctgcgcctt atccggtaac | 540 |
| tatcgtcttg agtccaaccc ggtaagacac gacttatcgc cactggcagc agccactggt | 600 |
| aacaggatta gcagagcgag gtatgtaggc ggtgctacag agttcttgaa gtggtggcct | 660 |
| aactacggct acactagaag aacagtattt ggtatctgcg ctctgctgaa gccagttacc | 720 |
| ttcggaaaaa gagttggtag ctcttgatcc ggcaaacaaa ccaccgctgg tagcggtggt | 780 |
| ttttttgttt gcaagcagca gattacgcgc agaaaaaaag gatctcaaga agatcctttg | 840 |
| atcttttcta cggggtctga cgctcagtgg aacgaaaact cacgttaagg gattttggtc | 900 |
| atgagattat caaaaaggat cttcacctag atccttttaa attaaaaatg aagttttaaa | 960 |
| tcaagcccaa tctgaataat gttacaacca attaaccaat tctga | 1005 |

<210> SEQ ID NO 11
<211> LENGTH: 810
<212> TYPE: DNA
<213> ORGANISM: Artificial Sequence
<220> FEATURE:
<223> OTHER INFORMATION: Kanamycin resistance cassette

<400> SEQUENCE: 11

| | | |
|---|---|---|
| atgagccata ttcaacggga aacgtcgagg ccgcgattaa attccaacat ggatgctgat | 60 |
| ttatatgggt ataaatgggc tcgcgataat gtcgggcaat caggtgcgac aatctatcgc | 120 |
| ttgtatggga agcccgatgc gccagagttg tttctgaaac atggcaaagg tagcgttgcc | 180 |
| aatgatgtta cagatgagat ggtcagacta aactggctga cggaatttat gcctcttccg | 240 |
| accatcaagc attttatccg tactcctgat gatgcatggt tactcaccac tgcgatcccc | 300 |
| ggaaaaacag cattccaggt attagaagaa tatcctgatt caggtgaaaa tattgttgat | 360 |

| | |
|---|---|
| gcgctggcag tgttcctgcg ccggttgcat tcgattcctg tttgtaattg tccttttaac | 420 |
| agcgatcgcg tatttcgtct cgctcaggcg caatcacgaa tgaataacgg tttggttgat | 480 |
| gcgagtgatt ttgatgacga gcgtaatggc tggcctgttg aacaagtctg gaaagaaatg | 540 |
| cataaacttt tgccattctc accggattca gtcgtcactc atggtgattt ctcacttgat | 600 |
| aaccttattt ttgacgaggg gaaattaata ggttgtattg atgttggacg agtcggaatc | 660 |
| gcagaccgat accaggatct tgccatccta tggaactgcc tcggtgagtt ttctccttca | 720 |
| ttacagaaac ggcttttttca aaatatggt attgataatc ctgatatgaa taaattgcag | 780 |
| tttcatttga tgctcgatga gttttttctaa | 810 |

<210> SEQ ID NO 12
<211> LENGTH: 2369
<212> TYPE: DNA
<213> ORGANISM: pYUB12

<400> SEQUENCE: 12

| | |
|---|---|
| ggggcctgta acggcacaac gaaccgtgca acgagagtgg ccacggatgc caccacaagc | 60 |
| actacaacgg agttcgccac gtacatcacc acaaccaccg attctggcgg tgagctccac | 120 |
| gatattcagc ggaaatggct tggtatcgac caagattcgt agaacccgt ctcgtctggc | 180 |
| tggtattcaa aacggacgca acgaaacacg caacgagaca ggcatggccc aaaccagaaa | 240 |
| actagcgtct accaggactt ttacctgtcc gacccgttgc aacggaaccc cccacggaac | 300 |
| ccccgcgaca cccgctcccc aattgcgtta gaacagcggt ggattgtcgg cttcgttgtg | 360 |
| ggccttttga gccgcttcct gttctgccgc acgctctttc ctcgcccgat agccgagtcg | 420 |
| cttaacggtg tccagatgca gcccgaaatg tttggccgtt tgcggccaag agtggccctc | 480 |
| gtcgtcgtga taggcgcgga tgcgttcgcg gcgtgcagcc tgctcggcga gccactcgct | 540 |
| gcgttcctgc gccacgagcc ggacgacgtg gcgttcggat agtccggtga ttcgagcgcc | 600 |
| ttcggcggcg gtcacgcgcc gcttttttgcg gacagtcggc tgccggttgt agccgtcgct | 660 |
| gtagccgtcg ctgtagccgt cgctcatagc aatgcctcca tggctgacgc ggactttgcg | 720 |
| cgccgcgcaa ctgtgctcgc cgccgtgcgc gctgctgcgc cttccgcga gatggccgac | 780 |
| tggcgcgcac tgagtgtggc ctcgtagacc acgatcccgt ccgcccaaat gcgcgacttg | 840 |
| gttgtgatcc aacgccaaat gctgttggcg atggcgcgga cctcgctgtc cggtagcggt | 900 |
| ccgggacaca cgtcgttgca cgggaattcg gcgtttcgcg cgtggcactc ggcatagatc | 960 |
| gcgcggccga gtccgtccac gttccgggtc ggcaggtaga tccgcatgag ggcgggacga | 1020 |
| taggcccaca acctgacgga atcgaacagt gcgcaattcc gccctagcgg cgtcggagcc | 1080 |
| gctttgtacg tggtctgctg acgccagcgc ggcggtggca tgttcgcgcc gagctcggcc | 1140 |
| tcgatgtggc tgagtgtgta gagatctgag tggagccatt ccgtttccca ggcgatgtgg | 1200 |
| ccggggtttt tggtcatgag gcctgagtaa ctgcggtcgc cgtcgacggc gcgccgaagg | 1260 |
| ccttcggcgc acgccgccat gtatgcgagc ggcttacgcc gcgcgtattc ggtgcgtgga | 1320 |
| acagggcgt tgagtgccca cactgcgtgt gcgtggccgt tggcgcgatt gcccacgatc | 1380 |
| gcgttgggca gcgatggga ccccggggcg ctgagcgctc ggagcgctgc gtctggatgg | 1440 |
| tctacgtcca cgaccagcag gtttgccagc gctgttgggt tcgcctcgat gtaccggcgg | 1500 |
| cctaggccg acgcgcggct ttggcggtag atcccctcga gcagatcgtc gcttgccagc | 1560 |
| ggccagtacg gcagccagag ctgctcaaat tcgtcggcga cgtggctcac gcttggtagt | 1620 |
| agaccacgat taatcaccgg tgtatggtcc gacacgagct ccaagtcaga tatttcgctg | 1680 |

| | |
|---|---|
| aggggccacc ccacaactgc acactccccc gctctcccgt cgagccctga tgatgaaaca | 1740 |
| ccagcgacag ccgagcaccc ccaaccacct gtaccaacca ggaggaacac atgcgtcgtt | 1800 |
| tcgaggacgt ttccgggccg ctaagagccg ctgtggcggc cgtacacgcc gccttagacc | 1860 |
| cgttagaccc cctgccgcct gaatgcgcgg gtacagccca cacagcaccc gaacttacgg | 1920 |
| agctggtggg ctcacctggc tttatggcgt acgaatcggc tgtgtgcgac ctgtttgggcg | 1980 |
| aggtgagata cgcgctactc acgctggcaa gggcgacaca gccgcccac cgagcccgca | 2040 |
| cggccgcgcg cggtgtcaac aaccgggtga gtcgtgcaca ccagcaggtg ttcgaggctt | 2100 |
| ggctcgaagt gcaggacatc gtggcgaacg ccgcccgatg agccgcgcct tacgctggct | 2160 |
| gccagccgtt cgcgggctgg ttggtgcagc gcgtcgagcg gttagaggcc ctgcggtgtt | 2220 |
| ccaccaccgc aggcctcgcc ctttttaagg ctgaatttgc ttgtctccga atccaactgg | 2280 |
| cttgtccaag ggtgtatcta cgcttagtcc aaagttcaaa cgaggggatt acacatgacc | 2340 |
| aacttcgata acgttctcgg ctcgatctg | 2369 |

<210> SEQ ID NO 13
<211> LENGTH: 56
<212> TYPE: DNA
<213> ORGANISM: Artificial Sequence
<220> FEATURE:
<223> OTHER INFORMATION: Theophylline riboswitch

<400> SEQUENCE: 13

| | |
|---|---|
| ggtgatacca gcatcgtctt gatgccctgg cagcaccctg ctaaggaggc aacaag | 56 |

<210> SEQ ID NO 14
<211> LENGTH: 4022
<212> TYPE: DNA
<213> ORGANISM: Artificial Sequence
<220> FEATURE:
<223> OTHER INFORMATION: DNA cassette for targets RdRp1, RdRp2, N
    protein and E protein

<400> SEQUENCE: 14

| | |
|---|---|
| gttaacacta gttgattagc taagcagaag gccatcctga cggatggcct ttttgcgttt | 60 |
| aatactgttt aaacctctag aggtgtggta gccgatgccg gtgttggcgc cggtgaccac | 120 |
| aacgacgcgc ccgctttgat cggggacgtc tgcggccgac catttacggg tcttgttgtc | 180 |
| gttggcggtc atgggccgaa catactcacc cggatcggag ggccgaggac aaggtcgaac | 240 |
| gaggggcatg acccggtgcg gggcttcttg cactcggcat aggcgagtgc taagaataac | 300 |
| gttggcactc gcgaccggtg agtgctaggt cgggacggtg aggccaggcc cgtcgtcgca | 360 |
| gcgagtggca gcgaggacaa cttgagccgt ccgtcgcggg cactgcgccc ggccagcgta | 420 |
| agtagcgggg ttgccgtcac ccggtgaccc ccgtttcatc cccgatccgc atgcggatcc | 480 |
| ctgcagagta ctctcttatt gtaacagctt taagggccaa ttctgctgtc aaattacaga | 540 |
| ataatgagct tagtcctgtt gcactacgac agatgtcttg tgctgccggt actacacaaa | 600 |
| ctgcttgcac tgatgacaat gcgttagctt actacaacac aacaaaggga ggtaggtttg | 660 |
| tacttgcact gttatccgat ttacaggatt tgaaatgggc tagtactcag ctggaaatgc | 720 |
| tggtattgtt ggtgtactga cattagataa tcaagatctc aatggtaact ggtatgattt | 780 |
| cggtgatttc atacaaacca cgccaggtag tggagttcct gttgtagatt cttattattc | 840 |
| attgttaatg cctatattaa ccttgaccag ggctttaact gcagagtcac atgttgacac | 900 |
| tgacttaaca aagccttaca cagctggata tctttagatt tcatctaaac gaacaaacta | 960 |

```
aaatgtctga taatggaccc caaaatcagc gaaatgcacc ccgcattacg tttggtggac    1020
cctcagattc aactggcagt aaccagaatg gagaacgcag tggggcgcga tcaaaacaac    1080
gtcggcccca aggtttaccc aataatactg cgtcttggtt caccgctctc actcaacatg    1140
gcaaggaaga ccttaaattc cctcgaggac aaggcgttcc aattaacacc aatagcagtc    1200
cagatgacca aattggctac taccgaagag ctaccagacg aattcgtggt ggtgacggta    1260
aaatgaaaga tctcagtcca agatggtatt tctactacct aggaactggg ccagaagctg    1320
gacttcccta tggtgctaac aaagacggca tcatatgggt tgcaactgag ggagccttga    1380
atacaccaaa agatcacatt ggcacccgca atcctgctaa caatgctgca atcgtgctac    1440
aacttcctca aggaacaaca ttgccaaaag gcttctacgc agaagggagc agaggcggca    1500
gtcaagcctc ttctcgttcc tcatcacgta gtcgcaacag ttcaagaaat tcaactccag    1560
gcagcagtag gggaacttct cctgctagaa tggctggcaa tggcggtgat gctgctcttg    1620
ctttgctgct gcttgacaga ttgaaccagc ttgagagcaa aatgtctggt aaaggccaac    1680
aacaacaagg ccaaactgtc actaagaaat ctgctgctga ggcttctaag aagcctcggc    1740
aaaaacgtac tgccactaaa gcatacaatg taacacaagc tttcggcaga cgtggtccag    1800
aacaaaccca aggaaatttt ggggaccagg aactaatcag acaaggaact gattacaaac    1860
attggccgca aattgcacaa tttgccccca gcgcttcagc gttcttcgga atgtcgcgca    1920
ttggcatgga agtcacacct tcgggaacgt ggttgaccta cacaggtgcc atcaaattgg    1980
atgacaaaga tccaaatttc aaagatcaag tcattttgct gaataagcat atgatatcta    2040
cgtactcatt cgtttcggaa gagacaggta cgttaatagt taatagcgta cttctttttc    2100
ttgctttcgt ggtattcttg ctagttacac tagccatcct tactgcgctt cgattgtgtg    2160
cgtactgctg caatattgtt aacgtgagtc ttgtaaaacc ttcttttttac gtttactctc    2220 gtgttaaaaa tctgaattct tctagagttc ctgatcttct ggtctaatac gtaaagctta    2280
ggaaggaatg tacatatggc gaccgagggc gcgcgcaaca tcggccagtc ggccccggag    2340
ggcaaggtgc agatggactg cccgtcgcgc cacaacttcg acccggagtg cgagaaggcg    2400
tttgtggagc acatccacct tgagctggcc tcgtcgtacc acgcatggtc gatgtgggcc    2460
ttctacgccc gcgactgcaa ggccgccgtg ggcatgaccc gcctgtgcga gtgggcctcg    2520
cacgtctcgg cccagcgcgc cgccgcatg gccgcctacg tgctgacccg cggcggccac    2580
gtggactaca aggagatccc ggccccgaag aagcagggct gggacaactt cgaggacgcc    2640
ttctcgcact gcgtggcgaa caagaagcgc atcctgacct cgctccagtc gctgtaccag    2700
tgctgccagt cgaaggacgc ccactgctcg aacttcatcc agaccgacat gatggacgag    2760
gtgatcgcgt ggaacaagtt tctgtcggac tgcctgtcga acctgcactg catcggctcg    2820
cagggcatgg accgtgggt gttcgaccgc tggctggccc gcatcgtgat gtcgaagttc    2880
aagcacccga agatcccgtc gctctcgacc tcggacctag agtcgaacat cccgaacgag    2940
ctgttcgacg ccgagggcga catggtgcgc gccatcaaga agctggacta caaggaccat    3000
gacggtgact ataaagatca cgatatagat tacaaggatg acgatgacaa gtgacttaag    3060
ggtaccggtg ataccagcat cgtccttgatg ccctggcagc accctgctaa ggaggcaaca    3120
agatgcatac catctaccgc atcgagaaga aggagaacta cgtggtgctg gacaagggct    3180
tcctgcacga ccgcgagctg tcgtggcagg ctaagggcct gctggccttc atgctgtcga    3240
tgccgaacga ctgggtgttc aacatgaagg acctccagaa ccgctcgaag aacggtcgcg    3300
```

```
acgccaccta ccgcattatg aaggagctga tcgaggccgg ctacgtgacc cgcgtggaga    3360
accgcgacgg cggcaagttc ggcaaggtgg agtacgtggt ccacgaggtg aagcagtcgc    3420
cgcacaccga gtcgccggac accgtgccgc cctgcaccga gaacccgtac cccggcaacc    3480
cgtaccccgg caacccgtac ccggagaacc cgccgctgct gaacaacaac aacaccaact    3540
acaagaacac caacaacgac gacgacaaca aggaccgccc gaagaccaac tcgctgaacg    3600
cctttcgctt ctacgaggag aacttccagc cgaccctgtc gtcggtggac atcgagatcc    3660
tgaactactg gctggaccgc ttcccggagg agatcgtgct gtgcgccatg cggaaggccc    3720
tagagcagaa cgtgcgctcg atcaagtaca tcgaccgcat ccttgccaac tgggagatgc    3780
agaaggtgca gacccttgag gacgtggccc gcctcgaccg ccagtacgag ctggagaagc    3840
aggcccgcca aagcgcggc ggcgtggtga acggctcggt ccaccagcac cgcggctcgg    3900
```

```
agggccaatt ctgctgtcaa attacagaat aatgagctta gtcctgttgc actacgacag    1320
atgtcttgtg ctgccggtac tacacaaact gcttgcactg atgacaatgc gttagcttac    1380
tacaacacaa caaagggagg taggtttgta cttgcactgt tatccgatttt acaggatttg    1440 aaatgggcta gtactcagct ggaaatgctg gtattgttgg tgtactgaca ttagataatc    1500
aagatctcaa tggtaactgg tatgatttcg gtgatttcat acaaaccacg ccaggtagtg    1560
gagttcctgt tgtagattct tattattcat tgttaatgcc tatattaacc ttgaccaggg    1620
ctttaactgc agagtcacat gttgacactg acttaacaaa gccttacaca gctggatatc    1680
tttagatttc atctaaacga acaaactaaa atgtctgata atggacccca aaatcagcga    1740
aatgcacccc gcattacgtt tggtggaccc tcagattcaa ctggcagtaa ccagaatgga    1800
gaacgcagtg gggcgcgatc aaaacaacgt cggccccaag gtttacccaa taatactgcg    1860
tcttggttca ccgctctcac tcaacatggc aaggaagacc ttaaattccc tcgaggacaa    1920
ggcgttccaa ttaacaccaa tagcagtcca gatgaccaaa ttggctacta ccgaagagct    1980
accagacgaa ttcgtggtgg tgacggtaaa atgaaagatc tcagtccaag atggtatttc    2040
tactacctag gaactgggcc agaagctgga cttccctatg gtgctaacaa agacggcatc    2100
atatgggttg caactgaggg agccttgaat acaccaaaag atcacattgg cacccgcaat    2160
cctgctaaca atgctgcaat cgtgctacaa cttcctcaag gaacaacatt gccaaaaggc    2220
ttctacgcag aagggagcag aggcggcagt caagcctctt ctcgttcctc atcacgtagt    2280
cgcaacagtt caagaaattc aactccaggc agcagtaggg gaacttctcc tgctagaatg    2340
gctggcaatg gcggtgatgc tgctcttgct ttgctgctgc ttgacagatt gaaccagctt    2400
gagagcaaaa tgtctggtaa aggccaacaa caacaaggcc aaactgtcac taagaaatct    2460
gctgctgagg cttctaagaa gcctcggcaa aaacgtactg ccactaaagc atacaatgta    2520
acacaagctt tcggcagacg tggtccagaa caaacccaag gaaattttgg ggaccaggaa    2580
ctaatcagac aaggaactga ttacaaacat tggccgcaaa ttgcacaatt gcccccagc    2640 gcttcagcgt tcttcggaat gtcgcgcatt ggcatggaag tcacaccttc gggaacgtgg    2700
ttgacctaca caggtgccat caaattggat gacaaagatc caaatttcaa agatcaagtc    2760
attttgctga ataagcatat gatatctacg tactcattcg tttcggaaga gacaggtacg    2820
ttaatagtta atagcgtact tcttttttctt gctttcgtgg tattcttgct agttacacta    2880
gccatcctta ctgcgcttcg attgtgtgcg tactgctgca atattgttaa cgtgagtctt    2940
gtaaaacctt cttttttacgt ttactctcgt gttaaaaatc tgaattcttc tagagttcct    3000
gatcttctgg tctaatacgt aaagcttagg aaggaatgta catatggcga ccgagggcgc    3060
gcgcaacatc ggccagtcgg ccccggaggg caaggtgcag atggactgcc cgtcgcgcca    3120
caacttcgac ccggagtgcg agaaggcgtt tgtggagcac atccaccttg agctggcctc    3180
gtcgtaccac gcatggtcga tgtgggcctt ctacgcccgc gactgcaagg ccgccgtggg    3240
catgacccgc ctgtgcgagt gggcctcgca cgtctcggcc cagcgcgccc gccgcatggc    3300
cgcctacgtg ctgacccgcg cggccacgt ggactacaag gagatcccgg ccccgaagaa    3360
gcagggctgg gacaacttcg aggacgcctt ctcgcactgc gtggcgaaca agaagcgcat    3420
cctgacctcg ctccagtcgc tgtaccagtg ctgccagtcg aaggacgccc actgctcgaa    3480
cttcatccag accgacatga tggacgaggt gatcgcgtgg aacaagtttc tgtcggactg    3540
cctgtcgaac ctgcactgca tcggctcgca gggcatggga ccgtgggtgt tcgaccgctg    3600
gctggcccgc atcgtgatgt cgaagttcaa gcacccgaag atcccgtcgc tctcgacctc    3660
```

```
ggacctagag tcgaacatcc cgaacgagct gttcgacgcc gagggcgaca tggtgcgcgc    3720
catcaagaag ctggactaca aggaccatga cggtgactat aaagatcacg atatagatta    3780
caaggatgac gatgacaagt gacttaaggg taccggtgat accagcatcg tcttgatgcc    3840
ctggcagcac cctgctaagg aggcaacaag atgcatacca tctaccgcat cgagaagaag    3900
gagaactacg tggtgctgga caagggcttc ctgcacgacc gcgagctgtc gtggcaggct    3960
aagggcctgc tggccttcat gctgtcgatg ccgaacgact gggtgttcaa catgaaggac    4020
ctccagaacc gctcgaagaa cggtcgcgac gccacctacc gcattatgaa ggagctgatc    4080
gaggccggct acgtgacccg cgtggagaac cgcgacggcg gcaagttcgg caaggtggag    4140
tacgtggtcc acgaggtgaa gcagtcgccg cacaccgagt cgccggacac cgtgccgccc    4200
tgcaccgaga cccgtacccc cggcaacccg taccccggca cccgtaccc ggagaacccg    4260 ccgctgctga caacaacaa caccaactac aagaacacca caacgacga cgacaacaag    4320 gaccgcccga agaccaactc gctgaacgcc tttcgcttct acgaggagaa cttccagccg    4380
accctgtcgt cggtggacat cgagatcctg aactactggc tggaccgctt cccggaggag    4440
atcgtgctgt gcgccatgcg gaaggcccta gagcagaacg tgcgctcgat caagtacatc    4500
gaccgcatcc ttgccaactg ggagatgcag aaggtgcaga cccttgagga cgtggcccgc    4560
ctcgaccgcc agtacgagct ggagaagcag gcccgccaga agcgcggcgg cgtggtgaac    4620
ggctcggtcc accagcaccg cggctcggac ggtcgctcga cgaaggagga cgagcgcatc    4680
tcgcactacg agccgggcaa gtgggacgac gtggacatct cgctggacgg cctgctgcac    4740
catcaccacc atcactgaac gcgtatcgat                                    4770
```

<210> SEQ ID NO 16
<211> LENGTH: 3554
<212> TYPE: RNA
<213> ORGANISM: Artificial Sequence
<220> FEATURE:
<223> OTHER INFORMATION: RNA expression cassette for targets RdRp1,
      RdRp2, N protein and E protein

<400> SEQUENCE: 16

```
gcaugcggau cccugcagag uacucucuua uuguaacagc uuuaagggcc aauucugcug     60
ucaaauuaca gaauaaugag cuuaguccug uugcacuacg acagaugucu ugucugccg    120 guacuacaca aacugcuugc acugaugaca augcguuagc uuacuacaac acaacaaagg    180
gagguagguu uguacuugca cuguuauccg auuuacagga uuugaaaugg gcuaguacuc    240
agcuggaaau gcugguauug uuggguacu gacauuagau aaucaagauc ucaaugguaa    300
cugguaugau uucggugauu ucauacaaac cacgccaggu aguggaguuc uguuugaaga    360
uucuuauuau ucauuguuaa ugccuauauu aaccuugacc agggcuuuaa cugcagaguc    420
acauguugac acugacuuaa caaagccuua cacagcugga uaucuuuaga uuucaucuaa    480
acgaacaaac uaaaaugucu gauaauggac cccaaaauca gcgaaaugca ccccgcauua    540
cguuuggugg acccucagau ucaacuggca guaaccagaa uggagaacgc agugggcgc     600 gaucaaaaca cgucggccc caagguuac ccaauaauac ugcgucuugg ucaccgcuc      660 ucacucaaca ugguaaggaa gaccuuaaau ucccucgagg acaaggcguu ccaauuaaca    720
ccaauagcag uccagaugac caaauuggcu acuaccgaag agcuaccaga cgaauucgug    780 guggugacg uaaaaugaaa gaucucaguc caagaugua uucuacuac cuaggaacug    840 ggccagaagc uggacuuccc uaugguguga caaaagacgg caucauaugg guugcaacug    900
```

-continued

```
agggagccuu gaauacacca aaagaucaca uuggcacccg caauccugcu aacaaugcug      960
caaucgugcu acaacuuccu caaggaacaa cauugccaaa aggcuucuac gcagaaggga     1020
gcagaggcgg cagucaagcc ucuucucguu ccucaucacg uagucgcaac aguucaagaa     1080
auucaacucc aggcagcagu aggggaacuu ccccugcuag aauggcuggc aauggcggug     1140
augcugcucu ugcuuugcug cugcuugaca gauugaacca gcuugagagc aaaaugucug     1200
guaaaggcca acaacaacaa ggccaaacug ucacuaagaa aucugcugcu gaggcuucua     1260
agaagccucg gcaaaaacgu acugccacua aagcauacaa uguaacacaa gcuuucggca     1320 gacggguggucc agaacaaacc caaggaaauu uggggacca ggaacuaauc agacaaggaa     1380
cugauuacaa acauuggccg caaauugcac aauuugcccc cagcgcuuca gcguucuucg     1440
gaaugucgcg cauuggcaug gaagucacac cuucgggaac ugguugacc uacacaggug     1500 ccaucaaauu ggaugacaaa gauccaaauu ucaaagauca agucauuuug cugaauaagc     1560
auaugauauc uacguacuca uucguuucgg aagagacagg uacguuaaua guuaauagcg     1620
uacuucuuuu ucuugcuuuc gugguauucu ugcuaguuac acuagccauc cuuacugcgc     1680
uucgauugug ugcguacugc ugcaauauug uuaacgugag cuuguaaaaa ccuucuuuuu     1740
acguuuacuc ucguguuaaa aaucugaauu cuucuagagu uccugaucuu cuggucuaau     1800
acguaaagcu uaggaaggaa uguacauaug gcgaccgagg gcgcgcgcaa caucggccag     1860
ucggccccgg agggcaaggu gcagauggac ugcccgucgc gccacaacuu cgacccggag     1920
ugcgagaagg cguuugugga gcacauccac cuugagcugg ccucgucgua ccacgcaugg     1980
ucgauguggg ccuucuacgc ccgcgacugc aaggccgccg ugggcaugac ccgccugugc     2040
gagugggccu cgcacgucuc ggcccagcgc gcccgccgca uggccgccua cgucugaccc     2100
cgcggcggcc acguggacua caaggagauc ccggcccga agaagcaggg cuggacaac      2160 uucgaggacg ccuucucgca cugcguggcg aacaagaagc gcauccugac cucgcuccag     2220
ucgcuguacc agugcugcca gucgaaggac gcccacugcu cgaacuucau ccagaccgac     2280
augauggacg aggugaucgc guggaacaag uuucugucgg acugccuguc gaaccugcac     2340
ugcaucggcu cgcagggcau gggaccgugg guguucgacc gcuggcuggc ccgcaucgug     2400
augucgaagu ucaagcaccc gaagaucccg ucgcucucga ccucggaccu agagucgaac     2460 auccccgaacg agcuguucga cgccgagggc gacaugguc gcgccaucaa gaagcuggac     2520
uacaaggacc augacgguga cuauaaagau cacgauauag auuacaagga ugacgaugac     2580
aagugacuua agggguaccgg ugauaccagc aucgucuuga ugcccuggca gcacccugcu     2640
aaggaggcaa caagaugcau accaucuacc gcaucgagaa gaaggagaac uacguggugc     2700
uggacaaggg cuuccugcac gaccgcgagc ugucguggca ggcuaagggc cugcuggccu     2760
ucaugcuguc gaugccgaac gacugggugu caacaugaa ggaccuccag aaccgcucga     2820
agaacggucg cgacgccacc uaccgcauua ugaaggagcu gaucgaggcc ggcuacguga     2880
cccgcgugga gaaccgcgac ggcggcaagu cggcaaggu ggaguacgug guccacgagg     2940
ugaagcaguc gccgcacacc gagucgccgg acaccgugcc gcccugcacc gagaacccgu     3000
accccggcaa cccguacccc ggcaacccgu acccggagaa cccgccgcug cugaacaaca     3060
acaacaccaa cuacaagaac accaacaacg acgacgacaa caaggaccgc ccgaagacca     3120
acucgcugaa cgccuuucgc uucuacgagg agaacuucca gccgacccug ucgucggugg     3180
acaucgagau ccugaacuac uggcuggacc gcuucccgga ggagaucgug cugugcgcca     3240
```

-continued

```
ugcggaaggc ccuagagcag aacgugcgcu cgaucaagua caucgaccgc auccuugcca     3300
acugggagau gcagaaggug cagacccuug aggacguggc ccgccucgac cgccaguacg     3360
agcuggagaa gcaggcccgc cagaagcgcg gcggcguggu gaacggcucg guccaccagc     3420
accgcggcuc ggacgucgcu cgacgaagg  aggacgagcg caucucgcac uacgagccgg     3480
gcaaguggga cgacguggac aucucgcugg acggccugcu gcaccaucac caccaucacu     3540
gaacgcguau cgau                                                       3554
```

<210> SEQ ID NO 17
<211> LENGTH: 4302
<212> TYPE: RNA
<213> ORGANISM: Artificial Sequence
<220> FEATURE:
<223> OTHER INFORMATION: RNA expression cassette for targets Spike
      protein, ORF1ab 5' region, RdRp1, RdRp2, N protein and E protein

<400> SEQUENCE: 17

```
gcaugcggau cucgcacacuu gaacagcccu auguguucau caaacguucg gaugcucgaa      60
cugcaccuca uggucauguu augguugagc ugguagcaga acucgaaggc auucaguacg     120
gucguagugg ugacacacuu ggugugccuug ucccucaugu gggcgaaaua ccaguggcuu    180
accgcaaggu ucuucuucgu aagaacggua auaaggagc ugguggccau aguuacggcg     240
ccgaucuaaa gucauuugac uuaggcgacg agcuuggcac ugauccuuau gaagauuuuc     300
aagaaaacug gaacacuaaa cauagcagug uguuacccg ugaaucaug cgugagcuua      360
acggagggc auacacucgc uaugucgaua acaacuucug uggcccugau ggcuacaagc      420
uuaaauugau ugccaaccaa uuuaauagug cuauuggcaa aauucaagac ucacuuucuu     480
ccacagcaag ugcacuugga aaacuucaag auguggucaa ccaaaaugca caagcuuuaa     540
acacgcuugu uaaacaacuu agcuccaauu uggugcaauu caagguguu uuaaaugaua      600
uccuuucacg ucuugacaaa guugaggcug aagugcaaau ugauaggguu gucacaggca    660
gacuucaaag uuugcagaca uaugugacuc aacaauuaau uagagcugca gaaaucagag    720
cuucugcuaa ucuugcugcu acuaaaaugu agaucgaucc cugcagagua cucucuuauu    780
guaacagcuu uaagggccaa uucugcuguc aaauuacaga uaaugagcu uaguccuguu    840
gcacuacgac agaugucuug ugcugccggu acuacacaaa cugcuugcac ugaugacaau     900
gcguuagcuu acuacaacac aacaaaggga gguagguuug uacuugcacu guuauccgau    960
uuacaggauu ugaaaugggc uaguacucag cuggaaaugc ugguauuguu ggugacuga     1020
cauuagauaa ucaagaucuc aauggguaacu gguaugauuu cggugauuuc auacaaacca    1080
cgccagguag uggaguuccu guugagauu cuuauuauuc auuguuaaug ccauauuaa      1140
ccuugaccag ggcuuuaacu gcagagcac auguugcac ugacuaaca aagccuuaca      1200
cagcuggaua ucuuuagauu caucuaaac gaacaaacua aaaugucuga uaauggaccc    1260
caaaaucagc gaaaugcacc ccgcauuacg uuuggggac ccucagauuc aacuggcagu    1320
aaccagaaug gagaacgcag uggggcgcga ucaaaacaac gucggcccca agguuuaccc    1380
aauaauacug cgucuugguu caccgcucuc acucaacaug gcaaggaaga ccuuaaauuc    1440
ccucgaggac aaggcguucc aauuaacacc aauagcaguc cagaugacca aauuggcuac    1500
uaccgaagag cuaccagacg aauucguggu ggugacggua aaaugaaaga ucucagucca    1560
agauggguauu ucuacuaccu aggaacuggg ccagaagcug gacuucccua uggugcuaac    1620
aaagacggca ucauauggu ugcaacugag ggagccuuga auacaccaaa agaucacauu    1680
```

```
ggcacccgca auccugcuaa caaugcugca aucgugcuac aacuuccuca aggaacaaca    1740
uugccaaaag gcuucuacgc agaagggagc agaggcggca gucaagccuc uucucguucc    1800
ucaucacgua gucgcaacag uucaagaaau ucaacuccag gcagcaguag gggaacuucu    1860
ccugcuagaa uggcuggcaa uggcggugau gcugcucuug cuuugcugcu gcuugacaga    1920
uugaaccagc uugagagcaa aaugucuggu aaaggccaac aacaacaagg ccaaacuguc    1980
acuaagaaau cugcucgcuga ggcuucuaag aagccucggc aaaaacguac ugccacuaaa    2040
```

-continued

| | |
|---|---|
| gacguggccc gccucgaccg ccaguacgag cuggagaagc aggcccgcca gaagcgcggc | 4140 |
| ggcguggugu acggcucggu ccaccagcac cgcggcucgg acggucgcuc gacgaaggag | 4200 |
| gacgagcgca ucucgcacua cgagccgggc aagugggacg acguggacau cucgcuggac | 4260 |
| ggccugcugc accaucacca ccaucacuga acgcguaucg au | 4302 |

<210> SEQ ID NO 18
<211> LENGTH: 3100
<212> TYPE: DNA
<213> ORGANISM: SARS-CoV-2

<400> SEQUENCE: 18

| | |
|---|---|
| attaaaggtt tataccttcc caggtaacaa accaaccaac tttcgatctc ttgtagatct | 60 |
| gttctctaaa cgaactttaa atctgtgtg gctgtcactc ggctgcatgc ttagtgcact | 120 |
| cacgcagtat aattaataac taattactgt cgttgacagg acacgagtaa ctcgtctatc | 180 |
| ttctgcaggc tgcttacggt ttcgtccgtg ttgcagccga tcatcagcac atctaggttt | 240 |
| cgtccgggtg tgaccgaaag gtaagatgga gagccttgtc cctggtttca acgagaaaac | 300 |
| acacgtccaa ctcagtttgc ctgttttaca ggttcgcgac gtgctcgtac gtggctttgg | 360 |
| agactccgtg gaggaggtct tatcagaggc acgtcaacat cttaaagatg gcacttgtgg | 420 |
| cttagtagaa gttgaaaaag gcgttttgcc tcaacttgaa cagccctatg tgttcatcaa | 480 |
| acgttcggat gctcgaactg cacctcatgg tcatgttatg gttgagctgg tagcagaact | 540 |
| cgaaggcatt cagtacggtc gtagtggtga cacttggt gtccttgtcc ctcatgtggg | 600 |
| cgaaatacca gtggcttacc gcaaggttct tcttcgtaag aacggtaata aaggagctgg | 660 |
| tggccatagt tacggcgccg atctaaagtc atttgactta ggcgacgagc ttggcactga | 720 |
| tccttatgaa gattttcaag aaaactggaa cactaaacat agcagtggtg ttacccgtga | 780 |
| actcatgcgt gagcttaacg gaggggcata cactcgctat gtcgataaca acttctgtgg | 840 |
| ccctgatggc taccctcttg agtgcattaa agaccttcta gcacgtgctg gtaaagcttc | 900 |
| atgcactttg tccgaacaac tggactttat tgacactaag aggggtgtat actgctgccg | 960 |
| tgaacatgag catgaaattg cttggtacac ggaacgttct gaaaagagct atgaattgca | 1020 |
| gacaccttt gaaattaaat tggcaaagaa atttgacacc ttcaatgggg aatgtccaaa | 1080 |
| ttttgtattt cccttaaatt ccataatcaa gactattcaa ccaagggttg aaaagaaaaa | 1140 |
| gcttgatggc tttatgggta gaattcgatc tgtctatcca gttgcgtcac caatgaatg | 1200 |
| caaccaaatg tgcctttcaa ctctcatgaa gtgtgatcat tgtggtgaaa cttcatggca | 1260 |
| gacgggcgat tttgttaaag ccacttgcga ttttgtggc actgagaatt tgactaaaga | 1320 |
| aggtgccact acttgtggtt acttacccca aaatgctgtt gttaaaattt attgtccagc | 1380 |
| atgtcacaat tcagaagtag gacctgagca tagtcttgcc gaataccata tgaatctgg | 1440 |
| cttgaaaacc attcttcgta agggtggtcg cactattgcc tttggaggct gtgtgttctc | 1500 |
| ttatgttggt tgccataaca agtgtgccta ttgggttcca cgtgctagcg ctaacatagg | 1560 |
| ttgtaaccat acaggtgttg ttggagaagg ttccgaaggt cttaatgaca accttcttga | 1620 |
| aatactccaa aaagagaaag tcaacatcaa tattgttggt gactttaaac ttaatgaaga | 1680 |
| gatcgccatt atttggcat cttttctgc ttccacaagt gcttttgtgg aaactgtgaa | 1740 |
| aggtttggat tataaagcat tcaaacaaat tgttgaatcc tgtggtaatt ttaaagttac | 1800 |
| aaaaggaaaa gctaaaaaag gtgcctggaa tattggtgaa cagaaatcaa tactgagtcc | 1860 |

```
tctttatgca tttgcatcag aggctgctcg tgttgtacga tcaattttct cccgcactct    1920
tgaaactgct caaaattctg tgcgtgtttt acagaaggcc gctataacaa tactagatgg    1980
aatttcacag tattcactga gactcattga tgctatgatg ttcacatctg atttggctac    2040
taacaatcta gttgtaatgg cctacattac aggtggtgtt gttcagttga cttcgcagtg    2100
gctaactaac atctttggca ctgtttatga aaaactcaaa cccgtccttg attggcttga    2160
agagaagttt aaggaaggtg tagagtttct tagagacggt tgggaaattg ttaaatttat    2220
ctcaacctgt gcttgtgaaa ttgtcggtgg acaaattgtc acctgtgcaa aggaaattaa    2280
ggagagtgtt cagacattct ttaagcttgt aaataaattt ttggctttgt gtgctgactc    2340
tatcattatt ggtggagcta aacttaaagc cttgaattta ggtgaaacat tgtcacgcca    2400
ctcaaaggga ttgtacagaa agtgtgttaa atccagagaa gaaactggcc tactcatgcc    2460
tctaaaagcc ccaaaagaaa ttatcttctt agagggagaa acacttccca cagaagtgtt    2520
aacagaggaa gttgtcttga aaactggtga tttacaacca ttagaacaac ctactagtga    2580
agctgttgaa gctccattgg ttggtacacc agtttgtatt aacgggctta tgttgctcga    2640
aatcaaagac acagaaaagt actgtgccct tgcacctaat atgatggtaa caaacaatac    2700
cttcacactc aaaggcggtg caccaacaaa ggttactttt ggtgatgaca ctgtgataga    2760
agtgcaaggt tacaagagtg tgaatatcac ttttgaactt gatgaaagga ttgataaagt    2820
acttaatgag aagtgctctg cctatacagt tgaactcggt acagaagtaa atgagttcgc    2880
ctgtgttgtg gcagatgctg tcataaaaac tttgcaacca gtatctgaat tacttacacc    2940
actgggcatt gatttagatg agtggagtat ggctacatac tacttatttg atgagtctgg    3000
tgagtttaaa ttggcttcac atatgtattg ttctttctac cctccagatg aggatgaaga    3060
agaaggtgat tgtgaagaag aagagtttga gccatcaact                          3100
```

<210> SEQ ID NO 19
<211> LENGTH: 3070
<212> TYPE: DNA
<213> ORGANISM: SARS-CoV-2

<400> SEQUENCE: 19

```
cttcacactc aaaggcggtg caccaacaaa ggttactttt ggtgatgaca ctgtgataga     60
agtgcaaggt tacaagagtg tgaatatcac ttttgaactt gatgaaagga ttgataaagt    120
acttaatgag aagtgctctg cctatacagt tgaactcggt acagaagtaa atgagttcgc    180
ctgtgttgtg gcagatgctg tcataaaaac tttgcaacca gtatctgaat tacttacacc    240
actgggcatt gatttagatg agtggagtat ggctacatac tacttatttg atgagtctgg    300
tgagtttaaa ttggcttcac atatgtattg ttctttctac cctccagatg aggatgaaga    360
agaaggtgat tgtgaagaag aagagtttga gccatcaact caatatgagt atggtactga    420
agatgattac caaggtaaac ctttggaatt tggtgccact tctgctgctc ttcaaccctga   480
agaagagcaa gaagaagatt ggttagatga tgatagtcaa caaactgttg gtcaacaaga    540
cggcagtgag gacaatcaga caactactat tcaaacaatt gttgaggttc aacctcaatt    600
agagatggaa cttaccagt tgttcagac tattgaagtg aatagtttta gtggttattt      660
aaaacttact gacaatgtat acattaaaaa tgcagacatt gtggaagaag ctaaaaaggt    720
aaaaccaaca gtggttgtta atgcagccaa tgtttacctt aaacatggag gaggtgttgc    780
aggagcctta aataaggcta ctaacaatgc catgcaagtt gaatctgatg attacatagc    840
tactaatgga ccacttaaag tgggtggtag ttgtgtttta agcggacaca atcttgctaa    900
```

```
acactgtctt catgttgtcg gcccaaatgt taacaaaggt gaagacattc aacttcttaa    960
gagtgcttat gaaaatttta atcagcacga agttctactt gcaccattat tatcagctgg   1020
tattttggt gctgaccta tacattcttt aagagtttgt gtagatactg ttcgcacaaa   1080
tgtctactta gctgtctttg ataaaaatct ctatgacaaa cttgtttcaa gcttttgga   1140
aatgaagagt gaaaagcaag ttgaacaaaa gatcgctgag attcctaaag aggaagttaa   1200
gccatttata actgaaagta aaccttcagt tgaacagaga aaacaagatg ataagaaaat   1260
caaagcttgt gttgaagaag ttacaacaac tctggaagaa actaagttcc tcacagaaaa   1320
cttgttactt tatattgaca ttaatggcaa tcttcatcca gattctgcca ctcttgttag   1380
tgacattgac atcactttct aaagaaaga tgctccatat atagtgggtg atgttgttca   1440
agagggtgtt ttaactgctg tggttatacc tactaaaaag gctggtggca ctactgaaat   1500
gctagcgaaa gctttgagaa aagtgccaac agacaattat ataaccactt acccgggtca   1560
gggtttaaat ggttacactg tagaggaggc aaagacagtg cttaaaaagt gtaaaagtgc   1620
cttttacatt ctaccatcta ttatctctaa tgagaagcaa gaaattcttg gaactgtttc   1680
ttggaatttg cgagaaatgc ttgcacatgc agaagaaaca cgcaaattaa tgcctgtctg   1740
tgtggaaact aaagccatag tttcaactat acagcgtaaa tataagggta ttaaaataca   1800
agagggtgtg gttgattatg gtgctagatt ttacttttac accagtaaaa caactgtagc   1860
gtcacttatc aacacactta acgatctaaa tgaaactctt gttacaatgc cacttggcta   1920
tgtaacacat ggcttaaatt tggaagaagc tgctcggtat atgagatctc tcaaagtgcc   1980
agctacagtt tctgtttctt cacctgatgc tgttacagcg tataatggtt atcttacttc   2040
ttcttctaaa acacctgaag aacattttat tgaaaccatc tcacttgctg gttcctataa   2100
agattggtcc tattctggac aatctacaca actaggtata gaatttctta agagaggtga   2160
taaaagtgta tattcacta gtaatcctac cacattccac ctagatggtg aagttatcac   2220
ctttgacaat cttaagacac ttcttttctt gagagaagtg aggactatta aggtgtttac   2280
aacagtagac aacattaacc tccacacgca agttgtggac atgtcaatga catatggaca   2340
acagtttggt ccaacttatt tggatggagc tgatgttact aaaataaaac ctcataattc   2400
acatgaaggt aaaacatttt atgttttacc taatgatgac actctacgtg ttgaggcttt   2460
tgagtactac cacacaactg atcctagttt tctgggtagg tacatgtcag cattaaatca   2520
cactaaaaag tggaaatacc cacaagttaa tggtttaact tctattaaat gggcagataa   2580
caactgttat cttgccactg cattgttaac actccaacaa atagagttga gtttaatcc   2640
acctgctcta caagatgctt attacagagc aagggctggt gaagctgcta acttttgtgc   2700
acttatctta gcctactgta ataagacagt aggtgagtta ggtgatgtta gagaaacaat   2760
gagttacttg tttcaacatg ccaatttaga ttcttgcaaa agagtcttga acgtggtgtg   2820
taaaacttgt ggacaacagc agacaaccct taagggtgta gaagctgtta tgtacatggg   2880
cacactttct tatgaacaat taagaaagg tgttcagata ccttgtacgt gtggtaaaca   2940
agctacaaaa tatctagtac aacaggagtc acctttttgtt atgatgtcag caccacctgc   3000
tcagtatgaa cttaagcatg gtacatttac ttgtgctagt gagtacactg gtaattacca   3060
gtgtggtcac                                                           3070
```

<210> SEQ ID NO 20
<211> LENGTH: 3156
<212> TYPE: DNA

<210> ORGANISM: SARS-CoV-2

<400> SEQUENCE: 20

```
acttatctta gcctactgta ataagacagt aggtgagtta ggtgatgtta gagaaacaat      60
gagttacttg tttcaacatg ccaatttaga ttcttgcaaa agagtcttga acgtggtgtg     120
taaaacttgt ggacaacagc agacaaccct aagggtgta gaagctgtta tgtacatggg     180
cacactttct tatgaacaat ttaagaaagg tgttcagata ccttgtacgt gtggtaaaca     240
agctacaaaa tatctagtac aacaggagtc accttttgtt atgatgtcag caccacctgc     300
tcagtatgaa cttaagcatg gtacatttac ttgtgctagt gagtacactg gtaattacca     360
gtgtggtcac tataaacata aacttctaa agaaactttg tattgcatag acggtgcttt     420
acttacaaag tcctcagaat acaaaggtcc tattacggat gttttctaca agaaaacag     480
ttacacaaca accataaaac cagttactta taaattggat ggtgttgttt gtacagaaat     540
tgaccctaag ttggacaatt attataagaa agacaattct tatttcacag agcaaccaat     600
tgatcttgta ccaaaccaac catatccaaa cgcaagcttc gataatttta gtttgtatg     660
tgataatatc aaatttgctg atgatttaaa ccagttaact ggttataaga aacctgcttc     720
aagagagctt aaagttacat ttttccctga cttaaatggt gatgtggtgg ctattgatta     780
taaacactac acaccctctt ttaagaaagg agctaaattg ttacataaac ctattgtttg     840
gcatgttaac aatgcaacta ataaagccac gtataaacca ataccggt gtacgttg     900
tctttggagc acaaaaccag ttgaaacatc aaattcgttt gatgtactga agtcagagga     960
cgcgcaggga atgctaatc ttgcctgcga agatctaaaa ccagtctctg aagaagtagt    1020
ggaaaatcct accatacaga aagacgttct tgagtgtaat gtgaaaacta ccgaagttgt    1080
aggagacatt atacttaaac cagcaaataa tagtttaaaa attacagaag aggttggcca    1140
cacagatcta atggctgctt atgtagacaa ttctagtctt actattaaga aacctaatga    1200
attatctaga gtattaggtt tgaaaacct tgctactcat ggtttagctg ctgttaatag    1260
tgtcccttgg gatactatag ctaattatgc taagccttt cttaacaaag tgttagtac    1320
aactactaac atagttacac ggtgtttaaa ccgtgtttgt actaattata tgccttattt    1380
ctttactta ttgctacaat tgtgtacttt tactagaagt acaaattcta gaattaaagc    1440
atctatgccg actactatag caaagaatac tgttaagagt gtcggtaaat tttgtctaga    1500
ggcttcattt aattatttga agtcacctaa ttttctaaa ctgataaata ttataatttg    1560
gttttttacta ttaagtgtttt gcctaggttc tttaatctac tcaaccgctg ctttaggtgt    1620
tttaatgtct aatttaggca tgccttctta ctgtactggt tacagagaag gctatttgaa    1680
ctctactaat gtcactattg caacctactg tactggttct ataccttgta gtgtttgtct    1740
tagtggttta gattctttag acacctatcc ttctttagaa actatacaa ttaccattc    1800
atcttttaaa tgggatttaa ctgcttttgg cttagttgca gagtggtttt tggcatatat    1860
tctttttcact aggtttttct atgtacttgg attggctgca atcatgcaat gttttttcag    1920
ctatttgca gtacatttta ttagtaattc ttggcttatg tggttaataa ttaatcttgt    1980
acaaatggcc ccgatttcag ctatggttag aatgtacatc ttctttgcat cattttatta    2040
tgtatggaaa agttatgtgc atgttgtaga cggttgtaat tcatcaactt gtatgatgtg    2100
ttacaaacgt aatagagcaa caagagtcga atgtacaact attgttaatg gtgttagaag    2160
gtccttttat gtctatgcta atggaggtaa aggcttttgc aaactacaca attggaattg    2220
tgttaattgt gatacattct gtgctggtag tacatttatt agtgatgaag ttgcgagaga    2280
```

```
cttgtcacta cagtttaaaa gaccaataaa tcctactgac cagtcttcct acatcgttga      2340
tagtgttaca gtgaagaatg gttccatcca tctttacttt gataaagctg gtcaaaagac      2400
ttatgaaaga cattctctct ctcattttgt taacttagac aacctgagag ctaataacac      2460
taaaggttca ttgcctatta atgttatagt ttttgatggt aaatcaaaat gtgaagaatc      2520
atctgcaaaa tcagcgtctg tttactacag tcagcttatg tgtcaaccta tactgttact      2580
agatcaggca ttagtgtctg atgttggtga tagtgcggaa gttgcagtta aaatgtttga      2640
tgcttacgtt aatacgtttt catcaacttt taacgtacca atggaaaaac tcaaaacact      2700
agttgcaact gcagaagctg aacttgcaaa gaatgtgtcc ttagacaatg tcttatctac      2760 tttttatttca gcagctcggc aagggtttgt tgattcagat gtagaaacta agatgttgt      2820 tgaatgtctt aaattgtcac atcaatctga catagaagtt actggcgata gttgtaataa      2880
ctatatgctc acctataaca aagttgaaaa catgacaccc cgtgaccttg gtgcttgtat      2940
tgactgtagt gcgcgtcata ttaatgcgca ggtagcaaaa agtcacaaca ttgctttgat      3000
atggaacgtt aaagatttca tgtcattgtc tgaacaacta cgaaaacaaa tacgtagtgc      3060
tgctaaaaag aataacttac cttttaagtt gacatgtgca actactagac aagttgttaa      3120
tgttgtaaca acaaagatag cacttaaggg tggtaa                               3156

<210> SEQ ID NO 21
<211> LENGTH: 3105
<212> TYPE: DNA
<213> ORGANISM: SARS-CoV-2

<400> SEQUENCE: 21
agttgcaact gcagaagctg aacttgcaaa gaatgtgtcc ttagacaatg tcttatctac        60 tttttatttca gcagctcggc aagggtttgt tgattcagat gtagaaacta agatgttgt       120 tgaatgtctt aaattgtcac atcaatctga catagaagtt actggcgata gttgtaataa       180
ctatatgctc acctataaca aagttgaaaa catgacaccc cgtgaccttg gtgcttgtat       240
tgactgtagt gcgcgtcata ttaatgcgca ggtagcaaaa agtcacaaca ttgctttgat       300
atggaacgtt aaagatttca tgtcattgtc tgaacaacta cgaaaacaaa tacgtagtgc       360
tgctaaaaag aataacttac cttttaagtt gacatgtgca actactagac aagttgttaa       420
tgttgtaaca acaaagatag cacttaaggg tggtaaaatt gttaataatt ggttgaagca       480
gttaattaaa gttacacttg tgttcctttt tgttgctgct attttctatt aataacacc       540 tgttcatgtc atgtctaaac atactgactt ttcaagtgaa atcataggat acaaggctat       600
tgatggtggt gtcactcgtg acatagcatc tacagatact tgttttgcta caaacatgc       660 tgattttgac acatggttta gccagcgtgg tggtagttat actaatgaca aagcttgccc       720
attgattgct gcagtcataa caagagaagt gggttttgtc gtgcctggtt tgcctggcac       780
gatattacgc acaactaatg tgacttttt gcatttctta cctagagttt ttagtgcagt       840
tggtaacatc tgttacacac catcaaaact tatagagtac actgactttg caacatcagc      900
ttgtgttttg gctgctgaat gtacaatttt taaagatgct tctggtaagc cagtaccata      960
ttgttatgat accaatgtac tagaaggttc tgttgcttat gaaagtttac gccctgacac     1020
acgttatgtg ctcatggatg gctctattat tcaatttcct aacacctacc ttgaaggttc     1080
tgttagagtg gtaacaactt ttgattctga gtactgtagg cacggcactt gtgaaagatc     1140
agaagctggt gtttgtgtat ctactagtgg tagatgggta cttaacaatg attattacag     1200
```

| | |
|---|---|
| atctttacca ggagttttct gtggtgtaga tgctgtaaat ttacttacta atatgtttac | 1260 |
| accactaatt caacctattg gtgctttgga catatcagca tctatagtag ctggtggtat | 1320 |
| tgtagctatc gtagtaacat gccttgccta ctattttatg aggtttagaa gagcttttgg | 1380 |
| tgaatacagt catgtagttg cctttaatac tttactattc cttatgtcat tcactgtact | 1440 |
| ctgtttaaca ccagtttact cattcttacc tggtgtttat tctgttattt acttgtactt | 1500 |
| gacattttat cttactaatg atgtttcttt tttagcacat attcagtgga tggttatgtt | 1560 |
| cacaccttta gtacctttct ggataacaat tgcttatatc atttgtattt ccacaaagca | 1620 |
| tttctattgg ttctttagta attacctaaa gagacgtgta gtctttaatg gtgtttcctt | 1680 |
| tagtactttt gaagaagctg cgctgtgcac ctttttgtta aataaagaaa tgtatctaaa | 1740 |
| gttgcgtagt gatgtgctat tacctcttac gcaatataat agatacttag ctctttataa | 1800 |
| taagtacaag tattttagtg gagcaatgga tacaactagc tacagagaag ctgcttgttg | 1860 |
| tcatctcgca aaggctctca atgacttcag taactcaggt tctgatgttc tttaccaacc | 1920 |
| accacaaacc tctatcacct cagctgtttt gcagagtggt tttagaaaaa tggcattccc | 1980 |
| atctggtaaa gttgagggtt gtatggtaca agtaacttgt ggtacaacta cacttaacgg | 2040 |
| tctttggctt gatgacgtag tttactgtcc aagacatgtg atctgcacct ctgaagacat | 2100 |
| gcttaaccct aattatgaag atttactcat tcgtaagtct aatcataatt tcttggtaca | 2160 |
| ggctggtaat gttcaactca gggttattgg acattctatg caaaattgtg tacttaagct | 2220 |
| taaggttgat acagccaatc ctaagacacc taagtataag tttgttcgca ttcaaccagg | 2280 |
| acagactttt tcagtgttag cttgttacaa tggttcacca tctggtgttt accaatgtgc | 2340 |
| tatgaggccc aatttcacta ttaagggttc attccttaat ggttcatgtg gtagtgttgg | 2400 |
| ttttaacata gattatgact gtgtctcttt ttgttacatg caccatatgg aattaccaac | 2460 |
| tggagttcat gctggcacag acttagaagg taactttta ggaccttttg ttgacaggca | 2520 |
| aacagcacaa gcagctggta cggacacaac tattacagtt aatgtttag cttggttgta | 2580 |
| cgctgctgtt ataaatggag acaggtggtt tctcaatcga tttaccacaa ctcttaatga | 2640 |
| ctttaacctt gtggctatga gtacaatta tgaacctcta acacaagacc atgttgacat | 2700 |
| actaggacct ctttctgctc aaactggaat tgccgtttta gatatgtgtg cttcattaaa | 2760 |
| agaattactg caaaatggta tgaatggacg taccatattg ggtagtgctt tattagaaga | 2820 |
| tgaatttaca ccttttgatg ttgttagaca atgctcaggt gttactttcc aaagtgcagt | 2880 |
| gaaaagaaca atcaagggta cacaccactg gttgttactc acaattttga cttcactttt | 2940 |
| agttttagtc cagagtactc aatggtcttt gttcttttt ttgtatgaaa atgcctttt | 3000 |
| accttttgct atgggtatta ttgctatgtc tgcttttgca atgatgtttg tcaaacataa | 3060 |
| gcatgcattt ctctgtttgt ttttgttacc ttctcttgcc actgt | 3105 |

<210> SEQ ID NO 22
<211> LENGTH: 3101
<212> TYPE: DNA
<213> ORGANISM: SARS-CoV-2

<400> SEQUENCE: 22

| | |
|---|---|
| actaggacct ctttctgctc aaactggaat tgccgtttta gatatgtgtg cttcattaaa | 60 |
| agaattactg caaaatggta tgaatggacg taccatattg ggtagtgctt tattagaaga | 120 |
| tgaatttaca ccttttgatg ttgttagaca atgctcaggt gttactttcc aaagtgcagt | 180 |
| gaaaagaaca atcaagggta cacaccactg gttgttactc acaattttga cttcactttt | 240 |

```
agttttagtc cagagtactc aatggtcttt gttcttttt  ttgtatgaaa atgccttttt    300
accttttgct atgggtatta ttgctatgtc tgcttttgca atgatgtttg tcaaacataa    360
gcatgcattt ctctgtttgt ttttgttacc ttctcttgcc actgtagctt attttaatat    420
ggtctatatg cctgctagtt gggtgatgcg tattatgaca tggttggata tggttgatac    480
tagtttgtct ggttttaagc taaaagactg tgttatgtat gcatcagctg tagtgttact    540
aatccttatg acagcaagaa ctgtgtatga tgatggtgct aggagagtgt ggacacttat    600
gaatgtcttg acactcgttt ataaagttta ttatggtaat gctttagatc aagccatttc    660
catgtgggct cttataatct ctgttacttc taactactca ggtgtagtta caactgtcat    720
gtttttggcc agaggtattg tttttatgtg tgttgagtat tgccctattt tcttcataac    780
tggtaataca cttcagtgta taatgctagt ttattgtttc ttaggctatt tttgtacttg    840
ttactttggc ctcttttgtt tactcaaccg ctactttaga ctgactcttg gtgtttatga    900
ttacttagtt tctacacagg agtttagata tatgaattca cagggactac tcccacccaa    960
gaatagcata gatgccttca aactcaacat taaattgttg ggtgttggtg caaaccttg   1020 tatcaaagta gccactgtac agtctaaaat gtcagatgta aagtgcacat cagtagtctt   1080
actctcagtt ttgcaacaac tcagagtaga atcatcatct aaattgtggg ctcaatgtgt   1140
ccagttacac aatgacattc tcttagctaa agatactact gaagcctttg aaaaaatggt   1200
ttcactactt tctgttttgc tttccatgca gggtgctgta gacataaaca gctttgtga    1260 agaaatgctg gacaacaggg caaccttaca agctatagcc tcagagttta gttcccttcc   1320
atcatatgca gcttttgcta ctgctcaaga agcttatgag caggctgttg ctaatggtga   1380
ttctgaagtt gttcttaaaa agttgaagaa gtctttgaat gtggctaaat ctgaatttga   1440
ccgtgatgca gccatgcaac gtaagttgga aaagatggct gatcaagcta tgacccaaat   1500
gtataaacag gctagatctg aggacaagag ggcaaaagtt actagtgcta tgcagacaat   1560
gcttttcact atgcttagaa agttggataa tgatgcactc aacaacatta tcaacaatgc   1620
aagagatggt tgtgttccct tgaacataat acctcttaca acagcagcca aactaatggt   1680
tgtcatacca gactataaca catataaaaa tacgtgtgat ggtacaacat ttacttatgc   1740
atcagcattg tgggaaatcc aacaggttgt agatgcagat agtaaaattg ttcaacttag   1800
tgaaattagt atggacaatt cacctaattt agcatggcct cttattgtaa cagctttaag   1860
ggccaattct gctgtcaaat tacagaataa tgagcttagt cctgttgcac tacgacagat   1920
gtcttgtgct gccggtacta cacaaactgc ttgcactgat gacaatgcgt tagcttacta   1980
caacacaaca aagggaggta ggtttgtact tgcactgtta tccgatttac aggatttgaa   2040
atgggctaga ttccctaaga gtgatggaac tggtactatc tatacagaac tggaaccacc   2100
ttgtaggttt gttacagaca cacctaaagg tcctaaagtg aagtatttat actttattaa   2160
aggattaaac aacctaaata gaggtatggt acttggtagt ttagctgcca cagtacgtct   2220
acaagctggt aatgcaacag aagtgcctgc caattcaact gtattatctt tctgtgctttt   2280 tgctgtagat gctgctaaag cttacaaaga ttatctagct agtgggggac aaccaatcac   2340
taattgtgtt aagatgttgt gtacacacac tggtactggt caggcaataa cagttacacc   2400
ggaagccaat atggatcaag aatcctttgg tggtgcatcg tgttgtctgt actgccgttg   2460
ccacatagat catccaaatc ctaaaggatt ttgtgactta aaaggtaagt atgtacaaat   2520
acctacaact tgtgctaatg accctgtggg ttttacactt aaaaacacag tctgtaccgt   2580
```

```
ctgcggtatg tggaaaggtt atggctgtag ttgtgatcaa ctccgcgaac ccatgcttca   2640
gtcagctgat gcacaatcgt ttttaaacgg gtttgcggtg taagtgcagc ccgtcttaca   2700
ccgtgcggca caggcactag tactgatgtc gtatacaggg cttttgacat ctacaatgat   2760
aaagtagctg gttttgctaa attcctaaaa actaattgtt gtcgcttcca agaaaaggac   2820
gaagatgaca atttaattga ttcttacttt gtagttaaga gacacacttt ctctaactac   2880
caacatgaag aaacaattta taatttactt aaggattgtc cagctgttgc taaacatgac   2940
ttctttaagt ttagaataga cggtgacatg gtaccacata tatcacgtca acgtcttact   3000
aaatacacaa tggcagacct cgtctatgct ttaaggcatt ttgatgaagg taattgtgac   3060
acattaaaag aaatacttgt cacatacaat tgttgtgatg a                       3101
```

<210> SEQ ID NO 23
<211> LENGTH: 2940
<212> TYPE: DNA
<213> ORGANISM: SARS-CoV-2

<400> SEQUENCE: 23

```
gcgcggatcc ccgtgcggca caggcactag tactgatgtc gtatacaggg cttttgacat     60
ctacaatgat aaagtagctg gttttgctaa attcctaaaa actaattgtt gtcgcttcca    120
agaaaaggac gaagatgaca atttaattga ttcttacttt gtagttaaga gacacacttt    180
ctctaactac caacatgaag aaacaattta taatttactt aaggattgtc cagctgttgc    240
taaacatgac ttctttaagt ttagaataga cggtgacatg gtaccacata tatcacgtca    300
acgtcttact aaatacacaa tggcagacct cgtctatgct ttaaggcatt ttgatgaagg    360
taattgtgac acattaaaag aaatacttgt cacatacaat tgttgtgatg atgattattt    420
caataaaaag gactggtatg attttgtaga aaacccagat atattacgcg tatacgccaa    480
cttaggtgaa cgtgtacgcc aagctttgtt aaaaacagta caattctgtg atgccatgcg    540
aaatgctggt attgttggtg tactgacatt agataatcaa gatctcaatg gtaactggta    600
tgatttcggt gatttcatac aaaccacgcc aggtagtgga gttcctgttg tagattctta    660
ttattcattg ttaatgccta tattaacctt gaccagggct ttaactgcag agtcacatgt    720
tgacactgac ttaacaaagc cttacattaa gtgggatttg ttaaaatatg acttcacgga    780
agagaggtta aaactctttg accgttattt taaatattgg gatcagacat accacccaaa    840
ttgtgttaac tgtttggatg acagatgcat tctgcattgt gcaaacttta atgttttatt    900
ctctacagtg ttcccaccta caagttttgg accactagtg agaaaaatat ttgttgatgg    960
tgttccattt gtagtttcaa ctggatacca cttcagagag ctaggtgttg tacataatca   1020
ggatgtaaac ttacatagct ctagacttag ttttaaggaa ttacttgtgt atgctgctga   1080
ccctgctatg cacgctgctt ctggtaatct attactagat aaacgcacta cgtgcttttc   1140
agtagctgca cttactaaca atgttgcttt tcaaactgtc aaacccggta attttaacaa   1200
agacttctat gactttgctg tgtctaaggg tttctttaag gaaggaagtt ctgttgaatt   1260
aaaacacttc ttctttgctc aggatggtaa tgctgctatc agcgattatg actactatcg   1320
ttataatcta ccaacaatgt gtgatatcag acaactacta tttgtagttg aagttgttga   1380
taagtacttt gattgttacg atggtggctg tattaatgct aaccaagtca tcgtcaacaa   1440
cctagacaaa tcagctggtt ttccatttaa taaatggggt aaggctagac tttattatga   1500
ttcaatgagt tatgaggatc aagatgcact tttcgcatat acaaaacgta atgtcatccc   1560
tactataact caaatgaatc ttaagtatgc cattagtgca aagaatagag ctcgcaccgt   1620
```

| | |
|---|---|
| agctggtgtc tctatctgta gtactatgac caatagacag tttcatcaaa aattattgaa | 1680 |
| atcaatagcc gccactagag gagctactgt agtaattgga acaagcaaat tctatggtgg | 1740 |
| ttggcacaac atgttaaaaa ctgtttatag tgatgtagaa acccctcacc ttatggggttg | 1800 |
| ggattatcct aaatgtgata gagccatgcc taacatgctt agaattatgg cctcacttgt | 1860 |
| tcttgctcgc aaacatacaa cgtgttgtag cttgtcacac cgtttctata gattagctaa | 1920 |
| tgagtgtgct caagtattga gtgaaatggt catgtgtggc ggttcactat atgttaaacc | 1980 |
| aggtggaacc tcatcaggag atgccacaac tgcttatgct aatagtgttt ttaacatttg | 2040 |
| tcaagctgtc acggccaatg ttaatgcact tttatctact gatggtaaca aaattgccga | 2100 |
| taagtatgtc cgcaatttac aacacagact ttatgagtgt ctctatagaa atagagatgt | 2160 |
| tgacacagac tttgtgaatg agttttacgc atatttgcgt aaacatttct caatgatgat | 2220 |
| actctctgac gatgctgttg tgtgtttcaa tagcacttat gcatctcaag gtctagtggc | 2280 |
| tagcataaag aactttaagt cagttctttta ttatcaaaac aatgttttta tgtctgaagc | 2340 |
| aaaatgttgg actgagactg accttactaa aggacctcat gaattttgct ctcaacatac | 2400 |
| aatgctagtt aaacagggtg atgattatgt gtaccttcct tacccagatc catcaagaat | 2460 |
| cctaggggcc ggctgttttg tagatgatat cgtaaaaaca gatggtacac ttatgattga | 2520 |
| acggttcgtg tctttagcta tagatgctta cccacttact aaacatccta atcaggagta | 2580 |
| tgctgatgtc tttcatttgt acttacaata cataagaaag ctacatgatg agttaacagg | 2640 |
| acacatgtta gacatgtatt ctgttatgct tactaatgat aacacttcaa ggtattggga | 2700 |
| acctgagttt tatgaggcta tgtacacacc gcatacagtc ttacaggctg ttggggcttg | 2760 |
| tgttctttgc aattcacaga cttcattaag atgtggtgct tgcatacgta gaccattctt | 2820 |
| atgttgtaaa tgctgttacg accatgtcat atcaacatca cataaattag tcttgtctgt | 2880 |
| taatccgtat gtttgcaatg ctccaggttg tgatgtcaca gatgtgactc tcgcgaggcc | 2940 |

<210> SEQ ID NO 24
<211> LENGTH: 3110
<212> TYPE: DNA
<213> ORGANISM: SARS-CoV-2

<400> SEQUENCE: 24

| | |
|---|---|
| tatgaggcta tgtacacacc gcatacagtc ttacaggctg ttggggcttg tgttctttgc | 60 |
| aattcacaga cttcattaag atgtggtgct tgcatacgta gaccattctt atgttgtaaa | 120 |
| tgctgttacg accatgtcat atcaacatca cataaattag tcttgtctgt taatccgtat | 180 |
| gtttgcaatg ctccaggttg tgatgtcaca gatgtgactc aactttactt aggaggtatg | 240 |
| agctattatt gtaaatcaca taaaccaccc attagttttc cattgtgtgc taatggacaa | 300 |
| gttttttggtt tatataaaaa tacatgtgtt ggtagcgata atgttactga ctttaatgca | 360 |
| attgcaacat gtgactggac aaatgctggt gattacattt tagctaacac ctgtactgaa | 420 |
| agactcaagc ttttttgcagc agaaacgctc aaagctactg aggagacatt taaactgtct | 480 |
| tatggtattg ctactgtacg tgaagtgctg tctgacagag aattacatct ttcatgggaa | 540 |
| gttggtaaac ctagaccacc acttaaccga attatgtct ttactggtta tcgtgtaact | 600 |
| aaaaacagta agtacaaat aggagagtac accttttgaaa aaggtgacta tggtgatgct | 660 |
| gttgtttacc gaggtacaac aacttacaaa ttaaatgttg gtgattattt tgtgctgaca | 720 |
| tcacatacag taatgccatt aagtgcacct acactagtgc cacaagagca ctatgttaga | 780 |

```
attactggct tatacccaac actcaatatc tcagatgagt tttctagcaa tgttgcaaat    840
tatcaaaagg ttggtatgca aaagtattct acactccagg gaccacctgg tactggtaag    900
agtcattttg ctattggcct agctctctac taccttctg ctcgcatagt gtatacagct    960
tgctctcatg ccgctgttga tgcactatgt gagaaggcat taaaatattt gcctatagat   1020
aaatgtagta gaattatacc tgcacgtgct cgtgtagagt gttttgataa attcaaagtg   1080
aattcaacat tagaacagta tgtcttttgt actgtaaatg cattgcctga dacgacagca   1140
gatatagttg tctttgatga aatttcaatg gccacaaatt atgatttgag tgttgtcaat   1200
gccagattac gtgctaagca ctatgtgtac attggcgacc ctgctcaatt acctgcacca   1260
cgcacattgc taactaaggg cacactagaa ccagaatatt tcaattcagt gtgtagactt   1320
atgaaaacta taggtccaga catgttcctc ggaacttgtc ggcgttgtcc tgctgaaatt   1380
gttgacactg tgagtgcttt ggtttatgat aataagctta aagcacataa agacaaatca   1440
gctcaatgct ttaaaatgtt ttataagggt gttatcacgc atgatgtttc atctgcaatt   1500
aacaggccac aaataggcgt ggtaagagaa ttccttacac gtaaccctgc ttggagaaaa   1560 gctgtctta tttcacctta taattcacag aatgctgtag cctcaaagat tttgggacta   1620
ccaactcaaa ctgttgattc atcacagggc tcagaatatg actatgtcat attcactcaa   1680
accactgaaa cagctcactc ttgtaatgta aacagattta atgttgctat taccagagca   1740
aaagtaggca actttgcat aatgtctgat agagaccttt atgacaagtt gcaatttaca   1800
agtcttgaaa ttccacgtag gaatgtggca actttacaag ctgaaaatgt aacaggactc   1860
tttaaagatt gtagtaaggt aatcactggg ttacatccta cacaggcacc tacacacctc   1920
agtgttgaca ctaaattcaa aactgaaggt ttatgtgttg acatacctgg catacctaag   1980
gacatgacct atagaagact catctctatg atgggtttta aaatgaatta tcaagttaat   2040
ggttacccta acatgtttat cacccgcgaa gaagctataa gacatgtacg tgcatggatt   2100
ggcttcgatg tcgagggtg tcatgctact agagaagctg ttggtaccaa tttacctta   2160 cagctaggtt tttctacagg tgttaaccta gttgctgtac ctacaggtta tgttgataca   2220
cctaataata cagatttttc cagagttagt gctaaaccac cgcctggaga tcaatttaaa   2280
cacctcatac cacttatgta caaggactt ccttggaatg tagtgcgtat aaagattgta   2340
caaatgttaa gtgacacact taaaatctc tctgacagag tcgtatttgt cttatgggca   2400
catggctttg agttgacatc tatgaagtat tttgtgaaaa taggacctga gcgcacctgt   2460
tgtctatgtg atagacgtgc cacatgcttt tccactgctt cagacactta tgcctgttgg   2520
catcattcta ttggatttga ttacgtctat aatccgttta tgattgatgt tcaacaatgg   2580
ggttttacag gtaacctaca aagcaaccat gatctgtatt gtcaagtcca tggtaatgca   2640
catgtagcta gttgtgatgc aatcatgact aggtgtctag ctgtccacga gtgctttgtt   2700
aagcgtgttg actggactat tgaatatcct ataattggtg atgaactgaa gattaatgcg   2760
gcttgtagaa aggttcaaca catggttgtt aaagctgcat tattagcaga caaattccca   2820
gttcttcacg acattggtaa ccctaaagct attaagtgtg tacctcaagc tgatgtagaa   2880
tggaagttct atgatgcaca gccttgtagt gacaaagctt ataaaataga agaattattc   2940
tattcttatg ccacacattc tgacaaattc acagatggtg tatgcctatt ttggaattgc   3000
aatgtcgata gatatcctgc taattccatt gtttgtagat ttgacactag agtgctatct   3060
aaccttaact tgcctggttg tgatggtggc agtttgtatg tcgcgaggcc              3110
```

-continued

<210> SEQ ID NO 25
<211> LENGTH: 3167
<212> TYPE: DNA
<213> ORGANISM: SARS-CoV-2

<400> SEQUENCE: 25
gcgcggatcc aagcgtgttg actggactat tgaatatcct ataattggtg atgaactgaa 60
gattaatgcg gcttgtagaa aggttcaaca catggttgtt aaagctgcat tattagcaga 120
caaattccca gttcttcacg acattggtaa ccctaaagct attaagtgtg tacctcaagc 180
tgatgtagaa tggaagttct atgatgcaca gccttgtagt gacaaagctt ataaaataga 240
agaattattc tattcttatg ccacacattc tgacaaattc acagatggtg tatgcctatt 300
ttggaattgc aatgtcgata gatatcctgc taattccatt gtttgtagat ttgacactag 360
agtgctatct aaccttaact tgcctggttg tgatggtggc agtttgtatg taaataaaca 420
tgcattccac acaccagctt ttgataaaag tgcttttgtt aatttaaaac aattaccatt 480
tttctattac tctgacagtc catgtgagtc tcatggaaaa caagtagtgt cagatataga 540
ttatgtacca ctaaagtctg ctacgtgtat aacacgttgc aatttaggtg gtgctgtctg 600
tagacatcat gctaatgagt acagattgta tctcgatgct tataacatga tgatctcagc 660
tggctttagc ttgtgggttt acaaacaatt tgatacttat aacctctgga acacttttac 720
aagacttcag agtttagaaa atgtggcttt taatgttgta aataagggac actttgatgg 780
acaacagggt gaagtaccag tttctatcat taataacact gtttacacaa aagttgatgg 840
tgttgatgta gaattgtttg aaaataaaac aacattacct gttaatgtag catttgagct 900
ttgggctaag cgcaacatta aaccagtacc agaggtgaaa atactcaata atttgggtgt 960
ggacattgct gctaatactg tgatctggga ctacaaaaga gatgctccag cacatatatc 1020
tactattggt gtttgttcta tgactgacat agccaagaaa ccaactgaaa cgatttgtgc 1080
accactcact gtcttttttg atggtagagt tgatggtcaa gtagacttat ttagaaatgc 1140
ccgtaatggt gttcttatta cagaaggtag tgttaaaggt ttacaaccat ctgtaggtcc 1200
caaacaagct agtcttaatg gagtcacatt aattggagaa gccgtaaaaa cacagttcaa 1260
ttattataag aaagttgatg gtgttgtcca acaattacct gaaacttact ttactcagag 1320
tagaaattta caagaattta aacccaggag tcaaatggaa attgatttct tagaattagc 1380
tatggatgaa ttcattgaac ggtataaatt agaaggctat gccttcgaac atatcgttta 1440
tggagatttt agtcatagtc agttaggtgg tttacatcta ctgattggac tagctaaacg 1500
ttttaaggaa tcaccttttg aattagaaga ttttattcct atggacagta cagttaaaaa 1560
ctatttcata acagatgcgc aaacaggttc atctaagtgt gtgtgttctg ttattgattt 1620
attacttgat gattttgttg aaataataaa atcccaagat ttatctgtag tttctaaggt 1680
tgtcaaagtg actattgact atacagaaat ttcatttatg ctttggtgta aagatggcca 1740
tgtagaaaca ttttacccaa aattacaatc tagtcaagcg tggcaaccgg gtgttgctat 1800
gcctaatctt tacaaaatgc aaagaatgct attagaaaag tgtgaccttc aaaattatgg 1860
tgatagtgca acattaccta aaggcataat gatgaatgtc gcaaaatata ctcaactgtg 1920
tcaatattta aacacattaa cattagctgt accctataat atgagagtta tacattttgg 1980
tgctggttct gataaaggag ttgcaccagg tacagctgtt ttaagacagt ggttgcctac 2040
gggtacgctg cttgtcgatt cagatcttaa tgactttgtc tctgatgcag attcaacttt 2100
gattggtgat tgtgcaactg tacatacagc taataaatgg gatctcatta ttagtgatat 2160

```
gtacgaccct aagactaaaa atgttacaaa agaaaatgac tctaaagagg gttttttcac    2220
ttacatttgt gggtttatac aacaaaagct agctcttgga ggttccgtgg ctataaagat    2280
aacagaacat tcttggaatg ctgatcttta aagctcatg  ggacacttcg catggtggac    2340
agcctttgtt actaatgtga atgcgtcatc atctgaagca ttttaattg  gatgtaatta    2400 tcttggcaaa ccacgcgaac aaatagatgg ttatgtcatg catgcaaatt acatattttg    2460
gaggaataca aatccaattc agttgtcttc ctattcttta tttgacatga gtaaatttcc    2520
ccttaaatta aggggtactg ctgttatgtc tttaaaagaa ggtcaaatca atgatatgat    2580
tttatctctt cttagtaaag gtagacttat aattagagaa acaacagag  ttgttatttc    2640 tagtgatgtt cttgttaaca actaaacgaa caatgtttgt ttttcttgtt ttattgccac    2700
tagtctctag tcagtgtgtt aatcttacaa ccagaactca attacccct  gcatacacta    2760 attctttcac acgtggtgtt tattaccctg acaaagtttt cagatcctca gttttacatt    2820
caactcagga cttgttctta cctttctttt ccaatgttac ttggttccat gctatacatg    2880
tctctgggac caatggtact aagaggtttg ataaccctgt cctaccattt aatgatggtg    2940
tttattttgc ttccactgag aagtctaaca ataagagg  ctggattttt ggtactactt    3000
tagattcgaa gacccagtcc ctacttattg ttaataacgc tactaatgtt gttattaaag    3060
tctgtgaatt tcaattttgt aatgatccat ttttgggtgt ttattaccac aaaaacaaca    3120
aaagttggat ggaaagtgag ttcagagttt attctagtac gtaggcc                  3167

<210> SEQ ID NO 26
<211> LENGTH: 3117
<212> TYPE: DNA
<213> ORGANISM: SARS-CoV-2

<400> SEQUENCE: 26
tcagtgtgtt aatcttacaa ccagaactca attacccct  gcatacacta attctttcac      60
acgtggtgtt tattaccctg acaaagtttt cagatcctca gttttacatt caactcagga     120
cttgttctta cctttctttt ccaatgttac ttggttccat gctatacatg tctctgggac     180
caatggtact aagaggtttg ataaccctgt cctaccattt aatgatgtg tttattttgc     240 ttccactgag aagtctaaca ataagagg  ctggattttt ggtactactt tagattcgaa     300
gacccagtcc ctacttattg ttaataacgc tactaatgtt gttattaaag tctgtgaatt     360
tcaattttgt aatgatccat ttttgggtgt ttattaccac aaaaacaaca aaagttggat     420
ggaaagtgag ttcagagttt attctagtgc gaataattgc acttttgaat atgtctctca     480
gccttttctt atggaccttg aaggaaaaca gggtaatttc aaaaatctta gggaatttgt     540
gtttaagaat attgatggtt attttaaaat atattctaag cacacgccta ttaattagt     600 gcgtgatctc cctcagggtt tttcggcttt agaaccattg gtagatttgc caataggtat     660
taacatcact aggttcaaa  cttacttgc  tttacataga agttatttga ctcctggtga     720
ttcttcttca ggttggacag ctggtgctgc agcttattat gtgggttatc ttcaacctag     780
gactttccta ttaaaatata tgaaaatgg  aaccattaca gatgctgtag actgtgcact     840 tgacccctc  tcagaaacaa agtgtacgtt gaaatcctc  actgtagaaa aggaatcta     900 tcaaacttct aactttagag tccaaccaac agaatctatt gttagatttc ctaatattac     960
aaacttgtgc ccttttggtg aagtttttaa cgccaccaga tttgcatctg tttatgcttg    1020
gaacaggaag agaatcagca actgtgttgc tgattattct gtcctatata attccgcatc    1080
attttccact tttaagtgtt atggagtgtc tcctactaaa ttaaatgatc tctgctttac    1140
```

```
taatgtctat gcagattcat ttgtaattag aggtgatgaa gtcagacaaa tcgctccagg    1200
gcaaactgga agattgctg attataatta taaattacca gatgatttta caggctgcgt    1260
tatagcttgg aattctaaca atcttgattc taaggttggt ggtaattata attacctgta    1320
tagattgttt aggaagtcta atctcaaacc ttttgagaga gatatttcaa ctgaaatcta    1380
tcaggccggt agcacacctt gtaatggtgt tgaaggtttt aattgttact tcctttaca    1440 atcatatggt ttccaaccca ctaatggtgt tggttaccaa ccatacagag tagtagtact    1500
ttcttttgaa cttctacatg caccagcaac tgtttgtgga cctaaaaagt ctactaattt    1560
ggttaaaaac aaatgtgtca atttcaactt caatggttta acaggcacag gtgttcttac    1620
tgagtctaac aaaaagtttc tgcctttcca acaatttggc agagacattg ctgacactac    1680
tgatgctgtc cgtgatccac agacacttga gattcttgac attacaccat gttcttttgg    1740
tggtgtcagt gttataacac aggaacaaa tacttctaac caggttgctg ttctttatca    1800
ggatgttaac tgcacagaag tccctgttgc tattcatgca gatcaactta ctcctacttg    1860
gcgtgtttat tctacaggtt ctaatgtttt tcaaacacgt gcaggctgtt aatagggc    1920 tgaacatgtc aacaactcat atgagtgtga catacccatt ggtgcaggta tatgcgctag    1980
ttatcagact cagactaatt ctcctcggcg ggcacgtagt gtagctagtc aatccatcat    2040
tgcctacact atgtcacttg gtgcagaaaa ttcagttgct tactctaata actctattgc    2100
catacccaca aattttacta ttagtgttac cacagaaatt ctaccagtgt ctatgaccaa    2160
gacatcagta gattgtacaa tgtacatttg tggtgattca actgaatgca gcaatctttt    2220
gttgcaatat ggcagttttt gtacacaatt aaaccgtgct taactggaa tagctgttga    2280 acaagacaaa aacacccaag aagtttttgc acaagtcaaa caaatttaca aaacaccacc    2340
aattaaagat tttggtggtt ttaatttttc acaaatatta ccagatccat caaaaccaag    2400
caagaggtca tttattgaag atctactttt caacaaagtg acacttgcag atgctggctt    2460
catcaaacaa tatggtgatt gccttggtga tattgctgct agagacctca tttgtgcaca    2520
aaagtttaac ggccttactg ttttgccacc tttgctcaca gatgaaatga ttgctcaata    2580
cacttctgca ctgttagcgg gtacaatcac ttctggttgg accttggtg caggtgctgc    2640 attacaaata ccatttgcta tgcaaatggc ttataggttt aatggtattg gagttacaca    2700
gaatgttctc tatgagaacc aaaaaattgat tgccaaccaa tttaatagtg ctattggcaa    2760
aattcaagac tcactttctt ccacagcaag tgcacttgga aaacttcaag atgtggtcaa    2820
ccaaaatgca caagctttaa acacgcttgt taaacaactt agctccaatt ttggtgcaat    2880
ttcaagtgtt ttaaatgata tcctttcacg tcttgacaaa gttgaggctg aagtgcaaat    2940
tgataggttg atcacaggca gacttcaaag tttgcagaca tatgtgactc aacaattaat    3000
tagagctgca gaaatcagag cttctgctaa tcttgctgct actaaaatgt cagagtgtgt    3060
acttggacaa tcaaaaagag ttgatttttg tggaaagggc tatcatctta tgtcctt      3117
```

<210> SEQ ID NO 27
<211> LENGTH: 2863
<212> TYPE: DNA
<213> ORGANISM: SARS-CoV-2

<400> SEQUENCE: 27

```
gaatgttctc tatgagaacc aaaaaattgat tgccaaccaa tttaatagtg ctattggcaa      60
aattcaagac tcactttctt ccacagcaag tgcacttgga aaacttcaag atgtggtcaa     120
```

```
ccaaaatgca caagctttaa acacgcttgt taaacaactt agctccaatt ttggtgcaat      180
ttcaagtgtt ttaaatgata tcctttcacg tcttgacaaa gttgaggctg aagtgcaaat      240
tgataggttg atcacaggca gacttcaaag tttgcagaca tatgtgactc aacaattaat      300
tagagctgca gaaatcagag cttctgctaa tcttgctgct actaaaatgt cagagtgtgt      360
acttggacaa tcaaaaagag ttgattttg tggaaagggc tatcatctta tgtccttccc       420
tcagtcagca cctcatggtg tagtcttctt gcatgtgact tatgtccctg cacaagaaaa      480
gaacttcaca actgctcctg ccatttgtca tgatggaaaa gcacactttc ctcgtgaagg      540
tgtctttgtt tcaaatggca cacactggtt tgtaacacaa aggaattttt atgaaccaca      600
aatcattact acagacaaca catttgtgtc tggtaactgt gatgttgtaa taggaattgt      660
caacaacaca gtttatgatc ctttgcaacc tgaattagac tcattcaagg aggagttaga      720
taaatatttt aagaatcata catcaccaga tgttgattta ggtgacatct ctggcattaa      780
tgcttcagtt gtaaacattc aaaaagaaat tgaccgcctc aatgaggttg ccaagaattt      840
aaatgaatct ctcatcgatc tccaagaact tggaaagtat gagcagtata taaaatggcc      900
atggtacatt tggctaggtt ttatagctgg cttgattgcc atagtaatgg tgacaattat      960
gctttgctgt atgaccagtt gctgtagttg tctcaagggc tgttgttctt gtggatcctg     1020
ctgcaaattt gatgaagacg actctgagcc agtgctcaaa ggagtcaaat tacattacac     1080
ataaacgaac ttatgatttt gtttatgaga atcttcacaa ttggaactgt aactttgaag     1140
caaggtgaaa tcaaggatgc tactccttca gattttgttc gcgctactgc aacgataccg     1200
atacaagcct cactcccttt cggatggctt attgttggcg ttgcacttct tgctgttttt     1260
cagagcgctt ccaaaatcat aaccctcaaa agagatggc aactagcact ctccaagggt      1320
gttcactttg tttgcaactt gctgttgttg tttgtaacag tttactcaca ccttttgctc     1380
gttgctgctg gccttgaagc cccttttctc tatctttatg ctttagtcta cttcttgcag     1440
agtataaact ttgtaagaat aataatgagg ctttggcttt gctggaaatg ccgttccaaa     1500
aacccattac tttatgatgc caactatttt ctttgctggc atactaattg ttacgactat     1560
tgtataccct acaatagtgt aacttcttca attgtcatta cttcaggtga tgcacacaaca    1620 agtcctattt ctgaacatga ctaccagatt ggtggttata ctgaaaaatg ggaatctgga     1680
gtaaaagact gtgttgtatt acacagttac ttcacttcag actattacca gctgtactca     1740
actcaattga gtacagacac tggtgttgaa catgttacct tcttcatcta caataaaatt     1800
gttgatgagc tgaagaaca tgtccaaatt cacacaatcg acggttcatc cggagttgtt     1860
aatccagtaa tggaaccaat ttatgatgaa ccgacgacga ctactagcgt gcctttgtaa     1920
gcacaagctg atgagtacga acttatgtac tcattcgttt cggaagagac aggtacgtta     1980
atagttaata gcgtacttct ttttcttgct ttcgtggtat tcttgctagt tacactagcc     2040
atccttactg cgcttcgatt gtgtgcgtac tgctgcaata ttgttaacgt gagtcttgta     2100
aaaccttctt tttacgttta ctctcgtgtt aaaaatctga attcttctag agttcctgat     2160
cttctggtct aaacgaacta atattatat tagttttct gtttggaact ttaattttag       2220
ccatggcaga ttccaacggt actattaccg ttgaagagct taaaaagctc cttgaacaat     2280
ggaacctagt aataggtttc ctattcctta catggatttg tcttctacaa tttgcctatg     2340
ccaacaggaa taggttttg tatataatta agttaatttt cctctggctg ttatggccag      2400
taactttagc ttgttttgtg cttgctgctg tttacagaat aaattggatc accggtggaa     2460
ttgctatcgc aatggcttgt cttgtaggct tgatgtggct cagctacttc attgcttctt     2520
```

| | | | | |
|---|---|---|---|---|
| tcagactgtt | tgcgcgtacg | cgttccatgt | ggtcattcaa | tccagaaact aacattcttc | 2580 |
| tcaacgtgcc | actccatggc | actattctga | ccagaccgct | tctagaaagt gaactcgtaa | 2640 |
| tcggagctgt | gatccttcgt | ggacatcttc | gtattgctgg | acaccatcta ggacgctgtg | 2700 |
| acatcaagga | cctgcctaaa | gaaatcactg | ttgctacatc | acgaacgctt tcttattaca | 2760 |
| aattgggagc | ttcgcagcgt | gtagcaggtg | actcaggttt | tgctgcatac agtcgctaca | 2820 |
| ggattggcaa | ctataaatta | aacacagacc | attccagtag cag | | 2863 |

<210> SEQ ID NO 28
<211> LENGTH: 3172
<212> TYPE: DNA
<213> ORGANISM: SARS-CoV-2

<400> SEQUENCE: 28

| | | | | | |
|---|---|---|---|---|---|
| tcctctggct | gttatggcca | gtaactttag | cttgttttgt | gcttgctgct gtttacagaa | 60 |
| taaattggat | caccggtgga | attgctatcg | caatggcttg | tcttgtaggc ttgatgtggc | 120 |
| tcagctactt | cattgcttct | ttcagactgt | tgcgcgtac | gcgttccatg tggtcattca | 180 |
| atccagaaac | taacattctt | ctcaacgtgc | cactccatgg | cactattctg accagaccgc | 240 |
| ttctagaaag | tgaactcgta | atcggagctg | tgatccttcg | tggacatctt cgtattgctg | 300 |
| gacaccatct | aggacgctgt | gacatcaagg | acctgcctaa | agaaatcact gttgctacat | 360 |
| cacgaacgct | ttcttattac | aaattgggag | cttcgcagcg | tgtagcaggt gactcaggtt | 420 |
| ttgctgcata | cagtcgctac | aggattggca | actataaatt | aaacacagac cattccagta | 480 |
| gcagtgacaa | tattgctttg | cttgtacagt | aagtgacaac | agatgtttca tctcgttgac | 540 |
| tttcaggtta | ctatagcaga | gatattacta | attattatga | ggacttttaa agttccatt | 600 |
| tggaatcttg | attacatcat | aaacctcata | attaaaaatt | tatctaagtc actaactgag | 660 |
| aataaatatt | ctcaattaga | tgaagagcaa | ccaatggaga | ttgattaaac gaacatgaaa | 720 |
| attattcttt | tcttggcact | gataacactc | gctacttgtg | agctttatca ctaccaagag | 780 |
| tgtgttagag | gtacaacagt | acttttaaaa | gaaccttgct | cttctggaac atacgagggc | 840 |
| aattcaccat | ttcatcctct | agctgataac | aaatttgcac | tgacttgctt tagcactcaa | 900 |
| tttgcttttg | cttgtcctga | cggcgtaaaa | cacgtctatc | agttacgtgc cagatcagtt | 960 |
| tcacctaaac | tgttcatcag | acaagaggaa | gttcaagaac | tttactctcc aattttttctt | 1020 |
| attgttgcgg | caatagtgtt | tataacactt | gcttcacac | tcaaaagaaa gacagaatga | 1080 |
| ttgaactttc | attaattgac | ttctatttgt | gcttttagc | ctttctgcta ttccttgttt | 1140 |
| taattatgct | tattatcttt | tggttctcac | ttgaactgca | agatcataat gaaacttgtc | 1200 |
| acgcctaaac | gaacatgaaa | tttccttgttt | tcttaggaat | catcacaact gtagctgcat | 1260 |
| ttcaccaaga | atgtagttta | cagtcatgta | ctcaacatca | accatatgta gttgatgacc | 1320 |
| cgtgtcctat | tcacttctat | tctaaatggt | atattagagt | aggagctaga aaatcagcac | 1380 |
| ctttaattga | attgtgcgtg | gatgaggctg | gttctaaatc | acccattcag tacatcgata | 1440 |
| tcggtaatta | tacagtttcc | tgtttaccctt | ttacaattaa | ttgccaggaa cctaaattgg | 1500 |
| gtagtcttgt | agtgcgttgt | tcgttctatg | aagactttt | agagtatcat gacgttcgtg | 1560 |
| ttgttttaga | tttcatctaa | acgaacaaac | taaaatgtct | gataatggac cccaaaatca | 1620 |
| gcgaaatgca | ccccgcatta | cgtttggtgg | accctcagat | tcaactggca gtaaccagaa | 1680 |
| tggagaacgc | agtggggcgc | gatcaaaaca | acgtcggccc | caaggtttac ccaataatac | 1740 |

-continued

```
tgcgtcttgg ttcaccgctc tcactcaaca tggcaaggaa gaccttaaat tccctcgagg   1800
acaaggcgtt ccaattaaca ccaatagcag tccagatgac caaattggct actaccgaag   1860
agctaccaga cgaattcgtg gtggtgacgg taaaatgaaa gatctcagtc caagatggta   1920
tttctactac ctaggaactg ggccagaagc tggacttccc tatggtgcta acaaagacgg   1980
catcatatgg gttgcaactg agggagcctt gaatacacca aaagatcaca ttggcacccg   2040
caatcctgct aacaatgctg caatcgtgct acaacttcct caaggaacaa cattgccaaa   2100
aggcttctac gcagaaggga gcagaggcgg cagtcaagcc tcttctcgtt cctcatcacg   2160
tagtcgcaac agttcaagaa attcaactcc aggcagcagt aggggaactt ctcctgctag   2220
aatggctggc aatggcggtg atgctgctct tgctttgctg ctgcttgaca gattgaacca   2280
gcttgagagc aaaatgtctg gtaaaggcca acaacaacaa ggccaaactg tcactaagaa   2340
atctgctgct gaggcttcta agaagcctcg gcaaaaacgt actgccacta aagcatacaa   2400
tgtaacacaa gctttcggca gacgtggtcc agaacaaacc caaggaaatt ttggggacca   2460
ggaactaatc agacaaggaa ctgattacaa acattggccg caaattgcac aatttgcccc   2520
cagcgcttca gcgttcttcg gaatgtcgcg cattggcatg gaagtcacac cttcgggaac   2580
gtggttgacc tacacaggtg ccatcaaatt ggatgacaaa gatccaaatt tcaaagatca   2640
agtcattttg ctgaataagc atattgacgc atacaaaaca ttcccaccaa cagagcctaa   2700
aaaggacaaa aagaagaagg ctgatgaaac tcaagcctta ccgcagagac agaagaaaca   2760
gcaaactgtg actcttcttc ctgctgcaga tttggatgat ttctccaaac aattgcaaca   2820
atccatgagc agtgctgact caactcaggc ctaaactcat gcagaccaca caaggcagat   2880
gggctatata aacgttttcg cttttccgtt tacgatatat agtctactct tgtgcagaat   2940
gaattctcgt aactacatag cacaagtaga tgtagttaac tttaatctca catagcaatc   3000
tttaatcagt gtgtaacatt agggaggact tgaaagagcc accacatttt caccgaggcc   3060
acgcggagta cgatcgagtg tacagtgaac aatgctaggg agagctgcct atatggaaga   3120
gccctaatgt gtaaaattaa ttttagtagt gctatcccca tgtgatttta at           3172
```

DIAGNOSTIC CONTROL COMPOSITIONS

CROSS REFERENCE TO RELATED APPLICATIONS

The present application is a U.S. National Phase Application of PCT International Application No. PCT/M2021/053369, filed on Apr. 23, 2021 with the International Bureau, which is an International Application of and claims priority to GB Patent Application Serial No. 2005985.3, filed on Apr. 23, 2020. The contents of the above-referenced applications are herein expressly incorporated by reference in their entireties, including any drawings.

REFERENCE TO A SEQUENCE LISTING

The material in the accompanying Sequence Listing is hereby incorporated by reference into this application. The accompanying Sequence Listing text file, named "Sequence_ Listing_057095-502N01US_ST25.TXT" was created on Oct. 21, 2022 and is 80,838 bytes.

BACKGROUND OF THE INVENTION

Testing for viral infections in many cases requires RNA-based positive controls for testing of instrument suitability, proficiency testing and external quality assurance systems. In a number of cases, the actual virus is used a control which creates numerous occupational health and safety issues and unnecessary exposure of laboratory staff to dangerous human pathogens. Most of these viral controls require specialist shipping and handling procedures and need highly skilled staff and infrastructure, which limits their use. Proficiency testing controls are central to the deployment of any successful diagnostic test and indeed the lack of these remains a significant hurdle to the use of new testing kits as they become available.

The newly emergent severe acute respiratory syndrome coronavirus 2 (SARS-CoV-2) has resulted in a global pandemic prompting radical measures to contain the spread of the virus. Coronavirus disease 2019 (COVID-19) is the infectious disease caused by SARS-CoV-2. The disease was first identified in December 2019 in Wuhan, China, and has since spread globally, resulting in a global pandemic. Common symptoms of COVID-19 include fever, cough and shortness of breath. Other symptoms may include fatigue, muscle pain, diarrhea, sore throat, loss of smell and abdominal pain. The time from exposure to the onset of symptoms is typically five days but may range from two to fourteen days. The majority of cases result in relatively mild symptoms, however some patients progress to viral pneumonia and multi-organ failure.

The rapid spread of SARS-CoV-2 has created a global pandemic, resulting in a grim forecast for the global economy and public health programs of even the most well-resourced nations. Whilst most countries continue to battle against raging local epidemics, with the precise formula for rapidly achieving control remaining elusive, it has been demonstrated that smart, aggressive public health interventions can reduce the rate of new infections. Countries such as China and South Korea have been able to contain the spread of new infections through rapidly deploying testing for Covid-19 infection and disease. When these diagnostics were coupled with effective public health interventions such as isolation and quarantine, a significant flattening of the curve was achieved. Diagnostic testing can adopt one of two modalities, either directed at detecting the nucleic acid (or genetic content) of the virus, a method commonly referred to as RT-PCR, or through serological testing aimed at detecting antibodies against certain viral proteins. RT-PCR tests have the capacity for detecting the virus early in the infection, in individuals who are asymptomatic, and allows for reduction in spread of new infections. A major challenge in containing the spread of the virus has been identifying asymptomatic infections which are reported to be major drivers of the pandemic. As such the demand for RT-PCR tests has increased exponentially all over the world. However, as these become available the need for proficiency testing tools also becomes an urgent priority. Proficiency testing controls allow for an assessment of whether a test is fit for purpose and provides valuable information on the ability of laboratories to carry out testing in a quality assured manner. These controls usually encompass both positive and negative controls. In many cases the disease-causing agent is used as the positive control, for example the single stranded RNA virus. Using the live virus as a positive control for evaluating test performance in this case is not desirable as the corona virus has a rapid, explosive infection force and it's use in this case creates notable public health concerns.

The inventors have thus employed a biomimicry approach to engineer a positive control organism that mimics the genetic material of the SARS-CoV-2 virus and other single stranded RNA viruses, including human immunodeficiency virus (HIV) and hepatitis C virus (HCV), that is targeted by several RT-PCR based diagnostic kits to create a safe, non-infectious and stable positive control that can be rapidly deployed in any setting. The approach uses a *Mycobacterium smegmatis* cell, as an encapsulating casing, which contains a plasmid DNA molecule that has the viral diagnostic targets that mimic the diagnostic profile of the clinical pathogen. Because the genetic material that forms the basis of the molecular assay is RNA, the plasmid DNA further includes elements which allow for RNA expression, stabilisation of the RNA and degradation of the remaining DNA, thereby ensuring that the positive control is an effective control that mimics the diagnostic profile of the virus.

SUMMARY OF THE INVENTION

The present invention relates to a nucleotide cassette comprising a nucleotide sequence corresponding to at least one target nucleic acid from a single stranded RNA diagnostic target. This nucleotide sequence contains an inducible promoter, a nucleotide sequence that encodes artemin, a molecular switch and a nucleotide sequence that encodes a DNAse enzyme and is under control of the molecular switch, wherein the single stranded RNA diagnostic target is converted to an RNA sequence target that is detected by a molecular diagnostic assay. The invention also relates to an RNA expression product of the nucleotide cassette, a vector comprising the nucleotide cassette, and to a cell carrying the nucleotide cassette, the RNA expression product or the vector. In addition, this invention relates to a diagnostic control composition comprising a non-pathogenic recombinant bacterium having a modified genetic content comprising the nucleotide cassette, as well as to methods of producing these recombinant bacteria. The invention also relates to a kit comprising the cell, diagnostic control composition or recombinant bacterium produced according to the method.

According to a first aspect of the present invention there is provided for a nucleotide cassette having the formula:

$$X_1\text{-}X_2\text{-}X_3\text{-}X_4\text{-}X_5$$

wherein, $X_1$ is an inducible promoter; $X_2$ is a nucleotide sequence corresponding to at least one single stranded RNA diagnostic target; $X_3$ is a nucleotide sequence that encodes artemin; $X_4$ is a molecular switch; and $X_5$ is a nucleotide sequence that encodes a DNAse enzyme and is under control of the molecular switch, wherein the single stranded RNA diagnostic target is a sequence detected by a molecular diagnostic assay. In one embodiment, the single stranded RNA diagnostic target is a single stranded RNA virus target, such as a SARS-CoV-2 diagnostic target detected by a molecular diagnostic assay that detects SARS-CoV-2.

In a first embodiment of the nucleotide cassette of the invention, the SARS-CoV-2 target may be selected from the group consisting of genes encoding RdRP1, RdRP2, N protein, E protein, Spike protein, ORF1ab, and combinations thereof. It will be appreciated by those of skill in the art that other regions of the SARS-CoV-2 virus may be contemplated if these are detected in molecular diagnostic tests. For example, the SARS-CoV-2 target may be any sequence in the SARS-CoV-2 genome, which is represented by SEQ ID NOs:18-28. In an alternative embodiment, the target may be one or more other single stranded RNA diagnostic targets that are detected by a molecular diagnostic assay. Non-limiting examples of such targets include single stranded virus targets detected by a diagnostic assay for HCV, HIV, respiratory syncytial virus, influenza virus and Ebola virus. It will be appreciated by those of skill in the art that any single stranded RNA diagnostic target of a molecular diagnostic assay could be used, including the BRCA-ABL human ss-mRNA.

In a second embodiment of the nucleotide cassette of the invention, $X_2$ is selected from the group consisting of SEQ ID NO:2, SEQ ID NO:3, SEQ ID NO:4, SEQ ID NO:5, SEQ ID NO:6, SEQ ID NO:7, or a sequence substantially identical or complementary to any of SEQ ID NOs:2-7, and combinations thereof.

According to a third embodiment of the nucleotide cassette of the invention the inducible promoter is a heat inducible promoter, preferably Hsp60.

In a third embodiment of the nucleotide cassette of the invention the molecular switch may be a theophylline riboswitch that is activated via introduction and binding of theophylline, and which induces the production of DNAse enzyme.

In a further embodiment of the invention the nucleotide cassette comprises the sequence of SEQ ID NO:14 or SEQ ID NO:15, or a sequence substantially identical or complementary thereto.

According to a second aspect of the invention there is provided for an RNA expression product produced by the nucleotide cassette of the first aspect.

According to a third aspect of the present invention there is provided for a vector comprising the nucleotide cassette of the first aspect.

According to a fourth aspect of the present invention there is provided for a cell comprising the nucleotide cassette of the first aspect, the RNA expression product of the second aspect, or the vector of the third aspect.

In a second embodiment of the cell of the invention, the cell is a recombinant *Mycobacterium smegmatis* cell.

According to a fifth aspect of the present invention there is provided for a diagnostic control composition comprising a non-pathogenic recombinant bacterium having a modified genetic content comprising a nucleotide cassette having the formula:

$X_1$-$X_2$-$X_3$-$X_4$-$X_5$ wherein, $X_1$ is an inducible promoter; $X_2$ is a nucleotide sequence corresponding to at least one single stranded RNA diagnostic target; $X_3$ is a nucleotide sequence that encodes artemin; $X_4$ is a molecular switch; and $X_5$ is a nucleotide sequence that encodes a DNAse enzyme and is under control of the molecular switch, wherein the single stranded RNA diagnostic target is a sequence detected by a molecular diagnostic assay and wherein the diagnostic control composition mimics the diagnostic profile of the single stranded RNA diagnostic target. In one embodiment, the single stranded RNA diagnostic target is a single stranded RNA virus target, such as a SARS-CoV-2 diagnostic target detected by a molecular diagnostic assay that detects SARS-CoV-2.

According to a first embodiment of the diagnostic control composition of the present invention the SARS-CoV-2 target may be selected from the group consisting of genes encoding RdRP1, RdRP2, N protein, E protein, Spike protein, ORF1ab, and combinations thereof. It will be appreciated by those of skill in the art that other regions of the SARS-CoV-2 virus may be contemplated by the present invention if these are to be detected in molecular diagnostic tests. For example, the SARS-CoV-2 target may be any sequence in the SARS-CoV-2 genome, which is represented by SEQ ID NOs:18-28. In an alternative embodiment, the target may be one or more other single stranded RNA diagnostic targets that are detected by a molecular diagnostic assay. Non-limiting examples of such targets include single stranded virus targets detected by a diagnostic assay for HCV, HIV, respiratory syncytial virus, influenza virus and Ebola virus. It will be appreciated by those of skill in the art that any single stranded RNA diagnostic target of a molecular diagnostic assay could be used, including the BRCA-ABL human ss-mRNA.

In a second embodiment of the diagnostic control composition, $X_2$ is selected from the group consisting of SEQ ID NO:2, SEQ ID NO:3, SEQ ID NO:4, SEQ ID NO:5, SEQ ID NO:6, SEQ ID NO:7, or a sequence substantially identical or complementary to any of SEQ ID NOs:2-7, and combinations thereof.

According to a third embodiment of the diagnostic control composition of the invention the inducible promoter is a heat inducible promoter, preferably Hsp60.

In another embodiment of the diagnostic control composition, the molecular switch may be a theophylline riboswitch that is activated via introduction and binding of theophylline, and which induces the production of DNAse enzyme.

In a further embodiment of the diagnostic control composition of the invention the nucleotide cassette may comprise the sequence of SEQ ID NO:14 or SEQ ID NO:15, or a sequence substantially identical or complementary thereto.

In yet another embodiment of the diagnostic control composition of the present invention the non-pathogenic recombinant bacterium may be *Mycobacterium smegmatis*.

According to a further aspect of the present invention there is provided for a method of producing a recombinant bacterium that mimics the diagnostic profile of a single stranded RNA of interest in a molecular diagnostic assay, the method comprising:

(i) transforming a non-pathogenic bacterium with a vector comprising the nucleotide cassette described herein and a selection marker to obtain a recombinant bacterium; and (ii) culturing the recombinant bacterium obtained in step (i) under selective conditions in order to select the recombinant bacterium.

In one embodiment of the method of the invention the non-pathogenic bacterium is *Mycobacterium smegmatis*.

In a further embodiment of the method of the invention the recombinant bacterium mimics the diagnostic profile of SARS-CoV-2. In an alternative embodiment, the recombinant bacterium mimics one or more other single stranded RNA viruses that are detected by a molecular diagnostic assay. IN yet a further, embodiment, the single stranded RNA of interest may be BRCA-ABL human ss-mRNA.

In another embodiment of the method of the present invention the selection marker may be an antibiotic selection marker.

In yet a further embodiment of the method of the invention the recombinant bacterium may be either stably or transiently transformed with the vector.

According to yet another aspect of the present invention there is provided for a kit comprising a cell of the invention, a diagnostic control composition of the invention, or the recombinant bacterium produced according to the method of the invention, and instructions for use.

BRIEF DESCRIPTION OF THE FIGURES

Non-limiting embodiments of the invention will now be described by way of example only and with reference to the following figures:

Figures 1, 2:
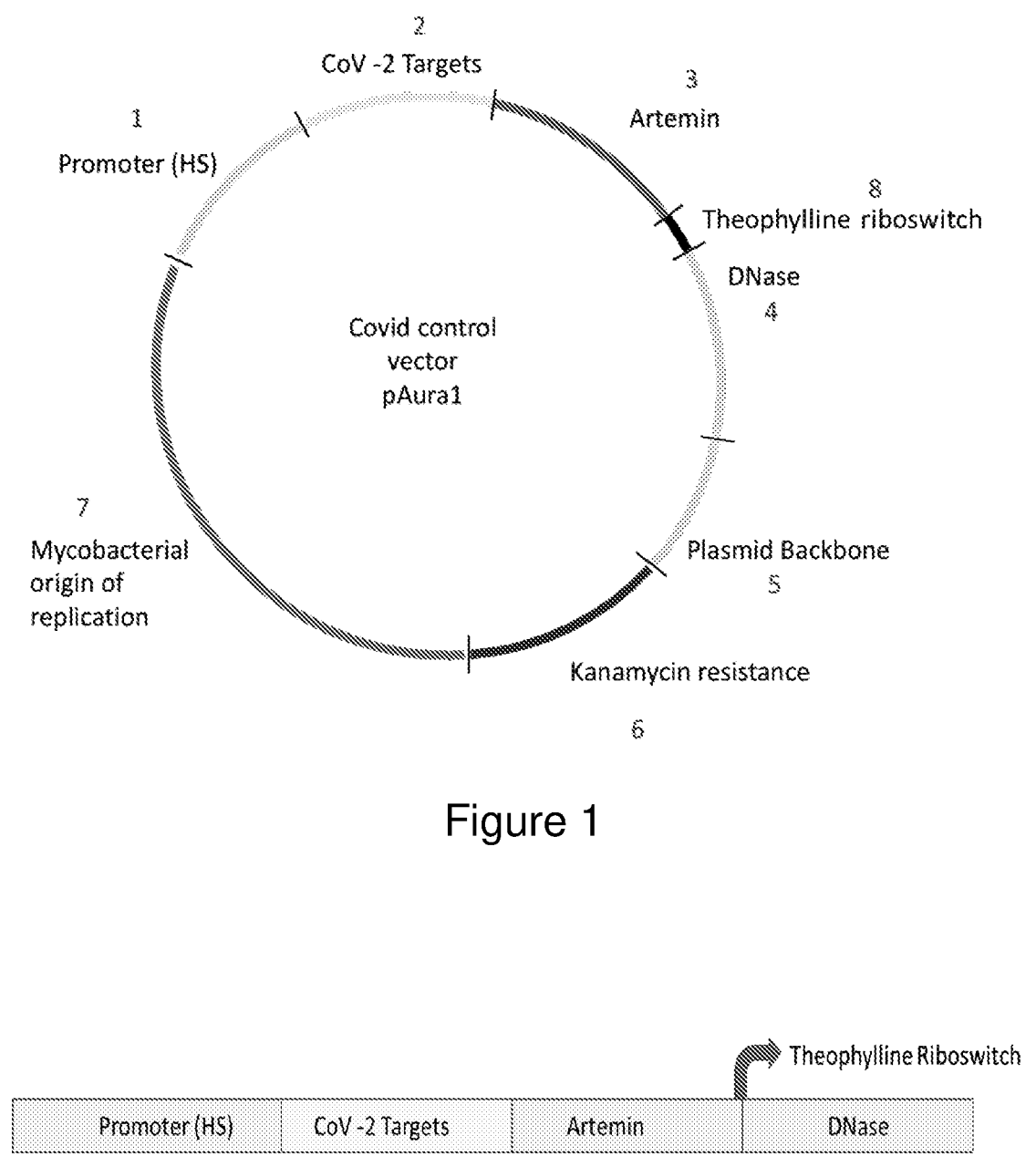

FIG. 1: Plasmid map for covid-19 control. Mycobacterium smegmatis cells were transformed using a plasmid comprising elements 1 to 8 as shown. Numbers indicate the different genetic elements encoded by the plasmid: 1) promoter; 2) at least one CoV-2 target; 3) artemin; 4) DNAse; 5) plasmid backbone allowing for plasmid replication with a standard pUC *Escherichia coli* replicon; 6) kanamycin resistance; 7) mycobacterial origin of replication; and 8) theophylline riboswitch.

FIG. 2: The SARS-CoV-2 DNA cassette for mimicking the diagnostic profile of the clinical pathogen.

FIG. 4: Nucleotide sequence of the expression cassette for targets RdRp1, RdRp2, N protein and E protein (SEQ ID NO:14).

FIG. 5: Nucleotide sequence of the expression cassette for targets Spike protein and ORF1lab 5' region (SEQ ID NO:15).

FIG. 6: Nucleotide sequence of RNA expression product for targets RdRp1, RdRp2, N protein and E protein (SEQ ID NO:16).

FIG. 7: Nucleotide sequence of RNA expression product for targets Spike protein and ORF1lab 5' region (SEQ ID NO:17).

SEQUENCE LISTING

Figure 3:
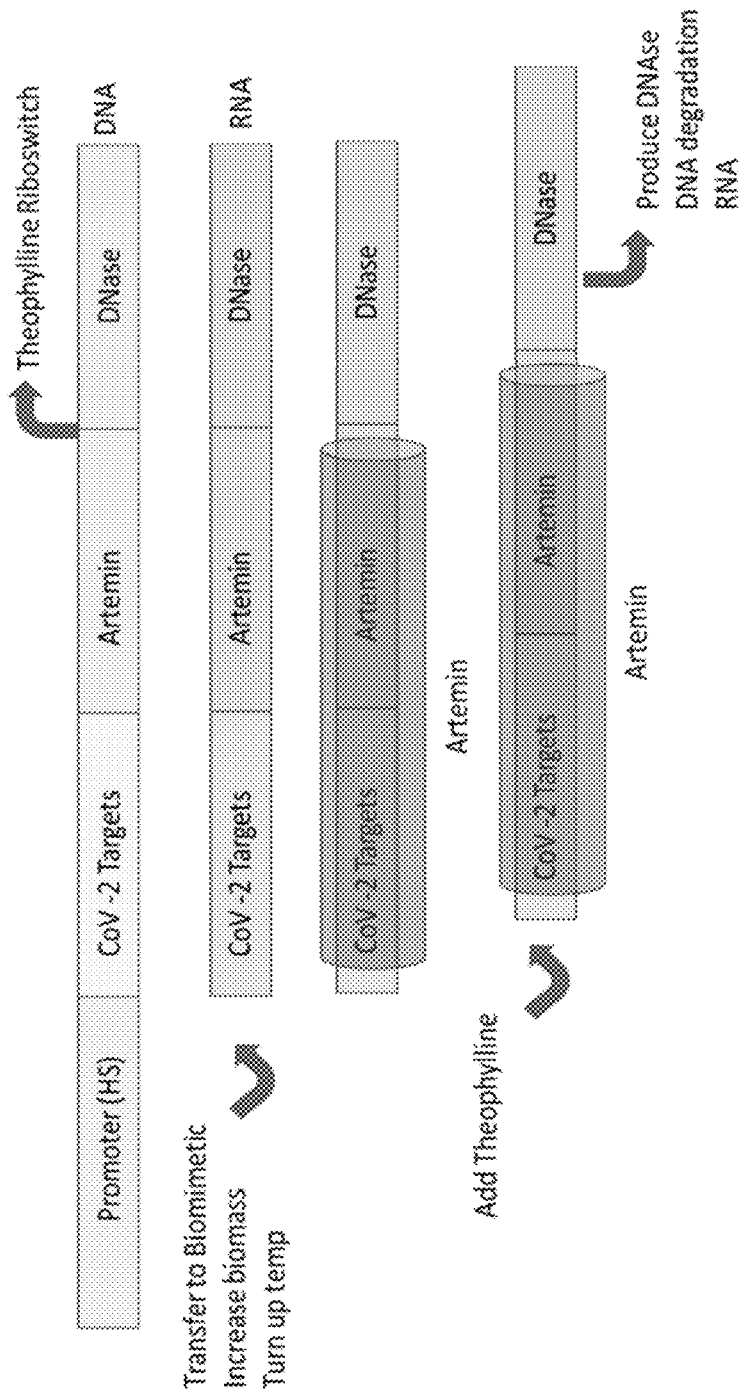
FIG. 3: RNA expression of the SARS-CoV-2 DNA cassette, the artemin riboswitch and DNAse genes, is induced by increasing the temperature as the elements in the cassette are under the control of a mycobacterium heat responsive promoter. This results in the expression of an RNA cassette comprising the SARS-CoV-2 target nucleic acids, artemin, the theophylline riboswitch and the DNAse. The artemin stabilises the SARS-CoV-2 targets nucleic acids. Thereafter, DNAse translation into protein is induced by the addition of theophylline and the DNA is degraded.

The nucleic acid sequences listed in the accompanying sequence listing are shown using standard letter abbreviations for nucleotide bases. It will be understood by those of skill in the art that only one strand of each nucleic acid sequence is shown, but that the complementary strand is included by any reference to the displayed strand. In the accompanying sequence listing:

SEQ ID NO:1—Nucleotide sequence of the Hsp60 promoter
SEQ ID NO:2—Nucleotide sequence of SARS CoV-2 target RdRp1
SEQ ID NO:3—Nucleotide sequence of SARS CoV-2 target RdRp2
SEQ ID NO:4—Nucleotide sequence of SARS CoV-2 target N protein
SEQ ID NO:5—Nucleotide sequence of SARS CoV-2 target E protein
SEQ ID NO:6—Nucleotide sequence of SARS CoV-2 target Spike protein
SEQ ID NO:7—Nucleotide sequence of SARS CoV-2 target ORF1lab 5' region
SEQ ID NO:8—Nucleotide sequence of artemin
SEQ ID NO:9—Nucleotide sequence of DNAse
SEQ ID NO:10—Nucleotide sequence of plasmid backbone
SEQ ID NO:11—Nucleotide sequence of kanamycin resistance cassette
SEQ ID NO:12—Nucleotide sequence of mycobacterial origin of replication
SEQ ID NO:13—Nucleotide sequence of theophylline riboswitch
SEQ ID NO:14—Nucleotide sequence of the expression cassette for targets RdRp1, RdRp2, N protein and E protein
SEQ ID NO:15—Nucleotide sequence of the expression cassette for targets Spike protein, ORF1lab 5' region, RdRp1, RdRp2, N protein and E protein
SEQ ID NO:16—Nucleotide sequence of RNA expression product for targets RdRp1, RdRp2, N protein and E protein
SEQ ID NO:17—Nucleotide sequence of RNA expression product for targets Spike protein, ORF1lab 5' region, RdRp1, RdRp2, N protein and E protein
SEQ ID NO:18—Nucleotide Sequence of fragment 1 of SARS-CoV-2 genome
SEQ ID NO:19—Nucleotide Sequence of fragment 2 of SARS-CoV-2 genome
SEQ ID NO:20—Nucleotide Sequence of fragment 3 of SARS-CoV-2 genome
SEQ ID NO:21—Nucleotide Sequence of fragment 4 of SARS-CoV-2 genome
SEQ ID NO:22—Nucleotide Sequence of fragment 5 of SARS-CoV-2 genome
SEQ ID NO:23—Nucleotide Sequence of fragment 6 of SARS-CoV-2 genome
SEQ ID NO:24—Nucleotide Sequence of fragment 7 of SARS-CoV-2 genome
SEQ ID NO:25—Nucleotide Sequence of fragment 8 of SARS-CoV-2 genome
SEQ ID NO:26—Nucleotide Sequence of fragment 9 of SARS-CoV-2 genome
SEQ ID NO:27—Nucleotide Sequence of fragment 10 of SARS-CoV-2 genome
SEQ ID NO:28—Nucleotide Sequence of fragment 11 of SARS-CoV-2 genome.

DETAILED DESCRIPTION OF THE INVENTION

The present invention will now be described more fully hereinafter with reference to the accompanying drawings, in which some, but not all embodiments of the invention are shown.

The invention as described should not be limited to the specific embodiments disclosed and modifications and other embodiments are intended to be included within the scope of the invention. Although specific terms are employed herein, they are used in a generic and descriptive sense only and not for purposes of limitation.

As used throughout this specification and in the claims which follow, the singular forms "a", "an" and "the" include the plural form, unless the context clearly indicates otherwise.

The terminology and phraseology used herein is for the purpose of description and should not be regarded as limiting. The use of the terms "comprising", "containing", "having" and "including" and variations thereof used herein, are meant to encompass the items listed thereafter and equivalents thereof as well as additional items.

The invention relates to a recombinant bacterium that mimics the diagnostic profile of one or more single stranded RNA diagnostic targets of interest that are detected by a molecular diagnostic assay, in particular a single stranded RNA virus, including SARS-CoV-2. The recombinant bacterium of the invention is based on a non-pathogenic bacterium that has a modified genetic content containing a target nucleic acid from a single stranded RNA diagnostic target, such as an ssRNA virus like SARS-CoV-2, wherein the target nucleic acid is detected by a molecular diagnostic assay. The approach of the inventors is to first culture the biomimetic *Mycobacterium smegmatum* comprising the DNA cassette to increase the biomass, then transfer to a high temperature to increase RNA expression of the single stranded RNA targets, and the artemin and DNAse genes. Once the artemin is expressed, it binds and stabilizes the RNA of the targets. Thereafter, theophylline is added to induce production of the DNAse, and the temperature is raised to activate the DNase. Once the DNAse is expressed it degrades the DNA, leaving only RNA in an encapsulated bacterial cell. This serves as a safe, non-infectious control organism for proficiency testing of molecular diagnostic assays for the single stranded RNA diagnostic targets, for example SARS-CoV-2 diagnostics. The process is outlined in FIG. 3.

The recombinant bacterium of the present invention may be used as both an internal and external control for single stranded RNA diagnostic assays. Specifically, the recombinant *Mycobacterium smegmatis* of the present invention is used as an internal control for measuring efficacy of RNA extraction and to detect the presence of inhibitors of PCR, however, it is most importantly a positive control for the binding of the specific probes employed in the diagnostic assays, i.e. whether the test is fit for purpose, as well as of the handling of the sample by laboratory staff. In this way, the present invention represents an external control used to determine quality assurance of the testing program. Further, according to the present invention, the clinical sample is not spiked with the recombinant bacterium of the invention, rather the two samples are tested side-by-side.

The controls described herein focus on those required for test validation and proficiency testing and include validation controls, proficiency testing controls and external quality assessment (EQA) controls. Validation controls are required for two main reasons (i) when a test is conducted for the first time in a reference laboratory or a network of reference laboratories, positive and negative controls are required to determine if the test is fit-for-purpose and produces the correct result and (ii) as new testing kits emerge in the market, their utility can only be assessed by using controls that best mimic clinical specimens. Proficiency testing controls are useful as Covid-19 testing is rolled out to different reference labs, it becomes important to assess the proficiency of the lab testing system, including staff and infrastructure, in executing test procedures. For this, controlled specimens, where the expected outcome of the test result is known, are necessary. Finally, EQA controls are required in order to determine if laboratories are handling specimens correctly and executing test procedures appropriately. Again, it is important to develop controls that mimic clinical specimens.

In the case of viruses, a clinical specimen for the molecular diagnostic assay would comprise intact virus, for example SARS-CoV-2. As this poses numerous safety concerns, laboratory products that best mimic these specimens are more appropriate. For genetic testing, the viral RNA (inactivate) can serve as an appropriate control. Alternatively, plasmid DNA (naked or encapsulated) can serve as controls. In the case of serological tests, live viral particles, or suspensions that most closely mimic this are required.

The term "recombinant" means that something has been recombined. When used with reference to a nucleic acid construct, the term refers to a molecule that comprises nucleic acid sequences that are joined together or produced by means of molecular biological techniques. Recombinant nucleic acid constructs may include a nucleotide sequence which is ligated to, or is manipulated to become ligated to, a nucleic acid sequence to which it is not ligated in nature, or to which it is ligated at a different location in nature. Accordingly, a recombinant nucleic acid construct indicates that the nucleic acid molecule has been manipulated using genetic engineering, i.e. by human intervention. Recombinant nucleic acid constructs may be introduced into a host cell by transformation and preferably by transformation with a vector.

The term "vector" refers to a means by which polynucleotides or gene sequences can be introduced into a cell. There are various types of vectors known in the art including plasmids, viruses, bacteriophages and cosmids. Generally, polynucleotides or gene sequences are introduced into a vector by means of recombinant DNA technology.

The recombinant bacterium of the invention is preferably a recombinant *Mycobacterium smegmatis* bacterium. *Mycobacterium smegmatis* is preferred as this bacterium is non-pathogenic and does not require high levels of biosafety for its propagation. It will be appreciated that the recombinant bacterium of the invention preferably has a modified genetic content containing a target nucleic acid which is detected by a diagnostic assay. However, due to the incorporation of the target nucleic acid sequence of the single stranded RNA diagnostic target that is detected by the diagnostic assay, the recombinant *Mycobacterium smegmatis* mimics the diagnostic profile of the single stranded RNA diagnostic target, for example a virus, including SARS-CoV-2 pathogen.

As used herein the terms "nucleic acid", "nucleic acid molecule" or "polynucleotide" encompass both ribonucleotides (RNA) and deoxyribonucleotides (DNA), including cDNA, genomic DNA, and synthetic DNA. A nucleic acid may be double-stranded or single-stranded. Where the nucleic acid is single-stranded, the nucleic acid may be the sense strand or the antisense strand. A nucleic acid molecule may be any chain of two or more covalently bonded nucleotides, including naturally occurring or non-naturally occurring nucleotides, or nucleotide analogs or derivatives. The term "DNA" refers to a sequence of two or more covalently bonded, naturally occurring or modified deoxyribonucleotides.

The recombinant *Mycobacterium smegmatis* as described herein may be used as a control for the detection of in a diagnostic assay for a single stranded RNA virus, such as SARS-CoV-2. Further, the recombinant bacterium may be used as a control for the detection of other RNA targets in a molecular diagnostic assay based on the detection using probes or amplification of single stranded RNA, such as the BRCA-ABL human ss-mRNA Particularly, the recombinant Mycobacterium smegmatis may be used for the calibration of diagnostic devices used to diagnose a single stranded RNA virus, such as SARS-CoV-2, in a subject and for active surveillance monitoring of single stranded RNA viral infections, including SARS-CoV-2 infections. For example, the recombinant *Mycobacterium smegmatis* may be used as a control in the GeneXpert® system, Thermo Fisher, Cobas SARS-CoV-2, Abbot Realtime SARS-CoV-2, BGI, CDC, SeeGene, Tib Mol Bio and Ultragene ABL assays.

In one embodiment of the invention the recombinant *Mycobacterium smegmatis* is used for the purposes of external quality assessment (EQA) of the GeneXpert® modular cartridge system. The GeneXpert® system relies on the use of complementary nucleic acid probes to detect the presence or absence of the target single stranded RNA, for example a SARS-CoV-2 nucleic acid or even the BRCA-ABL human ss-mRNA. The present invention includes the same target nucleic acids as the GeneXpert® system using the same complementary nucleic acid probes.

As used herein, the term "mimics the diagnostic profile" means that the recombinant bacterium has the same diagnostic profile as the clinical sample containing the single stranded RNA, indistinguishably, and with the same specificity in an assay, when using the same detection probes or primers for both the clinical sample and the recombinant bacterium. This diagnostic profile that is mimicked may be, for example, a GeneXpert® assay readout.

As used herein the term "single stranded RNA diagnostic target" refers to a target region of single stranded RNA that is detected by a molecular diagnostic assay, in particular a nucleic acid assay that directly detects the presence of the RNA using either a probe or primer that specifically binds the region of single stranded RNA. Preferably the assay is an RT-PCR assay.

The term "complementary" refers to two nucleic acids molecules, e.g., DNA or RNA, which are capable of forming Watson-Crick base pairs to produce a region of double-strandedness between the two nucleic acid molecules. It will be appreciated by those of skill in the art that each nucleotide in a nucleic acid molecule need not form a matched Watson-Crick base pair with a nucleotide in an opposing complementary strand to form a duplex. One nucleic acid molecule is thus "complementary" to a second nucleic acid molecule if it hybridizes, under conditions of high stringency, with the second nucleic acid molecule. A nucleic acid molecule according to the invention includes both complementary molecules.

As used herein a "substantially identical" sequence is an amino acid or nucleotide sequence that differs from a reference sequence only by one or more conservative substitutions, or by one or more non-conservative substitutions, deletions, or insertions located at positions of the sequence that do not destroy or substantially reduce the binding of one or more of the probes for the targets in the molecular diagnostic assay. Alignment for purposes of determining percent sequence identity can be achieved in various ways that are within the knowledge of those with skill in the art. These include using, for instance, computer software such as ALIGN, Megalign (DNASTAR), CLUSTALW or BLAST software. Those skilled in the art can readily determine appropriate parameters for measuring alignment, including any algorithms needed to achieve maximal alignment over the full length of the sequences being compared. In one embodiment of the invention there is provided for a polynucleotide sequence that has at least about 80% sequence identity, at least about 90% sequence identity, or even greater sequence identity, such as about 95%, about 96%, about 97%, about 98% or about 99% sequence identity to the sequences described herein.

Alternatively, or additionally, two nucleic acid sequences may be "substantially identical" if they hybridize under high stringency conditions. The "stringency" of a hybridisation reaction is readily determinable by one of ordinary skill in the art, and generally is an empirical calculation which depends upon probe length, washing temperature, and salt concentration. In general, longer probes required higher temperatures for proper annealing, while shorter probes require lower temperatures. Hybridisation generally depends on the ability of denatured DNA to re-anneal when complementary strands are present in an environment below their melting temperature. A typical example of such "stringent" hybridisation conditions would be hybridisation carried out for 18 hours at 65° C. with gentle shaking, a first wash for 12 min at 65° C. in Wash Buffer A (0.5% SDS; 2×SSC), and a second wash for 10 min at 65° C. in Wash Buffer B (0.1% SDS; 0.5% SSC).

Herein, the inventors have generated strains of a non-pathogenic *Mycobacterium smegmatis* comprising a plasmid that includes target nucleic acids of diagnostic RT-PCR based tests inserted into the plasmid.

The following examples are offered by way of illustration and not by way of limitation.

Example 1

Bacterial Strains and Culture Conditions

All cloning was performed in Escherichia coli strain DH5α. Experiments were performed in Mycobacterium smegmatis strain mc$^2$155. Nucleic acid sequence inserts used in the constructs are listed in Table 1. The plasmid backbone and the kanamycin resistance cassette were purchased as synthetic DNA fragments from GenScript™.

TABLE 1

Nucleic acid sequence inserts used

| Sequence Element | Nucleic acid sequence |
|---|---|
| Hsp60 promoter (SEQ ID NO: 1) | GTTAACACTAGTTGATTAGCTAAGCAGAAGGCCATCCTGACGGAT GGCCTTTTTGCGTTTAATACTGTTTAAACCTCTAGAGGTGTGGTA GCCGATGCCGGTGTTGGCGCCGGTGACCACAACGACGCGCCCG CTTTGATCGGGGACGTCTGCGGCCGACCATTTACGGGTCTTGTT |

TABLE 1-continued

Nucleic acid sequence inserts used

| Sequence Element | Nucleic acid sequence |
|---|---|
| | GTCGTTGGCGGTCATGGGCCGAACATACTCACCCGGATCGGAG<br>GGCCGAGGACAAGGTCGAACGAGGGGCATGACCCGGTGCGGG<br>GCTTCTTGCACTCGGCATAGGCGAGTGCTAAGAATAACGTTGGC<br>ACTCGCGACCGGTGAGTGCTAGGTCGGGACGGTGAGGCCAGGC<br>CCGTCGTCGCAGCGAGTGGCAGCGAGGACAACTTGAGCCGTCC<br>GTCGCGGGCACTGCGCCCGGCCAGCGTAAGTAGCGGGGTTGCC<br>GTCACCCGGTGACCCCCGTTTCATCCCCGATCCGCATGC |
| SARS CoV-2 target RdRp1 (SEQ ID NO: 2) | CTCTTATTGTAACAGCTTTAAGGGCCAATTCTGCTGTCAAATTACA<br>GAATAATGAGCTTAGTCCTGTTGCACTACGACAGATGTCTTGTGC<br>TGCCGGTACTACACAAACTGCTTGCACTGATGACAATGCGTTAGC<br>TTACTACAACACAACAAAGGGAGGTAGGTTTGTACTTGCACTGTT<br>ATCCGATTTACAGGATTTGAAATGGGCT |
| SARS CoV-2 target RdRp2 (SEQ ID NO: 3) | GAAATGCTGGTATTGTTGGTGTACTGACATTAGATAATCAAGATC<br>TCAATGGTAACTGGTATGATTTCGGTGATTTCATACAAACCACGC<br>CAGGTAGTGGAGTTCCTGTTGTAGATTCTTATTATTCATTGTTAAT<br>GCCTATATTAACCTTGACCAGGGCTTTAACTGCAGAGTCACATGT<br>TGACACTGACTTAACAAAGCCTTACA |
| SARS CoV-2 target N protein (SEQ ID NO: 4) | TTTAGATTTCATCTAAACGAACAAACTAAAATGTCTGATAATGGAC<br>CCCAAAATCAGCGAAATGCACCCCGCATTACGTTTGGTGGACCC<br>TCAGATTCAACTGGCAGTAACCAGAATGGAGAACGCAGTGGGGC<br>GCGATCAAAACAACGTCGGCCCCAAGGTTTACCCAATAATACTGC<br>GTCTTGGTTCACCGCTCTCACTCAACATGGCAAGGAAGACCTTAA<br>ATTCCCTCGAGGACAAGGCGTTCCAATTAACACCAATAGCAGTCC<br>AGATGACCAAATTGGCTACTACCGAAGAGCTACCAGACGAATTC<br>GTGGTGGTGACGGTAAAATGAAAGATCTCAGTCCAAGATGGTATT<br>TCTACTACCTAGGAACTGGGCCAGAAGCTGGACTTCCCTATGGT<br>GCTAACAAAGACGGCATCATATGGGTTGCAACTGAGGGAGCCTT<br>GAATACACCAAAAGATCACATTGGCACCCGCAATCCTGCTAACAA<br>TGCTGCAATCGTGCTACAACTTCCTCAAGGAACAACATTGCCAAA<br>AGGCTTCTACGCAGAAGGGAGCAGAGGCGGCAGTCAAGCCTCTT<br>CTCGTTCCTCATCACGTAGTCGCAACAGTTCAAGAAATTCAACTC<br>CAGGCAGCAGTAGGGGAACTTCTCCTGCTAGAATGGCTGGCAAT<br>GGCGGTGATGCTGCTCTTGCTTTGCTGCTGCTTGACAGATTGAA<br>CCAGCTTGAGAGCAAAATGTCTGGTAAAGGCCAACAACAACAAG<br>GCCAAACTGTCACTAAGAAATCTGCTGCTGAGGCTTCTAAGAAGC<br>CTCGGCAAAAACGTACTGCCACTAAAGCATACAATGTAACACAAG<br>CTTTCGGCAGACGTGGTCCAGAACAAACCCAAGGAAATTTTGGG<br>GACCAGGAACTAATCAGACAAGGAACTGATTACAAACATTGGCC<br>GCAAATTGCACAATTTGCCCCCAGCGCTTCAGCGTTCTTCGGAAT<br>GTCGCGCATTGGCATGGAAGTCACACCTTCGGGAACGTGGTTGA<br>CCTACACAGGTGCCATCAAATTGGATGACAAAGATCCAAATTTCA<br>AAGATCAAGTCATTTTGCTGAATAAGCATAT |
| SARS CoV-2 target E protein (SEQ ID NO: 5) | CTCATTCGTTTCGGAAGAGACAGGTACGTTAATAGTTAATAGCGT<br>ACTTCTTTTTCTTGCTTTCGTGGTATTCTTGCTAGTTACACTAGCC<br>ATCCTTACTGCGCTTCGATTGTGTGCGTACTGCTGCAATATTGTT<br>AACGTGAGTCTTGTAAAACCTTCTTTTTACGTTTACTCTCGTGTTA<br>AAAATCTGAATTCTTCTAGAGTTCCTGATCTTCTGGTCTAA |
| SARS CoV-2 target Spike protein (SEQ ID NO: 6) | AAATTGATTGCCAACCAATTTAATAGTGCTATTGGCAAAATTCAAG<br>ACTCACTTTCTTCCACAGCAAGTGCACTTGGAAAACTTCAAGATG<br>TGGTCAACCAAAATGCACAAGCTTTAAACACGCTTGTTAAACAAC<br>TTAGCTCCAATTTTGGTGCAATTTCAAGTGTTTTAAATGATATCCT<br>TTCACGTCTTGACAAAGTTGAGGCTGAAGTGCAAATTGATAGGTT<br>GATCACAGGCAGACTTCAAAGTTTGCAGACATATGTGACTCAACA<br>ATTAATTAGAGCTGCAGAAATCAGAGCTTCTGCTAATCTTGCTGC<br>TACTAAAATGT |
| SARS CoV-2 target ORF1ab 5' region (SEQ ID NO: 7) | ACTTGAACAGCCCTATGTGTTCATCAAACGTTCGGATGCTCGAAC<br>TGCACCTCATGGTCATGTTATGGTTGAGCTGGTAGCAGAACTCGA<br>AGGCATTCAGTACGGTCGTAGTGGTGAGACACTTGGTGTCCTTG<br>TCCCTCATGTGGGCGAAATACCAGTGGCTTACCGCAAGGTTCTT<br>CTTCGTAAGAACGGTAATAAAGGAGCTGGTGGCCATAGTTACGG<br>CGCCGATCTAAAGTCATTTGACTTAGGCGACGAGCTTGGCACTG<br>ATCCTTATGAAGATTTTCAAGAAAACTGGAACACTAAACATAGCA<br>GTGGTGTTACCCGTGAACTCATGCGTGAGCTTAACGGAGGGGCA<br>TACACTCGCTATGTCGATAACAACTTCTGTGGCCCTGATGGCTAC |
| Artemin (SEQ ID NO: 8) | AGGAAGGAATGTACATATGGCGACCGAGGGCGCGCGCAACATC<br>GGCCAGTCGGCCCCGGAGGGCAAGGTGCAGATGGACTGCCCGT<br>CGCGCCACAACTTCGACCCGGAGTGCGAGAAGGCGTTTGTGGA<br>GCACATCCACCTTGAGCTGGCCTCGTCGTACCACGCATGGTCGA |

TABLE 1-continued

Nucleic acid sequence inserts used

| Sequence Element | Nucleic acid sequence |
|---|---|
| | TGTGGGCCTTCTACGCCCGCGACTGCAAGGCCGCCGTGGGCAT<br>GACCCGCCTGTGCGAGTGGGCCTCGCACGTCTCGGCCCAGCGC<br>GCCCGCCGCATGGCCGCCTACGTGCTGACCCGCGGCGGCCACG<br>TGGACTACAAGGAGATCCCGGCCCCGAAGAAGCAGGGCTGGGA<br>CAACTTCGAGGACGCCTTCTCGCACTGCGTGGCGAACAAGAAGC<br>GCATCCTGACCTCGCTCCAGTCGCTGTACCAGTGCTGCCAGTCG<br>AAGGACGCCCACTGCTCGAACTTCATCCAGACCGACATGATGGA<br>CGAGGTGATCGCGTGGAACAAGTTTCTGTCGGACTGCCTGTCGA<br>ACCTGCACTGCATCGGCTCGCAGGGCATGGGACCGTGGGTGTT<br>CGACCGCTGGCTGGCCCGCATCGTGATGTCGAAGTTCAAGCACC<br>CGAAGATCCCGTCGCTCTCGACCTCGGACCTAGAGTCGAACATC<br>CCGAACGAGCTGTTCGACGCCGAGGGCGACATGGTGCGCGCCA<br>TCAAGAAGCTGGACTACAAGGACCATGACGGTGACTATAAAGAT<br>CACGATATAGATTACAAGGATGACGATGACAAGTGA |
| DNAse<br>(SEQ ID NO: 9) | ATGCATACCATCTACCGCATCGAGAAGAAGGAGAACTACGTGGT<br>GCTGGACAAGGGCTTCCTGCACGACCGCGAGCTGTCGTGGCAG<br>GCTAAGGGCCTGCTGGCCTTCATGCTGTCGATGCCGAACGACTG<br>GGTGTTCAACATGAAGGACCTCCAGAACCGCTCGAAGAACGGTC<br>GCGACGCCACCTACCGCATTATGAAGGAGCTGATCGAGGCCGG<br>CTACGTGACCCGCGTGGAGAACCGCGACGGCGGCAAGTTCGGC<br>AAGGTGGAGTACGTGGTCCACGAGGTGAAGCAGTCGCCGCACA<br>CCGAGTCGCCGGACACCGTGCCGCCCTGCACCGAGAACCCGTA<br>CCCCGGCAACCCGTACCCCGGCAACCCGTACCCGGAGAACCCG<br>CCGCTGCTGAACAACAACAACACCAACTACAAGAACACCAACAAC<br>GACGACGACAACAAGGACCGCCCGAAGACCAACTCGCTGAACG<br>CCTTTCGCTTCTACGAGGAGAACTTCCAGCCGACCCTGTCGTCG<br>GTGGACATCGAGATCCTGAACTACTGGCTGGACCGCTTCCCGGA<br>GGAGATCGTGCTGTGCGCCATGCGGAAGGCCCTAGAGCAGAAC<br>GTGCGCTCGATCAAGTACATCGACCGCATCCTTGCCAACTGGGA<br>GATGCAGAAGGTGCAGACCCTTGAGGACGTGGCCCGCCTCGAC<br>CGCCAGTACGAGCTGGAGAAGCAGGCCCGCCAGAAGCGCGGCG<br>GCGTGGTGAACGGCTCGGTCCACCAGCACCGCGGCTCGGACGG<br>TCGCTCGACGAAGGAGGACGAGCGCATCTCGCACTACGAGCCG<br>GGCAAGTGGGACGACGTGGACATCTCGCTGGACGGCCTGCTGC<br>ACCATCACCACCATCACTGA |
| Plasmid<br>backbone<br>(SEQ ID NO: 10) | GATCTGCATTAATGAATCGGCCAACGCGCGGGGAGAGGCGGTTT<br>GCGTATTGGGCGCTCTTCCGCTTCCTCGCTCACTGACTCGCTGC<br>GCTCGGTCGTTCGGCTGCGGCGAGCGGTATCAGCTCACTCAAAG<br>GCGGTAATACGGTTATCCACAGAATCAGGGGATAACGCAGGAAA<br>GAACATGTGAGCAAAAGGCCAGCAAAAGGCCAGGAACCGTAAAA<br>AGGCCGCGTTGCTGGCGTTTTTCCATAGGCTCCGCCCCCCTGAC<br>GAGCATCACAAAAATCGACGCTCAAGTCAGAGGTGGCGAAACCC<br>GACAGGACTATAAAGATACCAGGCGTTTCCCCCTGGAAGCTCCC<br>TCGTGCGCTCTCCTGTTCCGACCCTGCCGCTTACCGGATACCTG<br>TCCGCCTTTCTCCCTTCGGGAAGCGTGGCGCTTTCTCATAGCTCA<br>CGCTGTAGGTATCTCAGTTCGGTGTAGGTCGTTCGCTCCAAGCT<br>GGGCTGTGTGCACGAACCCCCCGTTCAGCCCGACCGCTGCGCC<br>TTATCCGGTAACTATCGTCTTGAGTCCAACCCGGTAAGACACGAC<br>TTATCGCCACTGGCAGCAGCCACTGGTAACAGGATTAGCAGAGC<br>GAGGTATGTAGGCGGTGCTACAGAGTTCTTGAAGTGGTGGCCTA<br>ACTACGGCTACACTAGAAGAACAGTATTTGGTATCTGCGCTCTGC<br>TGAAGCCAGTTACCTTCGGAAAAAGAGTTGGTAGCTCTTGATCCG<br>GCAAACAAACCACCGCTGGTAGCGGTGGTTTTTTTGTTTGCAAGC<br>AGCAGATTACGCGCAGAAAAAAAGGATCTCAAGAAGATCCTTTGA<br>TCTTTTCTACGGGGTCTGACGCTCAGTGGAACGAAAACTCACGTT<br>AAGGGATTTTGGTCATGAGATTATCAAAAAGGATCTTCACCTAGA<br>TCCTTTTAAATTAAAAATGAAGTTTTAAATCAAGCCCAATCTGAAT<br>AATGTTACAACCAATTAACCAATTCTGA |
| Kanamycin<br>resistance gene<br>(SEQ ID NO: 11) | ATGAGCCATATTCAACGGGAAACGTCGAGGCCGCGATTAAATTC<br>CAACATGGATGCTGATTTATATGGGTATAAATGGGCTCGCGATAA<br>TGTCGGGCAATCAGGTGCGACAATCTATCGCTTGTATGGGAAGC<br>CCGATGCGCCAGAGTTGTTTCTGAAACATGGCAAAGGTAGCGTT<br>GCCAATGATGTTACAGATGAGATGGTCAGACTAAACTGGCTGAC<br>GGAATTTATGCCTCTTCCGACCATCAAGCATTTTATCCGTACTCCT<br>GATGATGCATGGTTACTCACCACTGCGATCCCCGGAAAAACAGC<br>ATTCCAGGTATTAGAAGAATATCCTGATTCAGGTGAAAATATTGTT<br>GATGCGCTGGCAGTGTTCCTGCGCCGGTTGCATTCGATTCCTGT<br>TTGTAATTGTCCTTTTAACAGCGATCGCGTATTTCGTCTCGCTCA<br>GGCGCAATCACGAATGAATAACGGTTTGGTTGATGCGAGTGATTT<br>TGATGACGAGCGTAATGGCTGGCCTGTTGAACAAGTCTGGAAAG<br>AAATGCATAAACTTTTGCCATTCTCACCGGATTCAGTCGTCACTC<br>ATGGTGATTTCTCACTTGATAACCTTATTTTTGACGAGGGGAAATT |

TABLE 1-continued

Nucleic acid sequence inserts used

| Sequence Element | Nucleic acid sequence |
|---|---|
| | AATAGGTTGTATTGATGTTGGACGAGTCGGAATCGCAGACCGATA<br>CCAGGATCTTGCCATCCTATGGAACTGCCTCGGTGAGTTTTCTCC<br>TTCATTACAGAAACGGCTTTTTCAAAAATATGGTATTGATAATCCT<br>GATATGAATAAATTGCAGTTTCATTTGATGCTCGATGAGTTTTTCT<br>AA |
| Mycobacterial origin of replication (SEQ ID NO: 12) | GGGGCCTGTAACGGCACAACGAACCGTGCAACGAGAGTGGCCA<br>CGGATGCCACCACAAGCACTACAACGGAGTTCGCCACGTACATC<br>ACCACAACCACCGATTCTGGCGGTGAGCTCCACGATATTCAGCG<br>GAAATGGCTTGGTATCGACCAAGATTCGTAGAACCCCGTCTCGT<br>CTGGCTGGTATTCAAAACGGACGCAACGAAACACGCAACGAGAC<br>AGGCATGGCCCAAACCAGAAAACTAGCGTCTACCAGGACTTTTA<br>CCTGTCCGACCCGTTGCAACGGAACCCCCCACGGAACCCCCGC<br>GACACCCGCTCCCCAATTGCGTTAGAACAGCGGTGGATTGTCGG<br>CTTCGTTGTGGGCCTTTTGAGCCGCTTCCTGTTCTGCCGCACGC<br>TCTTTCCTCGCCCGATAGCCGAGTCGCTTAACGGTGTCCAGATG<br>CAGCCCGAAATGTTTGGCCGTTTGCGGCCAAGAGTGGCCCTCGT<br>CGTCGTGATAGGCGCGGATGCGTTCGCGGCGTGCAGCCTGCTC<br>GGCGAGCCACTCGCTGCGTTCCTGCGCCACGAGCCGGACGACG<br>TGGCGTTCGGATAGTCCGGTGATTCGAGCGCCTTCGGCGGCGG<br>TCACGCGCCGCTTTTTGCGGACAGTCGGCTGCCGGTTGTAGCCG<br>TCGCTGTAGCCGTCGCTGTAGCCGTCGCTCATAGCAATGCCTCC<br>ATGGCTGACGCGGACTTTGCGCGCCGCGCAACTGTGCTCGCCG<br>CCGTGCGCGCTGCTGCGCCCTTCCGCGAGATGGCCGACTGGCG<br>CGCACTGAGTGTGGCCTCGTAGACCACGATCCCGTCCGCCCAAA<br>TGCGCGACTTGGTTGTGATCCAACGCCAAATGCTGTTGGCGATG<br>GCGCGGACCTCGCTGTCCGGTAGCGGTCCGGGACACACGTCGT<br>TGCACGGGAATTCGGCGTTTCGCGCGTGGCACTCGGCATAGATC<br>GCGCGGCCGAGTCCGTCCACGTTCCGGGTCGGCAGGTAGATCC<br>GCATGAGGGCGGGACGATAGGCCCACAACCTGACGGAATCGAA<br>CAGTGCGCAATTCCGCCCTAGCGGCGTCGGAGCCGCTTTGTACG<br>TGGTCTGCTGACGCCAGCGCGGCGGTGGCATGTTCGCGCCGAG<br>CTCGGCCTCGATGTGGCTGAGTGTGTAGAGATCTGAGTGGAGCC<br>ATTCCGTTTCCCAGGCGATGTGGCCGGGGTTTTTGGTCATGAGG<br>CCTGAGTAACTGCGGTCGCCGTCGACGGCGCGCCGAAGGCCTT<br>CGGCGCACGCCGCCATGTATGCGAGCGGCTTACGCCGCGCGTA<br>TTCGGTGCGTGGAACAGGGGCGTTGAGTGCCCACACTGCGTGT<br>GCGTGGCCGTTGGCGCGATTGCCCACGATCGCGTTGGGCAGCG<br>GATGGGACCCCCGGGCGCTGAGCGCTCGGAGCGCTGCGTCTGG<br>ATGGTCTACGTCCACGACCAGCAGGTTTGCCAGCGCTGTTGGGT<br>TCGCCTCGATGTACCGGCGGCCTAGGGCCGACGCGCGGCTTTG<br>GCGGTAGATCCCCTCGAGCAGATCGTCGCTTGCCAGCGGCCAG<br>TACGGCAGCCAGAGCTGCTCAAATTCGTCGGCGACGTGGCTCAC<br>GCTTGGTAGTAGACCACGATTAATCACCGGTGTATGGTCCGACA<br>CGAGCTCCAAGTCAGATATTTCGCTGAGGGGCCACCCCACAACT<br>GCACACTCCCCCGCTCTCCCGTCGAGCCCTGATGATGAAACACC<br>AGCGACAGCCGAGCACCCCCAACCACCTGTACCAACCAGGAGG<br>AACACATGCGTCGTTTCGAGGACGTTTCCGGGCCGCTAAGAGCC<br>GCTGTGGCGGCCGTACACGCCGCCTTAGACCCGTTAGACCCCCT<br>GCCGCCTGAATGCGCGGGTACGAGCCACACAGCACCCGAACTT<br>ACGGAGCTGGTGGGCTCACCTGGCTTTATGGCGTACGAATCGGC<br>TGTGTGCGACCTGTTGGGCGAGGTGAGATACGCGCTACTCACGC<br>TGGCAAGGGCGACACAGCCGCCCCACCGAGCCCGCACGGCCG<br>CGCGCGGTGTCAACAACCGGGTGAGTCGTGCACACCAGCAGGT<br>GTTCGAGGCTTGGCTCGAAGTGCAGGACATCGTGGCGAACGCC<br>GCCCGATGAGCCGCGCCTTACGCTGGCTGCCAGCCGTTCGCGG<br>GCTGGTTGGTGCAGCGCGTCGAGCGGTTAGAGGCCCTGCGGTG<br>TTCCACCACCGCAGGCCTCGCCCTTTTTAAGGCTGAATTTGCTTG<br>TCTCCGAATCCAACTGGCTTGTCCAAGGGTGTATCTACGCTTAGT<br>CCAAAGTTCAAACGAGGGGATTACACATGACCAACTTCGATAACG<br>TTCTCGGCTCGATCTG |
| Theophylline riboswitch (SEQ ID NO: 13) | GGTGATACCAGCATCGTCTTGATGCCCTGGCAGCACCCTGCTAA<br>GGAGGCAACAAG |

*E. coli* strains were grown at 37° C. in standard Luria Bertani (LB) or 2YT liquid medium or on solid medium (LA) supplemented with 50 μg/ml kanamycin (kan). Mycobacterium smegmatis strains were grown at 37° C. shaking in Middlebrook 7H9 liquid medium (Difco) supplemented with 0.085% NaCl, 0.2% glucose, 0.2% glycerol and 0.05% Tween80, or on Middlebrook 7H10 solid medium (Difco) supplemented with 0.085% NaCl, 0.2% glucose and 0.5% glycerol. Kanamycin was used at a concentration of 50 μg/mL kanamycin.

Cloning of Shuttle Plasmids for Integration into *Mycobacterium Smegmatis*

The following elements were cloned and prepared in *E. coli* to obtain the plasmid shown in FIG. 1:
1. Hsp60 promoter (SEQ ID NO:1): A well characterised heat responsive promoter in mycobacteria that allows for induction of high levels of messenger RNA when the bacterium is exposed to heat in the form of 42° C.
2. SARS-CoV-2 targets: pAura1 comprising the RNA-dependent RNA polymerases RdRp1 (SEQ ID NO:2) and RdRp2 (SEQ IDNO:3), the N protein (SEQ ID NO:4) and the E protein (SEQ ID NO:5). These are the regions of the viral genetic material that are targeted by diagnostic machines and tests such as the GeneXpert®.
3. Artemin (SEQ ID NO:8): An RNA binding protein that stabilizes the RNA molecule. It binds RNA and prevents it from being degraded. The sequence was obtained from the genome of *Artemia salina* (Taxonomy ID: 85549). The inclusion of the artemin protein is to facilitate stabilization of RNA at room temperature for prolonged periods of time. This allows for easier distribution and use of the controls.
4. DNAse (SEQ ID NO:9): DNAse derived from the thermophilic *Geobacillus* bacteriophage GBSV1 (Taxonomy ID: 365048). This DNAse is inactive at room temperature and at 37° C., the temperature at which the biomimetic control composition is cultured. However, when the temperature is shifted to temperatures above 55° C., with an optimum of around 60° C., the DNAse becomes active and degrades DNA. This temperature sensitivity for activity allows for condition-dependent DNA degradation, which prevents interference by DNA.
5. Plasmid backbone (SEQ ID NO:10): Contains the basic elements required for maintaining the plasmid in *E. coli* for cloning steps, including the pUC57 origin of replication.
6. Kanamycin resistance cassette (Nptll) (SEQ ID NO:11): The cassette carries the open reading frame for the kanamycin resistance gene
7. Mycobacterial origin of replication from pYUB12 (SEQ ID NO:12): Cloned from pYUB12 as an EcoRv-Hpal fragment.
8. Theophylline riboswitch (SEQ ID NO:13): This is a regulatory element that allows for translation of the RNA for the DNAse into protein. It facilitates tight regulation of the DNAse so that DNA degradation that is not regulated can be toxic to the cell during growth.

The resulting plasmid was electroporated into *M. smegmatis* $mc^2155$ by standard laboratory methods. Briefly, electrocompetent $mc^2155$ were prepared as follows: Cells were grown to log phase ($OD_{600}$ 0.5-0.9) and harvested by centrifugation (3 500 rpm, 10 min, 4° C.). The pelleted cells were then washed three times by gentle resuspension in 10 ml ice-cold 10% glycerol and cells pelleted by centrifugation between washes (3 500 rpm, 10 min, 4° C.). The cells were resuspended in an appropriate volume of ice-cold 10% glycerol and used immediately. For transformation, 400 µl of electro-competent cells were transferred to pre-chilled 0.2 cm electroporation cuvettes (Bio-Rad), together with plasmid DNA. The Gene PulserX cell (Bio-Rad) was used for electroporation set at 2.5 kV, 25 µF and 10000. Cells were immediately rescued with 1 ml of 2× TY for 3 hours or overnight at 37° C. with shaking at 100 rpm. The rescued cells were plated on Middlebrooks Medium 7H9 supplemented with glucose, NaCl and kanamycin (25 µg/mL) for maintenance of the episomal shuttle plasmid.

Cultures were grown overnight at 37° C. and once sufficiently dense ($OD_{600}$>2), the culture was transferred to 42° C. to induce expression of the SARS-CoV-2 targets, artemin and DNAse cassette (SEQ ID NO:16) and grown shaking for an additional 30 minutes. Theophylline was then added at a concentration of 2 mM for 2 hours at 37° C. The temperature was then raised to 60° C. for 30 min to induce the DNAse. Cultures were split into 22.5 ml aliquots, in 50 ml conical bottom centrifuge, and incubated at 80° C. for 70 minutes.

The cells were harvested by centrifugation at 3080×g for 10 minutes. Thereafter, the pellets were resuspended in 15 ml of 1×PBS solution with 0.05% Tween-80 and 32 ml SR buffer supplied by Cepheid® with GeneXpert® MTB/Ultra. Cells were incubated for 60 minutes at room temperature and the cells were harvested by centrifugation at 3080×g for 10 minutes. The pellets were resuspended in 45 ml of 1×PBS solution with 0.05% Tween-80. The cells were harvested by centrifugation at 3080×g for 10 minutes.

The pellets were resuspended in 15 ml of 1×PBS solution with 0.05% Tween-80. Clones were stored at 4° C. and used for analysis in standard GeneXpert® diagnostics in parallel with clinical samples.

Example 2

Analysis of Strains by Standard GeneXpert® Laboratory Diagnostics for SARS-CoV-2 Assay Single colonies of modified Mycobacterium smegmatis were picked and resuspended in 500 µl of PBS and heated for 20 min at 60° C. Then, resulting liquid was added to the Xpert® Xpress SARS-CoV-2 cartridge. Three different colonies were picked and processed this way.

The digital output of the Xpert®-MTB/RIF tests was analysed and the results are shown in Table 2. All samples gave a test result of "SARS-CoV-2 POSITIVE", indicating that the non-infectious biomimetic control cells mimic the diagnostic profile of SARS-CoV-2.

TABLE 2

Results from the Xpert ® SARS-CoV-2 assays

| Sample | SARS-CoV-2 Detected | Probe A (E protein) | | | Probe B (N protein) | | | Probe C (SPC/Internal Control) | | |
|---|---|---|---|---|---|---|---|---|---|---|
| | | $C_t$ | End | | $C_t$ | End | | $C_t$ | End | |
| C12 | YES | 27.4 | 435 | + | 29.5 | 275 | + | 28.1 | 386 | N/A |
| BN2 | YES | 27.6 | 467 | + | 29.6 | 300 | + | 28.3 | 370 | N/A |
| C13 | YES | 23.2 | 440 | + | 25.1 | 294 | + | 28.1 | 435 | N/A |

Example 3

Development of SARS-CoV-2 Genome Library for Use as Nucleic Acid Sequence Inserts in the Diagnostic Control Constructs In order to ensure that SARS-CoV-2 targets could span the entire SARS-CoV-2 genome, a library of the whole SARS-CoV-2 genome was constructed. The constructed genome includes 11 fragments as shown in Table 3 below.

Briefly, the genomic RNA was obtained by culture in a BSLIII facility, by tissue culture of the virus in the Chimpanzee Vero cell line. Eleven 3 kbp fragments were obtained by reverse transcription to generate cDNA product. PCR of the cDNA was performed to obtain dsDNA product, which was captured into *E. coli* replicating plasmid. To cover the entire 30 kbp genome, 11 fragments were designed to allow for overlap between the fragments, thereby ensuring coverage in case the region of interest should lie between fragments.

Any target of interest may be cloned from the library into *M. smegmatis* using the method described in Example 1 above.

TABLE 3

SARS-CoV-2 genome fragments.

| SEQ ID NO | Nucleotide Sequence |
|---|---|
| SEQ ID NO: 18 | ATTAAAGGTTTATACCTTCCCAGGTAACAAACCAACCAACTTTCGATCTC<br>TTGTAGATCTGTTCTCTAAACGAACTTTAAAATCTGTGTGGCTGTCACTCGGCTGCATGC<br>TTAGTGCACTCACGCAGTATAATTAATAACTAATTACTGTCGTTGACAGGACACGAGTAA<br>CTCGTCTATCTTCTGCAGGCTGCTTACGGTTTCGTCCGTGTTGCAGCCGATCATCAGCAC<br>ATCTAGGTTTCGTCCGGGTGTGACCGAAAGGTAAGATGGAGAGCCTTGTCCCTGGTTTCA<br>ACGAGAAAACACACGTCCAACTCAGTTTGCCTGTTTTACAGGTTCGCGACGTGCTCGTAC<br>GTGGCTTTGGAGACTCCGTGGAGGAGGTCTTATCAGAGGCACGTCAACATCTTAAAGATG<br>GCACTTGTGGCTTAGTAGAAGTTGAAAAAGGCGTTTTGCCTCAACTTGAACAGCCCTATG<br>TGTTCATCAAACGTTCGGATGCTCGAACTGCACCTCATGGTCATGTTATGGTTGAGCTGG<br>TAGCAGAACTCGAAGGCATTCAGTACGGTCGTAGTGGTGAGACACTTGGTGTCCTTGTCC<br>CTCATGTGGGCGAAATACCAGTGGCTTACCGCAAGGTTCTTCTTCGTAAGAACGGTAATA<br>AAGGAGCTGGTGGCCATAGTTACGGCGCCGATCTAAAGTCATTTGACTTAGGCGACGAGC<br>TTGGCACTGATCCTTATGAAGATTTTCAAGAAAACTGGAACACTAAACATAGCAGTGGTG<br>TTACCCGTGAACTCATGCGTGAGCTTAACGGAGGGGCATACACTCGCTATGTCGATAACA<br>ACTTCTGTGGCCCTGATGGCTACCCTCTTGAGTGCATTAAAGACCTTCTAGCACGTGCTG<br>GTAAAGCTTCATGCACTTTGTCCGAACAACTGGACTTTATTGACACTAAGAGGGGTGTAT<br>ACTGCTGCCGTGAACATGAGCATGAAATTGCTTGGTACACGGAACGTTCTGAAAAGAGCT<br>ATGAATTGCAGACACCTTTTGAAATTAAATTGGCAAAGAAATTTGACACCTTCAATGGGG<br>AATGTCCAAATTTTGTATTTCCCTTAAATTCCATAATCAAGACTATTCAACCAAGGGTTG<br>AAAAGAAAAAGCTTGATGGCTTTATGGGTAGAATTCGATCTGTCTATCCAGTTGCGTCAC<br>CAAATGAATGCAACCAAATGTGCCTTTCAACTCTCATGAAGTGTGATCATTGTGGTGAAA<br>CTTCATGGCAGACGGGCGATTTTGTTAAAGCCACTTGCGAATTTTGTGGCACTGAGAATT<br>TGACTAAAGAAGGTGCCACTACTTGTGGTTACTTACCCCAAAATGCTGTTGTTAAAATTT<br>ATTGTCCAGCATGTCACAATTCAGAAGTAGGACCTGAGCATAGTCTTGCCGAATACCATA<br>ATGAATCTGGCTTGAAAACCATTCTTCGTAAGGGTGGTCGCACTATTGCCTTTGGAGGCT<br>GTGTGTTCTCTTATGTTGGTTGCCATAACAAGTGTGCCTATTGGGTTCCACGTGCTAGCG<br>CTAACATAGGTTGTAACCATACAGGTGTTGTTGGAGAAGGTTCCGAAGGTCTTAATGACA<br>ACCTTCTTGAAATACTCCAAAAAGAGAAAGTCAACATCAATATTGTTGGTGACTTTAAAC<br>TTAATGAAGAGATCGCCATTATTTTGGCATCTTTTTCTGCTTCCACAAGTGCTTTTGTGG<br>AAACTGTGAAAGGTTTGGATTATAAAGCATTCAAACAAATTGTTGAATCCTGTGGTAATT<br>TTAAAGTTACAAAAGGAAAAGCTAAAAAAGGTGCCTGGAATATTGGTGAACAGAAATCAA<br>TACTGAGTCCTCTTTATGCATTTGCATCAGAGGCTGCTCGTGTTGTACGATCAATTTTCT<br>CCCGCACTCTTGAAACTGCTCAAAATTCTGTGCGTGTTTTACAGAAGGCCGCTATAACAA<br>TACTAGATGGAATTTCACAGTATTCACTGAGACTCATTGATGCTATGATGTTCACATCTG<br>ATTTGGCTACTAACAATCTAGTTGTAATGGCCTACATTACAGGTGGTGTTGTTCAGTTGA<br>CTTCGCAGTGGCTAACTAACATCTTTGGCACTGTTTATGAAAAACTCAAACCCGTCCTTG<br>ATTGGCTTGAAGAGAAGTTTAAGGAAGGTGTAGAGTTTCTTAGAGACGGTTGGGAAATTG<br>TTAAATTTATCTCAACCTGTGCTTGTGAAATTGTCGGTGGACAAATTGTCACCTGTGCAA<br>AGGAAATTAAGGAGAGTGTTCAGACATTCTTTAAGCTTGTAAATAAATTTTTGGCTTTGT<br>GTGCTGACTCTATCATTATTGGTGGAGCTAAACTTAAAGCCTTGAATTTAGGTGAAACAT<br>TTGTCACGCACTCAAAGGGATTGTACAGAAAGTGTGTTAAATCCAGAGAAGAAACTGGCC<br>TACTCATGCCTCTAAAAGCCCCAAAAGAAATTATCTTCTTAGAGGGAGAAACACTTCCCA<br>CAGAAGTGTTAACAGAGGAAGTTGTCTTGAAAACTGGTGATTTACAACCATTAGAACAAC<br>CTACTAGTGAAGCTGTTGAAGCTCCATTGGTTGGTACACCAGTTTGTATTAACGGGCTTA<br>TGTTGCTCGAAATCAAAGACACAGAAAAGTACTGTGCCCTTGCACCTAATATGATGGTAA<br>CAAACAATACCTTCACACTCAAAGGCGGTGCACCAACAAAGGTTACTTTTGGTGATGACA<br>CTGTGATAGAAGTGCAAGGTTACAAGAGTGTGAATATCACTTTTGAACTTGATGAAGGA<br>TTGATAAAGTACTTAATGAGAAGTGCTCTGCCTATACAGTTGAACTCGGTACAGAAGTAA<br>ATGAGTTCGCCTGTGTTGTGGCAGATGCTGTCATAAAAACTTTGCAACCAGTATCTGAAT<br>TACTTACACCACTGGGCATTGATTTAGATGAGTGGAGTATGGCTACATACTACTTATTTG<br>ATGAGTCTGGTGAGTTTAAATTGGCTTCACATATGTATTGTTCTTTCTACCCTCCAGATG<br>AGGATGAAGAAGAAGGTGATTGTGAAGAAGAAGAGTTTGAGCCATCAACT |
| SEQ ID NO: 19 | CTTCACACTCAAAGGCGGTGCACCAACAAAGGTTACTTTTGGTGATGACA<br>CTGTGATAGAAGTGCAAGGTTACAAGAGTGTGAATATCACTTTTGAACTTGATGAAGGA<br>TTGATAAAGTACTTAATGAGAAGTGCTCTGCCTATACAGTTGAACTCGGTACAGAAGTAA<br>ATGAGTTCGCCTGTGTTGTGGCAGATGCTGTCATAAAAACTTTGCAACCAGTATCTGAAT<br>TACTTACACCACTGGGCATTGATTTAGATGAGTGGAGTATGGCTACATACTACTTATTTG<br>ATGAGTCTGGTGAGTTTAAATTGGCTTCACATATGTATTGTTCTTTCTACCCTCCAGATG |

TABLE 3-continued

SARS-CoV-2 genome fragments.

| SEQ ID NO | Nucleotide Sequence |
|---|---|
| | AGGATGAAGAAGAAGGTGATTGTGAAGAAGAAGAGTTTGAGCCATCAACTCAATATGAGT |
| | ATGGTACTGAAGATGATTACCAAGGTAAACCTTTGGAATTTGGTGCCACTTCTGCTGCTC |
| | TTCAACCTGAAGAAGAGCAAGAAGAAGATTGGTTAGATGATGATAGTCAACAAACTGTTG |
| | GTCAACAAGACGGCAGTGAGGACAATCAGACAACTACTATTCAAACAATTGTTGAGGTTC |
| | AACCTCAATTAGAGATGGAACTTACACCAGTTGTTCAGACTATTGAAGTGAATAGTTTTA |
| | GTGGTTATTTAAAACTTACTGACAATGTATACATTAAAAATGCAGACATTGTGGAAGAAG |
| | CTAAAAAGGTAAAACCAACAGTGGTTGTTAATGCAGCCAATGTTTACCTTAAACATGGAG |
| | GAGGTGTTGCAGGAGCCTTAAATAAGGCTACTAACAATGCCATGCAAGTTGAATCTGATG |
| | ATTACATAGCTACTAATGGACCACTTAAAGTGGGTGGTAGTTGTGTTTTAAGCGGACACA |
| | ATCTTGCTAAACACTGTCTTCATGTTGTCGGCCCAAATGTTAACAAAGGTGAAGACATTC |
| | AACTTCTTAAGAGTGCTTATGAAAATTTTAATCAGCACGAAGTTCTACTTGCACCATTAT |
| | TATCAGCTGGTATTTTTGGTGCTGACCCTATACATTCTTTAAGAGTTTGTGTAGATACTG |
| | TTCGCACAAATGTCTACTTAGCTGTCTTTGATAAAAATCTCTATGACAAACTTGTTTCAA |
| | GCTTTTTGGAAATGAAGAGTGAAAAGCAAGTTGAACAAAAGATCGCTGAGATTCCTAAAG |
| | AGGAAGTTAAGCCATTTATAACTGAAAGTAAACCTTCAGTTGAACAGAGAAAACAAGATG |
| | ATAAGAAAATCAAAGCTTGTGTTGAAGAAGTTACAACAACTCTGGAAGAAACTAAGTTCC |
| | TCACAGAAAACTTGTTACTTTATATTGACATTAATGGCAATCTTCATCCAGATTCTGCCA |
| | CTCTTGTTAGTGACATTGACATCACTTTCTTAAAGAAAGATGCTCCATATATAGTGGGTG |
| | ATGTTGTTCAAGAGGGTGTTTTAACTGCTGTGGTATACCTACTAAAAAGGCTGGTGGCA |
| | CTACTGAAATGCTAGCGAAAGCTTTGAGAAAAGTGCCAACAGACAATTATATAACCACTT |
| | ACCCGGGTCAGGGTTTAAATGGTTACACTGTAGAGGAGGCAAAGACAGTGCTTAAAAAGT |
| | GTAAAAGTGCCTTTTACATTCTACCATCTATTATCTCTAATGAGAAGCAAGAATTCTTG |
| | GAACTGTTTCTTGGAATTTGCGAGAAATGCTTGCACATGCAGAAGAAACACGCAAATTAA |
| | TGCCTGTCTGTGTGGAAACTAAAGCCATAGTTTCAACTATACAGCGTAAATATAAGGGTA |
| | TTAAAATACAAGAGGGTGTGGTTGATTATGGTGCTAGATTTTACTTTTACACCAGTAAAA |
| | CAACTGTAGCGTCACTTATCAACACACTTAACGATCTAAATGAAACTCTTGTTACAATGC |
| | CACTTGGCTATGTAACACATGGCTTAAATTTGGAAGAAGCTGCTCGGTATATGAGATCTC |
| | TCAAAGTGCCAGCTACAGTTTCTGTTTCTTCACCTGATGCTGTTACAGCGTATAATGGTT |
| | ATCTTACTTCTTCTTCTAAAACACCTGAAGAACATTTTATTGAAACCATCTCACTTGCTG |
| | GTTCCTATAAAGATTGGTCCTATTCTGGACAATCTACACAACTAGGTATAGAATTTCTTA |
| | AGAGAGGTGATAAAAGTGTATATTACACTAGTAATCCTACCACATTCCACCTAGATGGTG |
| | AAGTTATCACCTTTGACAATCTTAAGACACTTCTTTCTTTGAGAGAAGTGAGGACTATTA |
| | AGGTGTTTACAACAGTAGACAACATTAACCTCCACACGCAAGTTGTGGACATGTCAATGA |
| | CATATGGACAACAGTTTGGTCCAACTTATTTGGATGGAGCTGATGTTACTAAAATAAAAC |
| | CTCATAATTCACATGAAGGTAAAACATTTTATGTTTTACCTAATGATGACACTCTACGTG |
| | TTGAGGCTTTTGAGTACTACCACACAACTGATCCTAGTTTTCTGGGTAGGTACATGTCAG |
| | CATTAAATCACACTAAAAAGTGGAAATACCCCACAAGTTGGTTTAACTTCTATTATAAT |
| | GGGCAGATAACAACTGTTATCTTGCCACTGCATTGTTAACACTCCAACAAATAGAGTTGA |
| | AGTTTAATCCACCTGCTCTACAAGATGCTTATTACGAGCAAGGGCTGGTGAAGCTGCTA |
| | ACTTTTGTGCACTTATCTTAGCCTACTGTAATAAGACAGTAGGTGAGTTAGGTGATGTTA |
| | GAGAAACAATGAGTTACTTGTTTCAACATGCCAATTTAGATTCTTGCAAAAGAGTCTTGA |
| | ACGTGGTGTGTAAAACTTGTGGACAACAGCAGACAACCCTTAAGGGTGTAGAAGCTGTTA |
| | TGTACATGGGCACACTTTCTTATGAACAATTTAAGAAAGGTGTTCAGATACCTTGTACGT |
| | GTGGTAAACAAGCTACAAAATATCTAGTACAACAGGAGTCACCTTTTGTTATGATGTCAG |
| | CACCACCTGCTCAGTATGAACTTAAGCATGGTACATTTACTTGTGCTAGTGAGTACACTG |
| | GTAATTACCAGTGTGGTCAC |
| SEQ ID NO: 20 | ACTTATCTTAGCCTACTGTAATAAGACAGTAGGTGAGTTAGGTGATGTTA |
| | GAGAAACAATGAGTTACTTGTTTCAACATGCCAATTTAGATTCTTGCAAAAGAGTCTTGA |
| | ACGTGGTGTGTAAAACTTGTGGACAACAGCAGACAACCCTTAAGGGTGTAGAAGCTGTTA |
| | TGTACATGGGCACACTTTCTTATGAACAATTTAAGAAAGGTGTTCAGATACCTTGTACGT |
| | GTGGTAAACAAGCTACAAAATATCTAGTACAACAGGAGTCACCTTTTGTTATGATGTCAG |
| | CACCACCTGCTCAGTATGAACTTAAGCATGGTACATTTACTTGTGCTAGTGAGTACACTG |
| | GTAATTACCAGTGTGGTCACTATAAACATATAACTTCTAAAGAAACTTTGTATTGCATAG |
| | ACGGTGCTTTACTTACAAAGTCCTCAGAATACAAAGGTCCTATTACGGATGTTTTCTACA |
| | AAGAAAACAGTTACACAACAACCATAAAACCAGTTACTTATAAATTGGATGGTGTTGTTT |
| | GTACAGAAATTGACCCTAAGTTGGACAATTATTATAAGAAAGACAATTCTTATTTCACAG |
| | AGCAACCAATTGATCTTGTACCAAACCAACCATATCCAAACGCAAGCTTCGATAATTTTA |
| | AGTTTGTATGTGATAATATCAAATTTGCTGATGATTTAAACCAGTTAACTGGTTATAAGA |
| | AACCTGCTTCAAGAGAGCTTAAAGTTACATTTTTCCCTGACTTAAATGGTGATGTGGTGG |
| | CTATTGATTATAAACACTACACACCCTCTTTTAAGAAAGGAGCTAAATTGTTACATAAAC |
| | CTATTGTTTGGCATGTTAACAATGCAACTAATAAAGCCACGTATAAACCAAATACCTGGT |
| | GTATACGTTGTCTTTGGAGCACAAAACCAGTTGAAACATCAAATTCGTTTGATGTACTGA |
| | AGTCAGAGGACGCGCAGGGAATGGATAATCTTGCCTGCGAAGATCTAAAACCAGTCTCTG |
| | AAGAAGTAGTGGAAAATCCTACCATACAGAAAGACGTTCTTGAGTGTAATGTGAAACTA |
| | CCGAAGTTGTAGGAGACATTATACTTAAACCAGCAAATAATAGTTTAAAAATTACAGAAG |
| | AGGTTGGCCACACAGATCTAATGGCTGCTTATGTAGACAATTCTAGTCTTACTATTAAGA |
| | AACCTAATGAATTATCTAGAGTATTAGGTTTGAAAACCCTTGCTACTCATGGTTTAGCTG |
| | CTGTTAATAGTGTCCCTTGGGATACTATAGCTAATTATGCTAAGCCTTTTCTTAACAAAG |
| | TTGTTAGTACAACTACTAACATAGTTACACGGTGTTTAAACCGTGTTTGTACTAATTATA |
| | TGCCTTATTTCTTTACTTTATTGCTACAATTGTGTACTTTTACTAGAAGTACAAATTCTA |
| | GAATTAAAGCATCTATGCCGACTACTATAGCAAAGAATACTGTTAAGAGTGTCGGTAAAT |
| | TTTGTCTAGAGGCTTCATTTAATTATTTGAAGTCACCTAATTTTTCTAAACTGATAAATA |
| | TTATAATTTGGTTTTTACTATTAAGTGTTTGCCTAGGTTCTTTAATCTACTCAACCGCTG |
| | CTTTAGGTGTTTTAATGTCTAATTTAGGCATGCCTTCTTACTGTACTGGTTACAGAGAAG |

TABLE 3-continued

SARS-CoV-2 genome fragments.

| SEQ ID NO | Nucleotide Sequence |
|---|---|
| | GCTATTTGAACTCTACTAATGTCACTATTGCAACCTACTGTACTGGTTCTATACCTTGTA<br>GTGTTTGTCTTAGTGGTTTAGATTCTTTAGACACCTATCCTTCTTTAGAAACTATACAAA<br>TTACCATTTCATCTTTTAAATGGGATTTAACTGCTTTTGGCTTAGTTGCAGAGTGGTTTT<br>TGGCATATATTCTTTTCACTAGGTTTTTCTATGTACTTGGATTGGCTGCAATCATGCAAT<br>TGTTTTTCAGCTATTTTGCAGTACATTTTATTAGTAATTCTTGGCTTATGTGGTTAATAA<br>TTAATCTTGTACAAATGGCCCCGATTTCAGCTATGGTTAGAATGTACATCTTCTTTGCAT<br>CATTTTATTATGTATGGAAAAGTTATGTGCATGTTGTAGACGGTTGTAATTCATCAACTT<br>GTATGATGTGTTACAAACGTAATAGAGCAACAAGAGTCGAATGTACAACTATTGTTAATG<br>GTGTTAGAAGGTCCTTTTATGTCTATGCTAATGGAGGTAAAGGCTTTTGCAAACTACACA<br>ATTGGAATTGTGTTAATTGTGATACATTCTGTGCTGGTAGTACATTTATTAGTGATGAAG<br>TTGCGAGAGACTTGTCACTACAGTTTAAAAGACCAATAAATCCTACTGACCAGTCTTCTT<br>ACATCGTTGATAGTGTTACAGTGAAGAATGGTTCCATCCATCTTTACTTTGATAAAGCTG<br>GTCAAAAGACTTATGAAAGACATTCTCTCTCTCATTTTGTTAACTTAGACAACCTGAGAG<br>CTAATAACACTAAAGGTTCATTGCCTATTAATGTTATAGTTTTTGATGGTAAATCAAAAT<br>GTGAAGAATCATCTGCAAAATCAGCGTCTGTTTACTACAGTCAGCTTATGTGTCAACCTA<br>TACTGTTACTAGATCAGGCATTAGTGTCTGATGTTGGTGATAGTGCGGAAGTTGCAGTTA<br>AAATGTTTGATGCTTACGTTAATACGTTTTCATCAACTTTTAACGTACCAATGGAAAAAC<br>TCAAAACACTAGTTGCAACTGCAGAAGCTGAACTTGCAAAGAATGTGTCCTTAGACAATG<br>TCTTATCTACTTTTATTTCAGCAGCTCGGCAAGGGTTTGTTGATTCAGATGTAGAAACTA<br>AAGATGTTGTTGAATGTCTTAAATTGTCACATCAATCTGACATAGAAGTTACTGGCGATA<br>GTTGTAATAACTATATGCTCACCTATAACAAAGTTGAAAACATGACACCCCGTGACCTTG<br>GTGCTTGTATTGACTGTAGTGCGCGTCATATTAATGCGCAGGTAGCAAAAAGTCACAACA<br>TTGCTTTGATATGGAACGTTAAAGATTTCATGTCATTGTCTGAACAACTACGAAAACAAA<br>TACGTAGTGCTGCTAAAAAGAATAACTTACCTTTTAAGTTGACATGTGCAACTACTAGAC<br>AAGTTGTTAATGTTGTAACAACAAAGATAGCACTTAAGGGTGGTAA |
| SEQ ID NO: 21 | AGTTGCAACTGCAGAAGCTGAACTTGCAAAGAATGTGTCCTTAGACAATG<br>TCTTATCTACTTTTATTTCAGCAGCTCGGCAAGGGTTTGTTGATTCAGATGTAGAAACTA<br>AAGATGTTGTTGAATGTCTTAAATTGTCACATCAATCTGACATAGAAGTTACTGGCGATA<br>GTTGTAATAACTATATGCTCACCTATAACAAAGTTGAAAACATGACACCCCGTGACCTTG<br>GTGCTTGTATTGACTGTAGTGCGCGTCATATTAATGCGCAGGTAGCAAAAAGTCACAACA<br>TTGCTTTGATATGGAACGTTAAAGATTTCATGTCATTGTCTGAACAACTACGAAAACAAA<br>TACGTAGTGCTGCTAAAAAGAATAACTTACCTTTTAAGTTGACATGTGCAACTACTAGAC<br>AAGTTGTTAATGTTGTAACAACAAAGATAGCACTTAAGGGTGGTAAAATTGTTAATAATT<br>GGTTGAAGCAGTTAATTAAAGTTACACTTGTGTTCCTTTTTGTTGCTGCTATTTTCTATT<br>TAATAACACCTGTTCATGTCATGTCTAAACATACTGACTTTTCAAGTGAAATCATAGGAT<br>ACAAGGCTATTGATGGTGGTGTCACTCGTGACATAGCATCTACAGATACTTGTTTTGCTA<br>ACAAACATGCTGATTTTGACACATGGTTTAGCCAGCGTGGTGGTAGTTATACTAATGACA<br>AAGCTTGCCCATTGATTGCTGCAGTCATAACAAGAGAAGTGGGTTTTGTCGTGCCTGGTT<br>TGCCTGGCACGATATTACGCACAACTAATGGTGACTTTTTGCATTTCTTACCTAGAGTTT<br>TTAGTGCAGTTGGTAACATCTGTTACACACCATCAAAACTTATAGAGTACACTGACTTTG<br>CAACATCAGCTTGTGTTTTGGCTGCTGAATGTACAATTTTTAAAGATGCTTCTGGTAAGC<br>CAGTACCATATTGTTATGATACCAATGTACTAGAAGGTTCTGTTGCTTATGAAAGTTTAC<br>GCCCTGACACACGTTATGTGCTCATGGATGGCTCTATTATTCAATTTCCTAACACCTACC<br>TTGAAGGTTCTGTTAGAGTGGTAACAACTTTTGATTCTGAGTACTGTAGGCACGGCACTT<br>GTGAAAGATCAGAAGCTGGTGTTTGTGTATCTACTAGTGGTAGATGGGTACTTAACAATG<br>ATTATTACAGATCTTTACCAGGAGTTTTCTGTGGTGTAGATGCTGTAAATTTACTTACTA<br>ATATGTTTACACCACTAATTCAACCTATTGGTGCTTTGGACATATCAGCATCTATAGTAG<br>CTGGTGGTATTGTAGCTATCGTAGTAACATGCCTTGCCTACTATTTTATGAGGTTTAGAA<br>GAGCTTTTGGTGAATACAGTCATGTAGTTGCCTTTAATACTTTACTATTCCTTATGTCAT<br>TCACTGTACTCTGTTTAACACCAGTTTACTCATTCTTACCTGGTGTTTATTCTGTTATTT<br>ACTTGTACTTGACATTTTATCTTACTAATGATGTTTCTTTTTTAGCACATATTCAGTGGA<br>TGGTTATGTTCACACCTTTAGTACCTTTCTGGATAACAATTGCTTATATCATTTGTATTT<br>CCACAAAGCATTTCTATTGGTTCTTTAGTAATTACCTAAAGAGACGTGTAGTCTTTAATG<br>GTGTTTCCTTTAGTACTTTTGAAGAAGCTGCGCTGTGCACCTTTTTGTTAAATAAAGAAA<br>TGTATCTAAAGTTGCGTAGTGATGTGCTATTACCTCTTACGCAATATAATAGATACTTAG<br>CTCTTTATAATAAGTACAAGTATTTTAGTGGAGCAATGGATACAACTAGCTACAGAGAAG<br>CTGCTTGTTGTCATCTCGCAAAGGCTCTCAATGACTTCAGTAACTCAGGTTCTGATGTTC<br>TTTACCAACCACCACAAACCTCTATCACCTCAGCTGTTTTGCAGAGTGGTTTTAGAAAAA<br>TGGCATTCCCATCTGGTAAAGTTGAGGGTTGTATGGTACAAGTAACTTGTGGTACAACTA<br>CACTTAACGGTCTTTGGCTTGATGACGTAGTTTACTGTCCAAGACATGTGATCTGCACCT<br>CTGAAGACATGCTTAACCCTAATTATGAAGATTTACTCATTCGTAAGTCTAATCATAATT<br>TCTTGGTACAGGCTGGTAATGTTCAACTCAGGGTTATTGGACATTCTATGCAAAATTGTG<br>TACTTAAGCTTAAGGTTGATACAGCCAATCCTAAGACACCTAAGTATAAGTTTGTTCGCA<br>TTCAACCAGGACAGACTTTTTCAGTGTTAGCTTGTTACAATGGTTCACCATCTGGTGTTT<br>ACCAATGTGCTATGAGGCCCAATTTCACTATTAAGGGTTCATTCCTTAATGGTTCATGTG<br>GTAGTGTTGGTTTTAACATAGATTATGACTGTGTCTCTTTTTGTTACATGCACCATATGG<br>AATTACCAACTGGAGTTCATGCTGGCACAGACTTAGAAGGTAACTTTTATGGACCTTTTG<br>TTGACAGGCAAACAGCACAAGCAGCTGGTACGGACACAACTATTACAGTTAATGTTTTAG<br>CTTGGTTGTACGCTGCTGTTATAAATGGAGACAGGTGGTTTCTCAATCGATTTACCACAA<br>CTCTTAATGACTTTAACCTTGTGGCTATGAAGTACAATTATGAACCTCTAACACAAGACC<br>ATGTTGACATACTAGGACCTCTTTCTGCTCAAACTGGAATTGCCGTTTTAGATATGTGTG<br>CTTCATTAAAAGAATTACTGCAAAATGGTATGAATGGACGTACCATATTGGGTAGTGCTT<br>TATTAGAAGATGAATTTACACCTTTTGATGTTGTTAGACAATGCTCAGGTGTTACTTTCC<br>AAAGTGCAGTGAAAAGAACAATCAAGGGTACACACCACTGGTTGTTACTCACAATTTTGA |

TABLE 3-continued

SARS-CoV-2 genome fragments.

| SEQ ID NO | Nucleotide Sequence |
|---|---|
| | CTTCACTTTTAGTTTTAGTCCAGAGTACTCAATGGTCTTTGTTCTTTTTTTTGTATGAAA<br>ATGCCTTTTTACCTTTTGCTATGGGTATTATTGCTATGTCTGCTTTTGCAATGATGTTTG<br>TCAAACATAAGCATGCATTTCTCTGTTTGTTTTTGTTACCTTCTCTTGCCACTGT |
| SEQ ID NO: 22 | ACTAGGACCTCTTTCTGCTCAAACTGGAATTGCCGTTTTAGATATGTGTG<br>CTTCATTAAAAGAATTACTGCAAAATGGTATGAATGGACGTACCATATTGGGTAGTGCTT<br>TATTAGAAGATGAATTTACACCTTTTGATGTTGTTAGACAATGCTCAGGTGTTACTTTCC<br>AAAGTGCAGTGAAAAGAACAATCAAGGGTACACACCACTGGTTGTTACTCACAATTTTGA<br>CTTCACTTTTAGTTTTAGTCCAGAGTACTCAATGGTCTTTGTTCTTTTTTTTGTATGAAA<br>ATGCCTTTTTACCTTTTGCTATGGGTATTATTGCTATGTCTGCTTTTGCAATGATGTTTG<br>TCAAACATAAGCATGCATTTCTCTGTTTGTTTTTGTTACCTTCTCTTGCCACTGTAGCTT<br>ATTTTAATATGGTCTATATGCCTGCTAGTTGGGTGATGCGTATTATGACATGGTTGGATA<br>TGGTTGATACTAGTTTGTCTGGTTTTAAGCTAAAAGACTGTGTTATGTATGCATCAGCTG<br>TAGTGTTACTAATCCTTATGACAGCAAGAACTGTGTATGATGATGGTGCTAGGAGAGTGT<br>GGACACTTATGAATGTCTTGACACTCGTTTATAAAGTTTATTATGGTAATGCTTTAGATC<br>AAGCCATTTCCATGTGGGCTCTTATAATCTCTGTTACTTCTAACTACTCAGGTGTAGTTA<br>CAACTGTCATGTTTTTGGCCAGAGGTATTGTTTTTATGTGTGTTGAGTATTGCCCTATTT<br>TCTTCATAACTGGTAATACACTTCAGTGTATAATGCTAGTTTATTGTTTCTTAGGCTATT<br>TTTGTACTTGTTACTTTGGCCTCTTTTGTTTACTCAACCGCTACTTTAGACTGACTCTTG<br>GTGTTTATGATTACTTAGTTTCTACACAGGAGTTTAGATATATGAATTCACAGGGACTAC<br>TCCCACCCAAGAATAGCATAGATGCCTTCAAACTCAACATTAAATTGTTGGGTGTTGGTG<br>GCAAACCTTGTATCAAAGTAGCCACTGTACAGTCTAAAATGTCAGATGTAAAGTGCACAT<br>CAGTAGTCTTACTCTCAGTTTTGCAACAACTCAGAGTAGAATCATCATCTAAATTGTGGG<br>CTCAATGTGTCCAGTTACACAATGACATTCTCTTAGCTAAAGATACTACTGAAGCCTTTG<br>AAAAAATGGTTTCACTACTTTCTGTTTTGCTTTCCATGCAGGGTGCTGTAGACATAAACA<br>AGCTTTGTGAAGAAATGCTGGACAACAGGGCAACCTTACAAGCTATAGCCTCAGAGTTTA<br>GTTCCCTTCCATCATATGCAGCTTTTGCTACTGCTCAAGAAGCTTATGAGCAGGCTGTTG<br>CTAATGGTGATTCTGAAGTTGTTCTTAAAAAGTTGAAGAAGTCTTTGAATGTGGCTAAAT<br>CTGAATTTGACCGTGATGCAGCCATGCAACGTAAGTTGGAAAAGATGGCTGATCAAGCTA<br>TGACCCAAATGTATAAACAGGCTAGATCTGAGGACAAGAGGGCAAAAGTTACTAGTGCTA<br>TGCAGACAATGCTTTTCACTATGCTTAGAAAGTTGGATAATGATGCACTCAACAACATTA<br>TCAACAATGCAAGAGATGGTTGTGTTCCCTTGAACATAATACCTCTTACAACAGCAGCCA<br>AACTAATGGTTGTCATACCAGACTATAACACATATAAAAATACGTGTGATGGTACAACAT<br>TTACTTATGCATCAGCATTGTGGGAAATCCAACAGGTTGTAGATGCAGATAGTAAAATTG<br>TTCAACTTAGTGAAATTAGTATGGACAATTCACCTAATTTAGCATGGCCTCTTATTGTAA<br>CAGCTTTAAGGGCCAATTCTGCTGTCAAATTACAGAATAATGAGCTTAGTCCTGTTGCAC<br>TACGACAGATGTCTTGTGCTGCCGGTACTACACAAACTGCTTGCACTGATGACAATGCGT<br>TAGCTTACTACAACACAACAAAGGGAGGTAGGTTTGTACTTGCACTGTTATCCGATTTAC<br>AGGATTTGAAATGGGCTAGATTCCCTAAGAGTGATGGAACTGGTACTATCTATACAGAAC<br>TGGAACCACCTTGTAGGTTTGTTACAGACACACCTAAAGGTCCTAAAGTGAAGTATTTAT<br>ACTTTATTAAAGGATTAAACAACCTAAATAGAGGTATGGTACTTGGTAGTTTAGCTGCCA<br>CAGTACGTCTACAAGCTGGTAATGCAACAGAAGTGCCTGCCAATTCAACTGTATTATCTT<br>TCTGTGCTTTTGCTGTAGATGCTGCTAAAGCTTACAAAGATTATCTAGCTAGTGGGGGAC<br>AACCAATCACTAATTGTGTTAAGATGTTGTGTACACACACTGGTACTGGTCAGGCAATAA<br>CAGTTACACCGGAAGCCAATATGGATCAAGAATCCTTTGGTGGTGCATCGTGTTGTCTGT<br>ACTGCCGTTGCCACATAGATCATCCAAATCCTAAAGGATTTTGTGACTTAAAAGGTAAGT<br>ATGTACAAATACCTACAACTTGTGCTAATGACCCTGTGGGTTTTACACTTAAAAACACAG<br>TCTGTACCGTCTGCGGTATGTGGAAAGGTTATGGCTGTAGTTGTGATCAACTCCGCGAAC<br>CCATGCTTCAGTCAGCTGATGCACAATCGTTTTTAAACGGGTTTGCGGTGTAAGTGCAGC<br>CCGTCTTACACCGTGCGGCACAGGCACTAGTACTGATGTCGTATACAGGGCTTTTGACAT<br>CTACAATGATAAAGTAGCTGGTTTTGCTAAATTCCTAAAAACTAATTGTTGTCGCTTCCA<br>AGAAAAGGACGAAGATGACAATTTAATTGATTCTTACTTTGTAGTTAAGAGACACACTTT<br>CTCTAACTACCAACATGAAGAAACAATTTATAATTTACTTAAGGATTGTCCAGCTGTTGC<br>TAAACATGACTTCTTTAAGTTTAGAATAGACGGTGACATGGTACCACATATATCACGTCA<br>ACGTCTTACTAAATACACAATGGCAGACCTCGTCTATGCTTTAAGGCATTTTGATGAAGG<br>TAATTGTGACACATTAAAAGAAATACTTGTCACATACAATTGTTGTGATGA |
| SEQ ID NO: 23 | CCGTGCGGCACAGGCACTAGTACTGATGTCGTATACAGGGCTTTTGACAT<br>CTACAATGATAAAGTAGCTGGTTTTGCTAAATTCCTAAAAACTAATTGTTGTCGCTTCCA<br>AGAAAAGGACGAAGATGACAATTTAATTGATTCTTACTTTGTAGTTAAGAGACACACTTT<br>CTCTAACTACCAACATGAAGAAACAATTTATAATTTACTTAAGGATTGTCCAGCTGTTGC<br>TAAACATGACTTCTTTAAGTTTAGAATAGACGGTGACATGGTACCACATATATCACGTCA<br>ACGTCTTACTAAATACACAATGGCAGACCTCGTCTATGCTTTAAGGCATTTTGATGAAGG<br>TAATTGTGACACATTAAAAGAAATACTTGTCACATACAATTGTTGTGATGATGATTATTT<br>CAATAAAAAGGACTGGTATGATTTTGTAGAAAACCCAGATATATTACGCGTATACGCCAA<br>CTTAGGTGAACGTGTACGCCAAGCTTTGTTAAAAACAGTACAATTCTGTGATGCCATGCG<br>AAATGCTGGTATTGTTGGTGTACTGACATTAGATAATCAAGATCTCAATGGTAACTGGTA<br>TGATTTCGGTGATTTCATACAAACCACGCCAGGTAGTGGAGTTCCTGTTGTAGATTCTTA<br>TTATTCATTGTTAATGCCTATATTAACCTTGACCAGGGCTTTAACTGCAGAGTCACATGT<br>TGACACTGACTTAACAAAGCCTTACATTAAGTGGGATTTGTTAAAATATGACTTCACGGA<br>AGAGAGGTTAAAACTCTTTGACCGTTATTTTAAATATTGGGATCAGACATACCACCCAAA<br>TTGTGTTAACTGTTTGGATGACAGATGCATTCTGCATTGTGCAAACTTTAATGTTTTATT<br>CTCTACAGTGTTCCCACCTACAAGTTTTGGACCACTAGTGAGAAAAATATTTGTTGATGG<br>TGTTCCATTTGTAGTTTCAACTGGATACCACTTCAGAGAGCTAGGTGTTGTACATAATCA<br>GGATGTAAACTTACATAGCTCTAGACTTAGTTTTAAGGAATTACTTGTGTATGCTGCTGA |

TABLE 3-continued

SARS-CoV-2 genome fragments.

| SEQ ID NO | Nucleotide Sequence |
|---|---|
| | CCCTGCTATGCACGCTGCTTCTGGTAATCTATTACTAGATAAACGCACTACGTGCTTTTC<br>AGTAGCTGCACTTACTAACAATGTTGCTTTTCAAACTGTCAAACCCGGTAATTTTAACAA<br>AGACTTCTATGACTTTGCTGTGTCTAAGGGTTTCTTTAAGGAAGGAAGTTCTGTTGAATT<br>AAAACACTTCTTCTTTGCTCAGGATGGTAATGCTGCTATCAGCGATTATGACTACTATCG<br>TTATAATCTACCAACAATGTGTGATATCAGACAACTACTATTTGTAGTTGAAGTTGTTGA<br>TAAGTACTTTGATTGTTACGATGGTGGCTGTATTAATGCTAACCAAGTCATCGTCAACAA<br>CCTAGACAAATCAGCTGGTTTTCCATTTAATAAATGGGGTAAGGCTAGACTTTATTATGA<br>TTCAATGAGTTATGAGGATCAAGATGCACTTTTCGCATATACAAAACGTAATGTCATCCC<br>TACTATAACTCAAATGAATCTTAAGTATGCCATTAGTGCAAAGAATAGAGCTCGCACCGT<br>AGCTGGTGTCTCTATCTGTAGTACTATGACCAATAGACAGTTTCATCAAAAATTATTGAA<br>ATCAATAGCCGCCACTAGAGGAGCTACTGTAGTAATTGGAACAAGCAAATTCTATGGTGG<br>TTGGCACAACATGTTAAAAACTGTTTATAGTGATGTAGAAAACCCTCACCTTATGGGTTG<br>GGATTATCCTAAATGTGATAGAGCCATGCCTAACATGCTTAGAATTATGGCCTCACTTGT<br>TCTTGCTCGCAAACATACAACGTGTTGTAGCTTGTCACACCGTTTCTATAGATTAGCTAA<br>TGAGTGTGCTCAAGTATTGAGTGAAATGGTCATGTGTGGCGGTTCACTATATGTTAAACC<br>AGGTGGAACCTCATCAGGAGATGCCACAACTGCTTATGCTAATAGTGTTTTTAACATTTG<br>TCAAGCTGTCACGGCCAATGTTAATGCACTTTTATCTACTGATGGTAACAAAATTGCCGA<br>TAAGTATGTCCGCAATTTACAACACAGACTTTATGAGTGTCTCTATAGAAATAGAGATGT<br>TGACACAGACTTTGTGAATGAGTTTTACGCATATTTGCGTAAACATTTCTCAATGATGAT<br>ACTCTCTGACGATGCTGTTTGTGTGTTTCAATAGCACTTATGCATCTCAAGGTCTAGTGGC<br>TAGCATAAAGAACTTTAAGTCAGTTCTTTATTATCAAAACAATGTTTTTATGTCTGAAGC<br>AAAATGTTGGACTGAGACTGACCTTACTAAAGGACCTCATGAATTTTGCTCTCAACATAC<br>AATGCTAGTTAAACAGGGTGATGATTATGTGTACCTTCCTTACCCAGATCCATCAAGAAT<br>CCTAGGGGCCGGCTGTTTTGTAGATGATATCGTAAAAACAGATGGTACACTTATGATTGA<br>ACGGTTCGTGTCTTTAGCTATAGATGCTTACCCACTTACTAAACATCCTAATCAGGAGTA<br>TGCTGATGTCTTTCATTTGTACTTACAATACATAAGAAAGCTACATGATGAGTTAACAGG<br>ACACATGTTAGACATGTATTCTGTTATGCTTACTAATGATAACACTTCAAGGTATTGGGA<br>ACCTGAGTTTTATGAGGCTATGTACACACCGCATACAGTCTTACAGGCTGTTGGGGCTTG<br>TGTTCTTTGCAATTCACAGACTTCATTAAGATGTGGTGCTTGCATACGTAGACCATTCTT<br>ATGTTGTAAATGCTGTTACGACCATGTCATATCAACATCACATAAATTAGTCTTGTCTGT<br>TAATCCGTATGTTTGCAATGCTCCAGGTTGTGATGTCACAGATGTGACTC |
| SEQ ID NO: 24 | TATGAGGCTATGTACACACCGCATACAGTCTTACAGGCTGTTGGGGCTTG<br>TGTTCTTTGCAATTCACAGACTTCATTAAGATGTGGTGCTTGCATACGTAGACCATTCTT<br>ATGTTGTAAATGCTGTTACGACCATGTCATATCAACATCACATAAATTAGTCTTGTCTGT<br>TAATCCGTATGTTTGCAATGCTCCAGGTTGTGATGTCACAGATGTGACTCAACTTTACTT<br>AGGAGGTATGAGCTATTATTGTAAATCACATAAACCCACCCATTAGTTTTCCATTGTGTGC<br>TAATGGACAAGTTTTTGGTTTATATAAAAATACATGTGTTGGTAGCGATAATGTTACTGA<br>CTTTAATGCAATTGCAACATGTGACTGGACAAATGCTGGTGATTACATTTTAGCTAACAC<br>CTGTACTGAAAGACTCAAGCTTTTTGCAGCAGAAACGCTCAAAGCTACTGAGGAGACATT<br>TAAACTGTCTTATGGTATTGCTACTGTACGTGAAGTGCTGTCTGACAGAGAATTACATCT<br>TTCATGGGAAGTTGGTAAACCTAGACCACCACTTAACCGAAATTATGTCTTTACTGGTTA<br>TCGTGTAACTAAAAACAGTAAAGTACAAATAGGAGAGTACACCTTTGAAAAAGGTGACTA<br>TGGTGATGCTGTTGTTTACCGAGGTACAACAACTTACAAATTAAATGTTGGTGATTATTT<br>TGTGCTGACATCACATACAGTAATGCCATTAAGTGCACCTACACTAGTGCCACAAGAGCA<br>CTATGTTAGAATTACTGGCTTATACCCAACACTCAATATCTCAGATGAGTTTTCTAGCAA<br>TGTTGCAAATTATCAAAAGGTTGGTATGCAAAGTATTCTACACTCCAGGGACCACCTGG<br>TACTGGTAAGAGTCATTTTGCTATTGGCCTAGCTCTCTACTACCCTTCTGCTCGCATAGT<br>GTATACAGCTTGCTCTCATGCCGCTGTTGATGCACTATGTGAGAAGGCATTAAAATATTT<br>GCCTATAGATAAATGTAGTAGAATTATACCTGCACGTGCTCGTGTAGAGTGTTTTGATAA<br>ATTCAAAGTGAATTCAACATTAGAACAGTATGTCTTTTGTACTGTAAATGCATTGCCTGA<br>GACGACAGCAGATATAGTTGTCTTTGATGAAATTTCAATGGCCACAAATTATGATTTGAG<br>TGTTGTCAATGCCAGATTACGTGCTAAGCACTATGTGTACATTGGCGACCCTGCTCAATT<br>ACCTGCACCACGCACATTGCTAACTAAGGGCACACTAGAACCAGAATATTTCAATTCAGT<br>GTGTAGACTTATGAAAACTATAGGTCCAGACATGTTCCTCGGAACTTGTCGGCGTTGTCC<br>TGCTGAAATTGTTGACACTGTGAGTGCTTTGGTTTATGATAATAAGCTTAAAGCACATAA<br>AGACAAATCAGCTCAATGCTTTAAAATGTTTTATAAGGGTGTTATCACGCATGATGTTTC<br>ATCTGCAATTAACAGGCCACAAATAGGCGTGGTAAGAGAATTCCTTACACGTAACCCTGC<br>TTGGAGAAAAGCTGTCTTTATTTCACCTTATAATTCACAGAATGCTGTAGCCTCAAAGAT<br>TTTGGGACTACCAACTCAAACTGTTGATTCATCACAGGGCTCAGAATATGACTATGTCAT<br>ATTCACTCAAACCACTGAAACAGCTCACTCTTGTAATGTAAACAGATTTAATGTTGCTAT<br>TACCAGAGCAAAAGTAGGCATACTTTGCATAATGTCTGATAGAGACCTTTATGACAAGTT<br>GCAATTTACAAGTCTTGAAATTCCACGTAGGAATGTGGCAACTTTACAAGCTGAAAATGT<br>AACAGGACTCTTTAAAGATTGTAGTAAGGTAATCACTGGGTTACATCCTACACAGGCACC<br>TACACACCTCAGTGTTGACACTAAATTCAAAACTGAAGGTTTATGTGTTGACATACCTGG<br>CATACCTAAGGACATGACCTATAGAAGACTCATCTCTATGATGGGTTTTAAAATGAATTA<br>TCAAGTTAATGGTTACCCTAACATGTTTATCACCCGCGAAGAAGCTATAAGACATGTACG<br>TGCATGGATTGGCTTCGATGTCGAGGGGTGTCATGCTACTAGAGAAGCTGTTGGTACCAA<br>TTTACCTTTACAGCTAGGTTTTTCTACAGGTGTTAACCTAGTTGCTGTACCTACAGGTTA<br>TGTTGATACACCTAATAATACAGATTTTTCCAGAGTTAGTGCTAAACCACCTGGAGA<br>TCAATTTAAACACCTCATACCACTTATGTACAAAGGACTTCCTTGGAATGTAGTGCGTAT<br>AAAGATTGTACAAATGTTAAGTGACACACTTAAAATCTCTCTGACAGAGTCGTATTTGT<br>CTTATGGGCACATGGCTTTGAGTTGACATCTATGAAGTATTTTGTGAAAATAGGACCTGA<br>GCGCACCTGTTGTCTATGTGATAGACGTGCCACATGCTTTTCCACTGCTTCAGACACTTA<br>TGCCTGTTGGCATCATTCTATTGGATTTGATTACGTCTATAATCCGTTTATGATTGATGT |

TABLE 3-continued

SARS-CoV-2 genome fragments.

| SEQ ID NO | Nucleotide Sequence |
|---|---|
| | TCAACAATGGGGTTTTACAGGTAACCTACAAAGCAACCATGATCTGTATTGTCAAGTCCA<br>TGGTAATGCACATGTAGCTAGTTGTGATGCAATCATGACTAGGTGTCTAGCTGTCCACGA<br>GTGCTTTGTTAAGCGTGTTGACTGGACTATTGAATATCCTATAATTGGTGATGAACTGAA<br>GATTAATGCGGCTTGTAGAAAGGTTCAACACATGGTTGTTAAAGCTGCATTATTAGCAGA<br>CAAATTCCCAGTTCTTCACGACATTGGTAACCCTAAAGCTATTAAGTGTGTACCTCAAGC<br>TGATGTAGAATGGAAGTTCTATGATGCACAGCCTTGTAGTGACAAAGCTTATAAAATAGA<br>AGAATTATTCTATTCTTATGCCACACATTCTGACAAATTCACAGATGGTGTATGCCTATT<br>TTGGAATTGCAATGTCGATAGATATCCTGCTAATTCCATTGTTTGTAGATTTGACACTAG<br>AGTGCTATCTAACCTTAACTTGCCTGGTTGTGATGGTGGCAGTTTGTATG |
| SEQ ID NO: 25 | AAGCGTGTTGACTGGACTATTGAATATCCTATAATTGGTGATGAACTGAA<br>GATTAATGCGGCTTGTAGAAAGGTTCAACACATGGTTGTTAAAGCTGCATTATTAGCAGA<br>CAAATTCCCAGTTCTTCACGACATTGGTAACCCTAAAGCTATTAAGTGTGTACCTCAAGC<br>TGATGTAGAATGGAAGTTCTATGATGCACAGCCTTGTAGTGACAAAGCTTATAAAATAGA<br>AGAATTATTCTATTCTTATGCCACACATTCTGACAAATTCACAGATGGTGTATGCCTATT<br>TTGGAATTGCAATGTCGATAGATATCCTGCTAATTCCATTGTTTGTAGATTTGACACTAG<br>AGTGCTATCTAACCTTAACTTGCCTGGTTGTGATGGTGGCAGTTTGTATGTAAATAAACA<br>TGCATTCCACACACCAGCTTTTGATAAAAGTGCTTTTGTTAATTTAAAACAATTACCATT<br>TTTCTATTACTCTGACAGTCCATGTGAGTCTCATGGAAAACAAGTAGTGTCAGATATAGA<br>TTATGTACCACTAAAGTCTGCTACGTGTATAACACGTTGCAATTTAGGTGGTGCTGTCTG<br>TAGACATCATGCTAATGAGTACAGATTGTATCTCGATGCTTATAACATGATGATCTCAGC<br>TGGCTTTAGCTTGTGGGTTTACAAACAATTTGATACTTATAACCTCTGGAACACTTTTAC<br>AAGACTTCAGAGTTTAGAAAATGTGGCTTTTAATGTTGTAAATAAGGGACACTTTGATGG<br>ACAACAGGGTGAAGTACCAGTTTCTATCATTAATAACACTGTTTACACAAAAGTTGATGG<br>TGTTGATGTAGAATTGTTTGAAAATAAAACAACATTACCTGTTAATGTAGCATTTGAGCT<br>TTGGGCTAAGCGCAACATTAAACCAGTACCAGAGGTGAAAATACTCAATAATTTGGGTGT<br>GGACATTGCTGCTAATACTGTGATCTGGGACTACAAAAGAGATGCTCCAGCACATATATC<br>TACTATTGGTGTTTGTTCTATGACTGACATAGCCAAGAAACCAACTGAAACGATTTGTGC<br>ACCACTCACTGTCTTTTTTGATGGTAGAGTTGATGGTCAAGTAGACTTATTTAGAAATGC<br>CCGTAATGGTGTTCTTATTACAGAAGGTAGTGTTAAAGGTTTACAACCATCTGTAGGTCC<br>CAAACAAGCTAGTCTTAATGGAGTCACATTAATTGGAGAAGCCGTAAAAACACAGTTCAA<br>TTATTATAAGAAAGTTGATGGTGTTGTCCAACAATTACCTGAAACTTACTTTACTCAGAG<br>TAGAAATTTACAAGAATTTAAACCCAGGAGTCAAATGGAAATTGATTTCTTAGAATTAGC<br>TATGGATGAATTCATTGAACGGTATAAATTAGAAGGCTATGCCTTCGAACATATCGTTTA<br>TGGAGATTTTAGTCATAGTCAGTTAGGTGGTTTACATCTACTGATTGGACTAGCTAAACG<br>TTTTAAGGAATCACCTTTTGAATTAGAAGATTTTATTCCTATGGACAGTACAGTTAAAAA<br>CTATTTCATAACAGATGCGCAAACAGGTTCATCTAAGTGTGTGTGTTCTGTTATTGATTT<br>ATTACTTGATGATTTTGTTGAAATAATAAAATCCCAAGATTTATCTGTAGTTTCTAAGGT<br>TGTCAAAGTGACTATTGACTATACAGAAATTTCATTTATGCTTTGGTGTAAAGATGGCCA<br>TGTAGAAACATTTTACCCAAAATTACAATCTAGTCAAGCGTGGCAACCGGGTGTTGCTAT<br>GCCTAATCTTTACAAAATGCAAAGAATGCTATTAGAAAAGTGTGACCTTCAAAATTATGG<br>TGATAGTGCAACATTACCTAAAGGCATAATGATGAATGTCGCAAAATATACTCAACTGTG<br>TCAATATTTAAACACATTAACATTAGCTGTACCCTATAATATGAGAGTTATACATTTTGG<br>TGCTGGTTCTGATAAAGGAGTTGCACCAGGTACAGCTGTTTTAAGACAGTGGTTGCCTAC<br>GGGTACGCTGCTTGTCGATTCAGATCTTAATGACTTTGTCTCTGATGCAGATTCAACTTT<br>GATTGGTGATTGTGCAACTGTACATACAGCTAATAAATGGGATCTCATTATTAGTGATAT<br>GTACGACCCTAAGACTAAAAATGTTACAAAAGAAAATGACTCTAAAGAGGGTTTTTTCAC<br>TTACATTTGTGGGTTTATACAACAAAAGCTAGCTCTTGGAGGTTCCGTGGCTATAAAGAT<br>AACAGAACATTCTTGGAATGCTGATCTTTATAAGCTCATGGGACACTTCGCATGGTGGAC<br>AGCCTTTGTTACTAATGTGAATGCGTCATCATCTGAAGCATTTTTAATTGGATGTAATTA<br>TCTTGGCAAACCACGCGAACAAATAGATGGTTATGTCATGCATGCAAATTACATATTTTG<br>GAGGAATACAAATCCAATTCAGTTGTCTTCCTATTCTTTATTTGACATGAGTAAATTTCC<br>CCTTAAATTAAGGGGTACTGCTGTTATGTCTTTAAAAGAAGGTCAAATCAATGATATGAT<br>TTTATCTCTTCTTAGTAAAGGTAGACTTATAATTAGAGAAAACAACAGAGTTGTTATTTC<br>TAGTGATGTTCTTGTTAACAACTAAACGAACAATGTTTGTTTTTCTTGTTTTATTGCCAC<br>TAGTCTCTAGTCAGTGTGTTAATCTTACAACCAGAACTCAATTACCCCCTGCATACACTA<br>ATTCTTTCACACGTGGTGTTTATTACCCTGACAAAGTTTTCAGATCCTCAGTTTTACATT<br>CAACTCAGGACTTGTTCTTACCTTTCTTTTCCAATGTTACTTGGTTCCATGCTATACATG<br>TCTCTGGGACCAATGGTACTAAGAGGTTTGATAACCCTGTCCTACCATTTAATGATGGTG<br>TTTATTTTGCTTCCACTGAGAAGTCTAACATAATAAGAGGCTGGATTTTTGGTACTACTT<br>TAGATTCGAAGACCCAGTCCCTACTTATTGTTAATAACGCTACTAATGTTGTTATTAAAG<br>TCTGTGAATTTCAATTTTGTAATGATCCATTTTTGGGTGTTTATTACCACAAAAACAACA<br>AAAGTTGGATGGAAAGTGAGTTCAGAGTTTATTCTAG |
| SEQ ID NO: 26 | TCAGTGTGTTAATCTTACAACCAGAACTCAATTACCCCCTGCATACACTA<br>ATTCTTTCACACGTGGTGTTTATTACCCTGACAAAGTTTTCAGATCCTCAGTlliACATT<br>CAACTCAGGACTTGTTCTTACCTTTCTTTTCCAATGTTACTTGGTTCCATGCTATACATG<br>TCTCTGGGACCAATGGTACTAAGAGGTTTGATAACCCTGTCCTACCATTTAATGATGGTG<br>TTTATTTTGCTTCCACTGAGAAGTCTAACATAATAAGAGGCTGGATTTTTGGTACTACTT<br>TAGATTCGAAGACCCAGTCCCTACTTATTGTTAATAACGCTACTAATGTTGTTATTAAAG<br>TCTGTGAATTTCAATTTTGTAATGATCCATTTTTGGGTGTTTATTACCACAAAAACAACA<br>AAAGTTGGATGGAAAGTGAGTTCAGAGTTTATTCTAGTGCGAATAATTGCACTTTTGAAT<br>ATGTCTCTCAGCCTTTTCTTATGGACCTTGAAGGAAAACAGGGTAATTTCAAAAATCTTA<br>GGGAATTTGTGTTTAAGAATATTGATGGTTATTTTAAAATATATTCTAAGCACACGCCTA<br>TTAATTTAGTGCGTGATCTCCCTCAGGGTTTTTCGGCTTTAGAACCATTGGTAGATTTGC |

TABLE 3-continued

SARS-CoV-2 genome fragments.

| SEQ ID NO | Nucleotide Sequence |
|---|---|
| | CAATAGGTATTAACATCACTAGGTTTCAAACTTTACTTGCTTTACATAGAAGTTATTTGA<br>CTCCTGGTGATTCTTCTTCAGGTTGGACAGCTGGTGCTGCAGCTTATTATGTGGGTTATC<br>TTCAACCTAGGACTTTTCTATTAAAATATAATGAAAATGGAACCATTACAGATGCTGTAG<br>ACTGTGCACTTGACCCTCTCTCAGAAACAAAGTGTACGTTGAAATCCTTCACTGTAGAAA<br>AAGGAATCTATCAAACTTCTAACTTTAGAGTCCAACCAACAGAATCTATTGTTAGATTTC<br>CTAATATTACAAACTTGTGCCCTTTTGGTGAAGTTTTTAACGCCACCAGATTTGCATCTG<br>TTTATGCTTGGAACAGGAAGAGAATCAGCAACTGTGTTGCTGATTATTCTGTCCTATATA<br>ATTCCGCATCATTTTCCACTTTTAAGTGTTATGGAGTGTCTCCTACTAAATTAAATGATC<br>TCTGCTTTACTAATGTCTATGCAGATTCATTTGTAATTAGAGGTGATGAAGTCAGACAAA<br>TCGCTCCAGGGCAAACTGGAAGATTGCTGATTATAATTATAAATTACCAGATGATT1TA<br>CAGGCTGCGTTATAGCTTGGAATTCTAACAATCTTGATTCTAAGGTTGGTGGTAATTATA<br>ATTACCTGTATAGATTGTTTAGGAAGTCTAATCTCAAACCTTTTGAGAGAGATATTTCAA<br>CTGAAATCTATCAGGCCGGTAGCACACCTTGTAATGGTGTTGAAGGTTTTAATTGTTACT<br>TTCCTTTACAATCATATGGTTTCCAACCCACTAATGGTGTTGGTTACCAACCATACAGAG<br>TAGTAGTACTTTCTTTTGAACTTCTACATGCACCAGCAACTGTTTGTGGACCTAAAAAGT<br>CTACTAATTTGGTTAAAAACAAATGTGTCAATTTCAACTTCAATGGTTTAACAGGCACAG<br>GTGTTCTTACTGAGTCTAACAAAAAGTTTCTGCCTTTCCAACAATTTGGCAGAGACATTG<br>CTGACACTACTGATGCTGTCCGTGATCCACAGACACTTGAGATTCTTGACATTACACCAT<br>GTTCTTTTGGTGGTGTCAGTGTTATAACACCAGGAACAAATACTTCTAACCAGGTTGCTG<br>TTCTTTATCAGGATGTTAACTGCACAGAAGTCCCTGTTGCTATTCATGCAGATCAACTTA<br>CTCCTACTTGGCGTGTTTATTCTACAGGTTCTAATGTTTTTCAAACACGTGCAGGCTGTT<br>TAATAGGGGCTGAACATGTCAACAACTCATATGAGTGTGACATACCCATTGGTGCAGGTA<br>TATGCGCTAGTTATCAGACTCAGACTAATTCTCCTCGGCGGGCACGTAGTGTAGCTAGTC<br>AATCCATCATTGCCTACACTATGTCACTTGGTGCAGAAAATTCAGTTGCTTACTCTAATA<br>ACTCTATTGCCATACCCACAAATTTTACTATTAGTGTTACCACAGAAATTCTACCAGTGT<br>CTATGACCAAGACATCAGTAGATTGTACAATGTACATTTGTGGTGATTCAACTGAATGCA<br>GCAATCTTTGTTGGAATATGGGAGTTTTTGTACACAATTAAACCGTGCTTTAACTGGAA<br>TAGCTGTTGAACAAGACAAAAACACCCAAGAAGTTTTTGCACAAGTCAAACAAATTTACA<br>AAACACCACCAATTAAAGATTTTGGTGGTTTTAATTTTTCACAAATATTACCAGATCCAT<br>CAAAACCAAGCAAGAGGTCATTTATTGAAGATCTACTTTTCAACAAAGTGACACTTGCAG<br>ATGCTGGCTTCATCAAACAATATGGTGATTGCCTTGGTGATATTGCTGCTAGAGACCTCA<br>TTTGTGCACAAAAGTTTAACGGCCTTACTGTTTTGCCACCTTTGCTCACAGATGAAATGA<br>TTGCTCAATACACTTCTGCACTGTTAGCGGGTACAATCACTTCTGGTTGGACCTTTGGTG<br>CAGGTGCTGCATTACAAATACCATTTGCTATGCAAATGGCTTATAGGTTTAATGGTATTG<br>GAGTTACACAGAATGTTCTCTATGAGAACCAAAAATTGATTGCCAACCAATTTAATAGTG<br>CTATTGGCAAAATTCAAGACTCACTTTCTTCCACAGCAAGTGCACTTGGAAAACTTCAAG<br>ATGTGGTCAACCAAAATGCACAAGCTTTAAACACGCTTGTTAAACAACTTAGCTCCAATT<br>TTGGTGCAATTTCAAGTGTTTTAAATGATATCCTTTCACGTCTTGACAAAGTTGAGGCTG<br>AAGTGCAAATTGATAGGTTGATCACAGGCAGACTTCAAAGTTTGCAGACATATGTGACTC<br>AACAATTAATTAGAGCTGCAGAAATCAGAGCTTCTGCTAATCTTGCTGCTACTAAAATGT<br>CAGAGTGTGTACTTGGACAATCAAAAGAGTTGATTTTTGTGGAAAGGGCTATCATCTTA<br>TGTCCTT |
| SEQ ID NO: 27 | GAATGTTCTCTATGAGAACCAAAAATTGATTGCCAACCAATTTAATAGTG<br>CTATTGGCAAAATTCAAGACTCACTTTCTTCCACAGCAAGTGCACTTGGAAAACTTCAAG<br>ATGTGGTCAACCAAAATGCACAAGCTTTAAACACGCTTGTTAAACAACTTAGCTCCAATT<br>TTGGTGCAATTTCAAGTGTTTTAAATGATATCCTTTCACGTCTTGACAAAGTTGAGGCTG<br>AAGTGCAAATTGATAGGTTGATCACAGGCAGACTTCAAAGTTTGCAGACATATGTGACTC<br>AACAATTAATTAGAGCTGCAGAAATCAGAGCTTCTGCTAATCTTGCTGCTACTAAAATGT<br>CAGAGTGTGTACTTGGACAATCAAAAGAGTTGATTTTTGTGGAAAGGGCTATCATCTTA<br>TGTCCTTCCCTCAGTCAGCACCTCATGGTGTAGTCTTCTTGCATGTGACTTATGTCCCTG<br>CACAAGAAAGAACTTCACAACTGCTCCTGCCATTTGTCATGATGGAAAAGCACACTTTC<br>CTCGTGAAGGTGTCTTTGTTTCAAATGGCACACACTGGTTTGTAACACAAAGGAATTTTT<br>ATGAACCACAAATCATTACTACAGACAACACATTTGTGTCTGGTAACTGTGATGTTGTAA<br>TAGGAATTGTCAACAACACAGTTTATGATCCTTTGCAACCTGAATTAGACTCATTCAAGG<br>AGGAGTTAGATAAATATTTTAAGAATCATACATCACCAGATGTTGATTTAGGTGACATCT<br>CTGGCATTAATGCTTCAGTTGTAAACATTCAAAAAGAAATTGACCGCCTCAATGAGGTTG<br>CCAAGAATTTAAATGAATCTCTCATCGATCTCCAAGAACTTGGAAAGTATGAGCAGTATA<br>TAAAATGGCCATGGTACATTTGGCTAGGTTTTATAGCTGGCTTGATTGCCATAGTAATGG<br>TGACAATTATGCTTTGCTATGACCAGTTGCTGTAGTTGTCTCAAGGGCTGTTGTTCTT<br>GTGGATCCTGCTGCAAATTTGATGAAGACGACTCTGAGCCAGTGCTCAAAGGAGTCAAAT<br>TACATTACACATAAACGAACTTATGGATTTGTTTATGAGAATCTTCACAATTGGAACTTC<br>AACTTTGAAGCAAGGTGAAATCAAGGATGCTACTCCTTCAGATTTTGTTCGCGCTACTGC<br>AACGATACCGATACAAGCCTCACTCCCTTTCGGATGGCTTATTGTTGGCGTTGCACTTCT<br>TGCTGTTTTTCAGAGCGCTTCCAAAATCATAACCCTCAAAAAGAGATGGCAACTAGCACT<br>CTCCAAGGGTGTTCACTTTGTTTGCAACTTGCTGTTGTTGTTTGTAACAGTTTACTCACA<br>CCTTTTGCTCGTTGCTGCTGGCCTTGAAGCCCCTTTTCTCTATCTTTATGCTTTAGTCTA<br>CTTCTTGCAGAGTATAAACTTTGTAAGAATAATAATGAGGCTTTGGCTTTGCTGGAAATG<br>CCGTTCCAAAAACCCATTACTTTATGATGCCAACTATTTTCTTTGCTGGCATACTAATTG<br>TTACGACTATTGTATACCTTACAATAGTGTAACTTCTTCAATTGTCATTACTTCAGGTGA<br>TGGCACAACAAGTCCTATTTCTGAACATGACTACCAGATTGGTGGTTATACTGAAAAATG<br>GGAATCGGAGTAAAGACTGTGTTGTATTACACAGTTACTTCACTTCAGACTATTACCA<br>GCTGTACTCAACTCAATTGAGTACAGACACTGGTGTTGAACATGTTACCTTCTTCATCTA<br>CAATAAAATTGTTGATGAGCCTGAAGAACATGTCCAAATTCACACAATCGACGGTTCATC<br>CGGAGTTGTTAATCCAGTAATGGAACCAATTTATGATGAACCGACGACGACTACTAGCGT |

TABLE 3-continued

SARS-CoV-2 genome fragments.

| SEQ ID NO | Nucleotide Sequence |
|---|---|
| | GCCTTTGTAAGCACAAGCTGATGAGTACGAACTTATGTACTCATTCGTTTCGGAAGAGAC<br>AGGTACGTTAATAGTTAATAGCGTACTTCTTTTTCTTGCTTTCGTGGTATTCTTGCTAGT<br>TACACTAGCCATCCTTACTGCGCTTCGATTGTGTGCGTACTGCTGCAATATTGTTAACGT<br>GAGTCTTGTAAAACCTTCTTTTTACGTTTACTCTCGTGTTAAAAATCTGAATTCTTCTAG<br>AGTTCCTGATCTTCTGGTCTAAACGAACTAAATATTATATTAGTTTTTCTGTTTGGAACT<br>TTAATTTTAGCCATGGCAGATTCCAACGGTACTATTACCGTTGAAGAGCTTAAAAAGCTC<br>CTTGAACAATGGAACCTAGTAATAGGTTTCCTATTCCTTACATGGATTTGTCTTCTACAA<br>TTTGCCTATGCCAACAGGAATAGGTTTTTGTATATAATTAAGTTAATTTTCCTCTGGCTG<br>TTATGGCCAGTAACTTTAGCTTGTTTTGTGCTTGCTGCTGTTTACAGAATAAATTGGATC<br>ACCGGTGGAATTGCTATCGCAATGGCTTGTCTTGTAGGCTTGATGTGGCTCAGCTACTTC<br>ATTGCTTCTTTCAGACTGTTTGCGCGTACGCGTTCCATGTGGTCATTCAATCCAGAAACT<br>AACATTCTTCTCAACGTGCCACTCCATGGCACTATTCTGACCAGACCGCTTCTAGAAAGT<br>GAACTCGTAATCGGAGCTGTGATCCTTCGTGGACATCTTCGTATTGCTGGACACCATCTA<br>GGACGCTGTGACATCAAGGACCTGCCTAAAGAAATCACTGTTGCTACATCACGAACGCTT<br>TCTTATTACAAATTGGGAGCTTCGCAGCGTGTAGCAGGTGACTCAGGTTTTGCTGCATAC<br>AGTCGCTACAGGATTGGCAACTATAAATTAAACACAGACCATTCCAGTAGCAG |
| SEQ ID NO: 28 | TCCTCTGGCTGTTATGGCCAGTAACTTTAGCTTGTTTTGTGCTTGCTGCT<br>GTTTACAGAATAAATTGGATCACCGGTGGAATTGCTATCGCAATGGCTTGTCTTGTAGGC<br>TTGATGTGGCTCAGCTACTTCATTGCTTCTTTCAGACTGTTTGCGCGTACGCGTTCCATG<br>TGGTCATTCAATCCAGAAACTAACATTCTTCTCAACGTGCCACTCCATGGCACTATTCTG<br>ACCAGACCGCTTCTAGAAAGTGAACTCGTAATCGGAGCTGTGATCCTTCGTGGACATCTT<br>CGTATTGCTGGACACCATCTAGGACGCTGTGACATCAAGGACCTGCCTAAAGAAATCACT<br>GTTGCTACATCACGAACGCTTTCTTATTACAAATTGGGAGCTTCGCAGCGTGTAGCAGGT<br>GACTCAGGTTTTGCTGCATACAGTCGCTACAGGATTGGCAACTATAAATTAAACACAGAC<br>CATTCCAGTAGCAGTGACAATATTGCTTTGCTTGTACAGTAAGTGACAACAGATGTTTCA<br>TCTCGTTGACTTTCAGGTTACTATAGCAGAGATATTACTAATTATTATGAGGACTTTTAA<br>AGTTTCCATTTGGAATCTTGATTACATCATAAACCTCATAATTAAAAATTTATCTAAGTC<br>ACTAACTGAGAATAAATATTCTCAATTAGATGAAGAGCAACCAATGGAGATTGATTAAAC<br>GAACATGAAAATTATTCTTTTCTTGGCACTGATAACACTCGCTACTTGTGAGCTTTATCA<br>CTACCAAGAGTGTGTTAGAGGTACAACAGTACTTTTAAAAGAACCTTGCTCTTCTGGAAC<br>ATACGAGGGCAATTCACCATTTCATCCTCTAGCTGATAACAAATTTGCACTGACTTGCTT<br>TAGCACTCAATTTGCTTTTGCTTGTCCTGACGGCGTAAAACACGTCTATCAGTTACGTGC<br>CAGATCAGTTTCACCTAAACTGTTCATCAGACAAGAGGAAGTTCAAGAACTTTACTCTCC<br>AATTTTTCTTATTGTTGCGGCAATAGTGTTTATAACACTTTGCTTCACACTCAAAAGAAA<br>GACAGAATGATTGAACTTTCATTAATTGACTTCTATTTGTGCTTTTTAGCCTTTCTGCTA<br>TTCCTTGTTTTAATTATGCTTATTATCTTTTGGTTCTCACTTGAACTGCAAGATCATAAT<br>GAAACTTGTCACGCCTAAACGAACATGAAATTTCTTGTTTTCTTAGGAATCATCACAACT<br>GTAGCTGCATTTCACCAAGAATGTAGTTTACAGTCATGTACTCAACATCAACCATATGTA<br>GTTGATGACCCGTGTCCTATTCACTTCTATTCTAAATGGTATATTAGAGTAGGAGCTAGA<br>AAATCAGCACCTTTAATTGAATTGTGCGTGGATGAGGCTGGTTCTAAATCACCCATTCAG<br>TACATCGATATCGGTAATTATACAGTTTCCTGTTTACCTTTTACAATTAATTGCCAGGAA<br>CCTAAATTGGGTAGTCTTGTAGTGCGTTGTTCGTTCTATGAAGACTTTTTAGAGTATCAT<br>GACGTTCGTGTTGTTTTAGATTTCATCTAAACGAACAAACTAAAATGTCTGATAATGGAC<br>CCCAAAATCAGCGAAATGCACCCCGCATTACGTTTGGTGGACCCTCAGATTCAACTGGCA<br>GTAACCAGAATGGAGAACGCAGTGGGGCGCGATCAAAACAACGTCGGCCCCAAGGTTTAC<br>CCAATAATACTGCGTCTTGGTTCACCGCTCTCACTCAACATGGCAAGGAAGACCTTAAAT<br>TCCCTCGAGGACAAGGCGTTCCAATTAACACCAATAGCAGTCCAGATGACCAAATTGGCT<br>ACTACCGAAGAGCTACCAGACGAATTCGTGGTGGTGACGGTAAAATGAAAGATCTCAGTC<br>CAAGATGGTATTTCTACTACCTAGGAACTGGGCCAGAAGCTGGACTTCCCTATGGTGCTA<br>ACAAAGACGGCATCATATGGGTTGCAACTGAGGGAGCCTTGAATACACCAAAAGATCACA<br>TTGGCACCCGCAATCCTGCTAACAATGCTGCAATCGTGCTACAACTTCCTCAAGGAACAA<br>CATTGCCAAAAGGCTTCTACGCAGAAGGGAGCAGAGGCGGCAGTCAAGCCTCTTCTCGTT<br>CCTCATCACGTAGTCGCAACAGTTCAAGAAATTCAACTCCAGGCAGCAGTAGGGGAACTT<br>CTCCTGCTAGAATGGCTGGCAATGGCGGTGATGCTGCTCTTGCTTTGCTGCTGCTTGACA<br>GATTGAACCAGCTTGAGAGCAAAATGTCTGGTAAAGGCCAACAACAACAAGGCCAAACTG<br>TCACTAAGAAATCTGCTGCTGAGGCTTCTAAGAAGCCTCGGCAAAAACGTACTGCCACTA<br>AAGCATACAATGTAACACAAGCTTTCGGCAGACGTGGTCCAGAACAAACCCAAGGAAATT<br>TTGGGGACCAGGAACTAATCAGACAAGGAACTGATTACAAACATTGGCCGCAAATTGCAC<br>AATTTGCCCCCAGCGCTTCAGCGTTCTTCGGAATGTCGCGCATTGGCATGGAAGTCACAC<br>CTTCGGGAACGTGGTTGACCTACACAGGTGCCATCAAATTGGATGACAAAGATCCAAATT<br>TCAAAGATCAAGTCATTTTGCTGAATAAGCATATTGACGCATACAAAACATTCCCACCAA<br>CAGAGCCTAAAAAGGACAAAAAGAAGAAGGCTGATGAAACTCAAGCCTTACCGCAGAGAC<br>AGAAGAAACAGCAAACTGTGACTCTTCTTCCTGCTGCAGATTTGGATGATTTCTCCAAAC<br>AATTGCAACAATCCATGAGCAGTGCTGACTCAACTCAGGCCTAAACTCATGCAGACCACA<br>CAAGGCAGATGGGCTATATAAACGTTTTCGCTTTTCCGTTTACGATATATAGTCTACTCT<br>TGTGCAGAATGAATTCTCGTAACTACATAGCACAAGTAGATGTAGTTAACTTTAATCTCA<br>CATAGCAATCTTTAATCAGTGTGTAACATTAGGGAGGACTTGAAAGAGCCACCACATTTT<br>CACCGAGGCCACGCGGAGTACGATCGAGTGTACAGTGAACAATGCTAGGGAGAGCTGCCT<br>ATATGGAAGAGCCCTAATGTGTAAAATTAATTTTAGTAGTGCTATCCCCATGTGATTTTA<br>AT |

Example 4

Cloning of Shuttle Plasmids with HCV and HIV Nucleic Acid Targets and Integration into *Mycobacterium Smegmatis*

Nucleic acid targets for both HCV and HIV were cloned and a construct was prepared in *E. coli* as described in Example 1, with the nucleic acid targets for HCV and HIV replacing the SARS-CoV-2 targets.

The nucleic acid fragments were derived from publicly available sequences for HIV (NCBI Accession Number NC_001802.1) and HCV (NCBI Accession Number NC_004102.1).

The resulting plasmid was electroporated into *M. smegmatis* mc$^2$155 by standard laboratory methods, as described in Example 1.

The recombinant *M. smegmatis* containing the HIV and HCV targets was added to the Xpert® HIV-1 Viral Load and Xpert® HCV Viral Load cartridges. The digital output of the Xpert® HIV-1 Viral Load and Xpert® HCV Viral Load tests was analysed and a positive result was obtained using the recombinant *M. smegmatis* containing the HIV and HCV genome fragments.

The invention claimed is:

1. A nucleotide cassette having the following formula:

$X_1$-$X_2$-$X_3$-$X_4$-$X_5$ wherein, $X_1$ is an inducible promoter;

$X_2$ is a nucleotide sequence corresponding to at least one single stranded RNA diagnostic target;

$X_3$ is a nucleotide sequence that encodes an artemin protein from *Artemia salina*;

$X_4$ is a molecular switch; and $X_5$ is a nucleotide sequence that encodes a DNAse enzyme and is under control of the molecular switch, wherein the single stranded RNA diagnostic target is a sequence detected by a molecular diagnostic assay.

2. The nucleotide cassette of claim 1, wherein the single stranded RNA diagnostic target is a SARS-CoV-2 target.

3. The nucleotide cassette of claim 2, wherein the SARS-CoV-2 target is selected from the group consisting of RdRP1, RdRP2, N protein, E protein, Spike protein, ORF1ab, and combinations thereof.

4. The nucleotide cassette of claim 1, wherein $X_2$ is selected from the group consisting of SEQ ID NO:2, SEQ ID NO:3, SEQ ID NO:4, SEQ ID NO:5, SEQ ID NO:6, SEQ ID NO:7, and combinations thereof.

5. The nucleotide cassette of claim 1 to wherein the inducible promoter is Hsp60.

6. The nucleotide cassette of claim 1, wherein the molecular switch is a theophylline riboswitch and wherein the DNAse enzyme is produced in the presence of theophylline.

7. The nucleotide cassette of claim 1, comprising the sequence of SEQ ID NO:14 or SEQ ID NO:15.

8. An RNA expression product produced by the nucleotide cassette of claim 1 or having the nucleotide sequence of SEQ ID NO:16 or SEQ ID NO:17.

9. A vector comprising the nucleotide cassette of any one of claim 1.

10. A cell comprising the nucleotide cassette of claim 1.

11. The cell of claim 10, wherein the host cell is a recombinant *Mycobacterium smegmatis* cell.

12. A diagnostic control composition comprising a non-pathogenic recombinant bacterium having a modified genetic content comprising a nucleotide cassette having the following formula:

$X_1$-$X_2$-$X_3$-$X_4$-$X_5$ wherein, $X_1$ is an inducible promoter;

$X_2$ is a nucleotide sequence corresponding to at least one single stranded RNA diagnostic target;

$X_3$ is a nucleotide sequence that encodes an artemin protein from *Artemia salina*;
$X_4$ is a molecular switch; and
$X_5$ is a nucleotide sequence that encodes a DNAse enzyme and is under control of the molecular switch, wherein the single stranded RNA diagnostic target is a sequence detected by a molecular diagnostic assay and wherein the diagnostic control composition mimics the diagnostic profile of a clinical sample in the molecular diagnostic assay.

13. The diagnostic control composition of claim 12, wherein the single stranded RNA diagnostic target is a SARS-CoV-2 target.

14. The diagnostic control composition of claim 13, wherein the SARS-CoV-2 target is selected from the group consisting of RdRP1, RdRP2, N protein, E protein, Spike protein, ORF1ab, and combinations thereof.

15. The diagnostic control composition of claim 12, wherein $X_2$ is selected from the group consisting of SEQ ID NO:2, SEQ ID NO:3, SEQ ID NO:4, SEQ ID NO:5, SEQ ID NO:6, SEQ ID NO:7, and combinations thereof.

16. The diagnostic control composition of claim 12, wherein the inducible promoter is Hsp60.

17. The diagnostic control composition of claim 12, wherein the molecular switch is a theophylline riboswitch and wherein the DNAse enzyme is produced in the presence of theophylline.

18. The diagnostic control composition of claim 12, wherein the nucleotide cassette comprises the sequence of SEQ ID NO:14 or SEQ ID NO:15.

19. The diagnostic control composition of claim 12, wherein the non-pathogenic recombinant bacterium is *Mycobacterium smegmatis*.

20. A method of producing a recombinant bacterium that mimics the diagnostic profile of a single stranded RNA of interest in a molecular diagnostic assay, the method comprising:
transforming a non-pathogenic bacterium with a vector comprising the nucleotide cassette of claim 1 and a selection marker to obtain a recombinant bacterium; and
(ii) culturing the recombinant bacterium obtained in step (i) under selective conditions in order to select the recombinant bacterium.

21. The method of claim 20, wherein the non-pathogenic bacterium is *Mycobacterium smegmatis*.

22. The method of claim 20, wherein the recombinant bacterium mimics the diagnostic profile of SARS-CoV-2.

23. The method of claim 20, wherein the selection marker is an antibiotic selection marker.

24. The method of claim 20, wherein the recombinant bacterium is either stably or transiently transformed with the vector.

25. A kit comprising the cell of claim 10 and instructions for use.

26. A kit comprising the diagnostic control composition of claim 12, and instructions for use.

* * * * *